(12) United States Patent
Wilde et al.

(10) Patent No.: US 11,840,693 B2
(45) Date of Patent: Dec. 12, 2023

(54) RESTORER PLANTS

(71) Applicant: KWS SAAT SE & Co. KGaA, Einbeck (DE)

(72) Inventors: Peer Wilde, Hermannsburg (DE); Viktor Korzun, Einbeck (DE); Jutta Menzel, Bergen (DE); Ruonan Zhou, Stadt Seeland (DE); Nils Stein, Quedlinburg (DE); Bernd Hackauf, Sanitz (DE)

(73) Assignee: KWS SAAT SE & Co. KGaA, Einbeck (DE)

( * ) Notice: Subject to any disclaimer, the term of this patent is extended or adjusted under 35 U.S.C. 154(b) by 80 days.

(21) Appl. No.: 17/695,019

(22) Filed: Mar. 15, 2022

(65) Prior Publication Data

US 2022/0204980 A1 Jun. 30, 2022

Related U.S. Application Data

(62) Division of application No. 16/064,304, filed as application No. PCT/EP2016/008226 on Dec. 21, 2016, now Pat. No. 11,312,967.

(30) Foreign Application Priority Data

Dec. 21, 2015 (DE) .................. 10 2015 016 445.7

(51) Int. Cl.
| | | |
|---|---|---|
| *C12N 15/82* | (2006.01) | |
| *A01H 6/46* | (2018.01) | |
| *C12N 15/74* | (2006.01) | |
| *A01H 5/10* | (2018.01) | |
| *C12Q 1/6895* | (2018.01) | |
| *C12N 1/14* | (2006.01) | |
| *C12Q 1/686* | (2018.01) | |
| *C12R 1/645* | (2006.01) | |

(52) U.S. Cl.
CPC ............. *C12N 15/743* (2013.01); *A01H 5/10* (2013.01); *A01H 6/46* (2018.05); *C12N 1/145* (2021.05); *C12N 15/8282* (2013.01); *C12N 15/8289* (2013.01); *C12Q 1/686* (2013.01); *C12Q 1/6895* (2013.01); *A01H 6/4624* (2018.05); *A01H 6/4672* (2018.05); *C12R 2001/645* (2021.05)

(58) Field of Classification Search
None
See application file for complete search history.

(56) References Cited

FOREIGN PATENT DOCUMENTS

| DE | 10 2013 014 637 A1 | 3/2015 |
|---|---|---|
| WO | 00/75359 | 12/2000 |
| WO | 01/73084 | 10/2001 |
| WO | 2008/153927 | 12/2008 |
| WO | 2010/079430 A1 | 7/2010 |
| WO | 2011/061656 A1 | 5/2011 |
| WO | 2011/072246 | 6/2011 |
| WO | 2014/104878 A1 | 7/2014 |

OTHER PUBLICATIONS

Falke et al., 2009, Plant Breeding, 128:528-531.*
Bernd Hackauf et al., "Development of conserved ortholog set markers linked to the restorer gene Rfp1 in rye", Molecular Breeding, vol. 30, No. 3, pp. 1507-1518, (May 9, 2012), XP035118106, Kluwer Academic Publishers, DO ISSN: 1572-9788, DOI: 10.1007/S11032-02-9736-5.
Database EMBL [Online] Sep. 29, 2009 (Sep. 29, 2009), "Sequence 52057 from patent U.S. Pat. No. 7,569,389.", XP002768181, retrieved from EBI accession No. EM_PAT:GP689296, Database accession No. GP689296 sequence.
Database EMBL [Online] Jun. 25, 2009 (Jun. 25, 2009), "Triticum aestivum cDNA, clone: SET4 K09, cultivar. Chinese Spring", XP002768182, retrieved from EBI accession No. EM_HTC:AK330518, Database accession No. AK330518 sequence.
Database UniProtKB [Online] May 31, 2011 (May 31, 2011), "Predicted Protein", XP002768183, retrieved from Uniprot, Database accession No. F2E8U5 sequence.
Database UniProtKB [Online] Mar. 19, 2014 (Mar. 19, 2014), "Uncharacterised Protein", XP002768184, retrieved from Uniprot, Database accession No. W5DS50 sequence.
Falke et al., "Rye introgression lines as source of alleles for pollen-fertility restoration in Pampa CMS," Plant Breeding, vol. 128, No. 5, pp. 528-531, Oct. 1, 2009, XP055068330, ISSN:0179-9541, DOI: 10.1111/.1439-0523.2008.01589.x.
International Search Report and Written Opinion issued by the International Searching Authority in International Application No. PCT/EP2016/082268 dated Apr. 11, 2017.
International Preliminary Report on Patentability and Written Opinion issued by the International Searching Authority in Application No. PCT/EP2016/082268 dated Jun. 26, 2018.
Stracke, S. et al., "Development of PCR-based markers linked to dominant genes for male-fertility restoration in Pampa CMS of rye (*Secale cereale* L.)", Theoretical and Applied Genetics, vol. 106, No. 7, pp. 1184-1190, (May 2003), XP055354691, ISSN: 0040-5752, DOI: 10.1007/s00122-002-1153-4.

(Continued)

*Primary Examiner* — Jason Deveau Rosen
(74) *Attorney, Agent, or Firm* — Troutman Pepper Hamilton Sanders LLP

(57) ABSTRACT

Hybrid cereals are described which are obtained by restoring the pollen fertility for the Pampa cytoplasmic male sterility (P-CMS) and which are characterized by a reduced linkage drag. Plants are provided, in particular rye, which, as the male pollen parent, are capable of restoring the pollen fertility for the P-CMS. Furthermore, the nucleic acid molecule which carries the necessary information for restoring the P-CMS, DNA and vectors which contain such a nucleic acid molecule, corresponding host cells as well as a protein which can be encoded by the nucleic acid molecule and antibodies directed against it are also described. Furthermore, methods for the production of corresponding hybrid plants and transgenic plants are provided.

9 Claims, 16 Drawing Sheets

Figure 1:
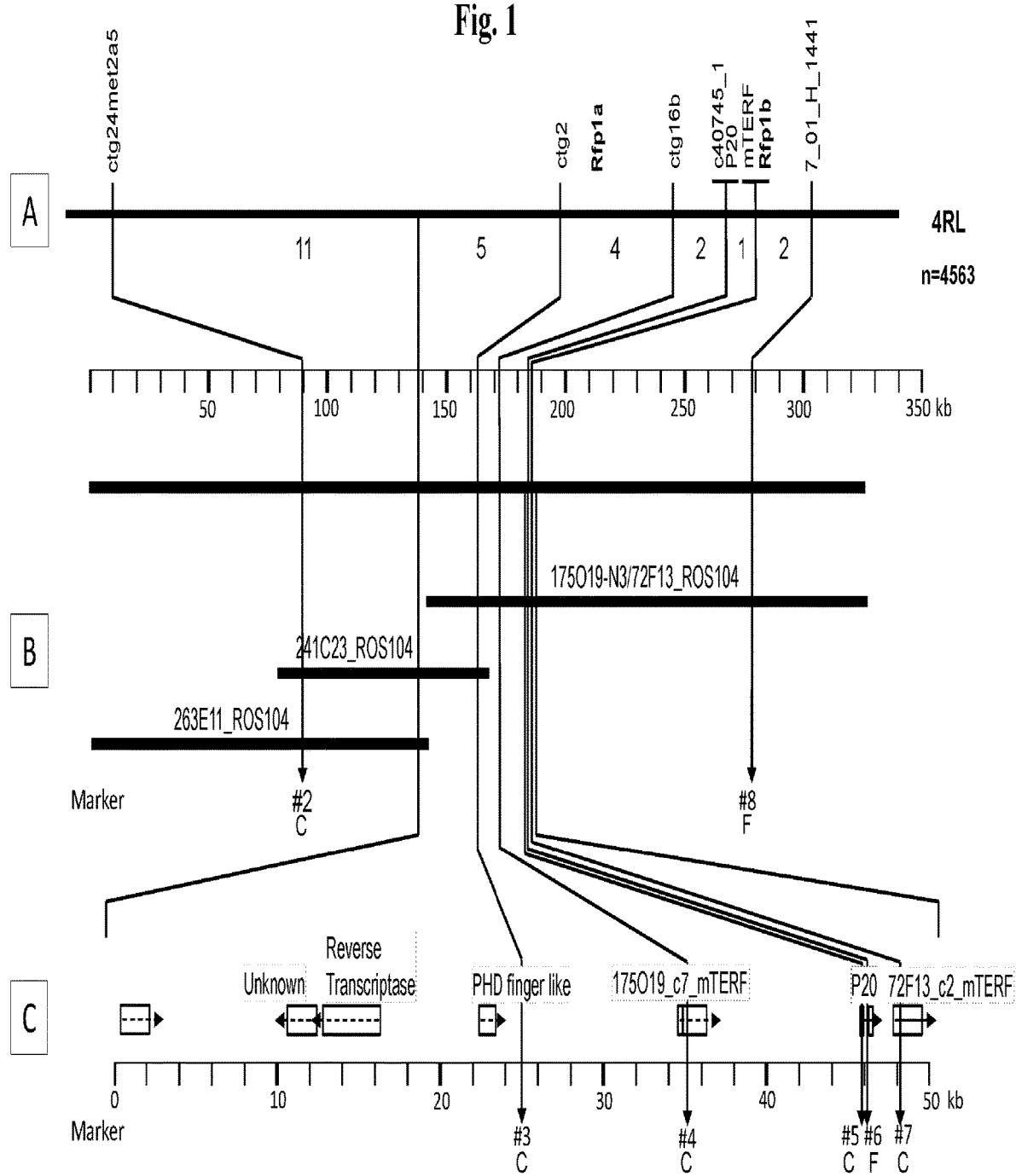

Specification includes a Sequence Listing.

(56) References Cited

OTHER PUBLICATIONS

Geiger et al., "Hybrid Rye and Heterosis", Genetics and Exploitation of Heterosis in Crops, Crop Science Society. America, Madison, Wisconsin, USA (1999): 439-450.
Geiger et al., "Cytoplasmic male sterility in rye (*Secale cereale* L.)", Crop Science, 1970, vol. 10, No. 5, pp. 590-593.
Miedaner et al.,"Mapping of genes for male-fertility restoration in 'Pampa' CMS winter rye (*Secale cereale* L.)", Theor Appl Genet, 2000, vol. 101, pp. 1226-1233.
Small et al., "The PPR motif—a TPR-related motif prevalent in plant organellar proteins", Trends Biochem. Sci., 2000, vol. 25, pp. 46-47.
Hammani et al., "An mTERF domain protein functions in group II intron splicing in maize chloroplasts", Nucleic Acids Research, 2014, vol. 42, No. 8, pp. 5033-5042.
Ruge et al., "Mapping of Rym14Hb, a gene introgressed from Hordeum bulbosum and conferring resistance to BaMMV and BaYMV in barley", Theor Appl Genet, 2003, vol. 107, pp. 965-971.
Gurr et al., "Engineering plants with increased disease resistance: what are we going to express?", Trends in Biotechnology, 2005, vol. 23, No. 6, pp. 275-282.
Venter, "Synthetic promoters: genetic control through cis engineering", Trends in Plant Science, 2007, vol. 12, No. 3, pp. 118-124.
Weeks et al., "Rapid Production of Multiple Independent Lines of Fertile Trangenic Wheat (*Triticum aestivum*)", Plant Physiol., 1993, vol. 102, pp. 1077-1084.
Chan et al., "Agrobacterium-mediated production of transgenic rice plants expressing a chimeric alpha-amylase promoter/ beta-glucuronidase gene", Plant Molecular Biology, 1993, vol. 22, pp. 491-506.
Shimamoto et al., "Fertile transgenic rice plants regenerated from transformed protoplasts", Nature, 1989, vol. 338, pp. 274-276.
Das et al., "Site-selected transposon mutagenesis at the hcf106 locus in maize", The Plant Cell, 1995, vol. 7, No. 3, pp. 287-294.
Till et al., "Discovery of induced point mutations in maize genes by Tilling", BMC Plant Biology, 2004, vol. 4, No. 12, 8 pages.
Silva et al., "Meganucleases and other tools for targeted genome engineering: perspectives and challenges for gene therapy", Current Gene Therapy, 2011, vol. 11, No. 1, pp. 11-27.
Stoddard, "Homing endonucleases: from microbial genetic invaders to reagents for targeted DNA modification", Structure, 2011, vol. 19, No. 1, pp. 7-15.
Lloyd et al., "Targeted mutagenesis using zinc-finger nucleases in *Arabidopsis*", PNAS, 2005, vol. 102, No. 6, pp. 2232-2237.
Gaj et al., "ZFN, TALEN, and CRISPR/Cas-based methods for genome engineering", Trends Biotechnol., 2013, vol. 31, No. 7, pp. 397-405.
Hackauf et al., "Minimizing ergot infection in hybrid rye by a SMART breeding approach", Journal fur Kulturpflanzen, 2009, vol. 61, No. 1, pp. 15-20.
Tanksley et al., "RFLP Mapping in Plant Breeding: New Tools for an Old Science", Bio/Technology, 1989, vol. 7, pp. 257-264.
Shi et al., "Physical analysis of the complex rye (*Secale cereale* L.) Alt4 aluminium (aluminum) tolerance locus using a whole-genome BAC library of rye cv. Blanco", Theor Appl Genet., 2009, vol. 119, No. 4, pp. 695-704.
Murashige et al., "A revised medium for rapid growth and bio assays with tobacco tissue cultures", Physiologia Plantarum, 1962, vol. 15, No. 3, pp. 473-497.
Mersereau et al., "Efficient transformation of Agrobacterium tumefaciens by electroporation", Gene, 1990, vol. 90, No. 1, pp. 149-151.
Lazo et al., "A DNA transformation-competent *Arabidopsis* genomic library in Agrobacterium", Nature Biotechnology, 1991, vol. 9, No. 10, pp. 963-967.
Geiger et al., Angewandt-genetische Studien zur cytoplasmatischen Pollensterilitat bei Winterroggen [Applied genetic studies on cytoplasmic pollen sterility in winter rye], Theor Appl Genet, 1975, vol. 46, No. 6, pp. 269-276.

* cited by examiner

Fig. 2

| Data source | Line | Marker haplotype of NIB partner which carries the donor introgression segment | | | | | | | | Δ (E-D) | | LSD5% |
|---|---|---|---|---|---|---|---|---|---|---|---|---|
| | | ctg32 | ctg24 | ctg2 | RFP1a | ctg16b | c40745 | RFP1b | P20 | in dt/ha | in % of E | in dt/ha |
| | IRAN IX | D | D | D | D | D | D | D | D | | | |
| 094-2014*) | 1110 | D | D | D | D | D | D | E | E | 4.86 | 6.24 | 2.47 |
| | 1039 | D | D | D | D | D | E | E | E | 4.42 | 5.55 | |
| | 1120 | D | D | D | D | E | E | E | E | 3.72 | 4.66 | |
| | 1058 | D | D | E | E | E | E | E | E | 0.85 | 1.05 | |
| 018-2012*) | 455 | E | E | E | E | E | E | D | D | 3.73 | 3.90 | 2.98 |
| | 910 | E | E | E | E | E | E | D | D | 3.05 | 3.12 | |
| | 1446 | E | E | E | E | E | E | D | D | 3.66 | 3.76 | |
| | 1199 | E | E | E | E | E | D | D | D | 6.40 | 6.64 | |
| | 134 | E | E | D | D | D | D | D | D | 6.71 | 6.85 | |
| | 301 | E | E | D | D | D | D | D | D | 6.91 | 7.13 | |
| | 765 | D | D | D | D | D | D | D | D | 7.00 | 7.14 | |

Fig. 7

```
Wildtyp-rfp1a    1 ATGCTCCGCCTCCGGAGTTGCCTCGTCACCCACCTTCTATCCTCTCCCAC   50
                   |||||||||||||||||||||||||||.|||||||.||||||||||||||
Iran9_rfp1a      1 ATGCTCCGCCTCCGGAGTTGCCTCGTCGCCCACCTCCTATCCTCTCCCAC   50

Wildtyp-rfp1a   51 CACCTCCCCACTCCCCTCTCTCCACCGCCTCCTCTCCGCCGCCGCCGCGC  100
                   |.||||||||||||||||||||||||||||||||||||||||||||||||
Iran9_rfp1a     51 CCCCTCCCCACTCCCCTCTCTCCACCGCCTCCTCTCCGCCGCCGCCGCGC  100

Wildtyp-rfp1a  101 CCGCCGTCTCCCCCAGCTCCGGCTTCGACGTCGACGACTATCTCGTCTCC  150
                   |||||||||||||||||||||||||||.|.||.||.|||||.||||||||
Iran9_rfp1a    101 CCGCCGTCTCCCCCAGCTCCGGCTTCCAAGTGGAGGACTACCTCGTCTCC  150

Wildtyp-rfp1a  151 ACCTGCGGGCTGACCCGAGCGCAGGCCCTCAAGGCCACCCCCAAGCTCTC  200
                   ||||||||.||.||||||||||||||||||||||.||.||||||||||||
Iran9_rfp1a    151 ACCTGCGGCCTCACCCGAGCGCAGGCCCTCAAGACCGCCCCCAAGCTCTC  200

Wildtyp-rfp1a  201 CCACCTCAAGTCCCCCGCCAACCCCGACGCCGTCCGCTCCTTCCTCGCCG  250
                   ||||||||||||||||||||||||||||||||||||||||||||||||||
Iran9_rfp1a    201 CCACCTCAAGTCCCCCGCCAACCCCGACGCCGTCCGCTCCTTCCTCGCCG  250

Wildtyp-rfp1a  251 GCCTCGGCCTCTCCGGCGCCGACGTCGCGGCCCTCGTCGCCAGGGACCCG  300
                   ||||||||||||||||||||||||||||||||||||||||||||||||||
Iran9_rfp1a    251 GCCTCGGCCTCTCCGGCGCCGACGTCGCGGCCCTCGTCGCCAGGGACCCG  300

Wildtyp-rfp1a  301 CTCTTCCTCTGCGCCGGCGTGGACGGAAACCTGGGCCCCGCCGTCGCCGG  350
                   |||||||||||||||||||||||.||||||||||||||||||||||||||
Iran9_rfp1a    301 CTCTTCCTCTGCGCCGGCGTGGAGGGAAACCTGGGCCCCGCCGTCGCCGG  350
```

Fig. 7 (cont.)

```
Wildtyp-rfp1a   351 GCTCACCGACCTCGGCCTCTCGCGGGCCGAGGTCGCGCGCCTCGTCTCGC   400
                    |||||||||||||||||||||||||||..|||||||||||||||||||||
Iran9_rfp1a     351 GCTCACCGACCTCGGCCTCTCGCGCTCCGAGGTCGCGCGCCTCGTCTCGC   400

Wildtyp-rfp1a   401 TCTCCCCGGACCGATTCCGCCGCAAGAGCGTCGTCCCCAAGGTGCGGTAC   450
                    ||||||||||||||||||||||||||||||||||||||||||||||||||
Iran9_rfp1a     401 TCTCCCCGGACCGATTCCGCCGCAAGAGCGTCGTCCCCAAGGTGCGGTAC   450

Wildtyp-rfp1a   451 TACCTGCCTCTCTTCGGCTCCCCCGCGGACCTCCTCTCGGGGGTCAAGAC   500
                    ||||||||||||||||||||||||||||||||||||||||||||||||||
Iran9_rfp1a     451 TACCTGCCTCTCTTCGGCTCCCCCGCGGACCTCCTCTCGGGGGTCAAGAC   500

Wildtyp-rfp1a   501 CGGCCTATTCCTTCTCTCCGTCGACCTCGACCGGGTCGTCAAGCCCAATG   550
                    ||||||.|||||||||||||||||||||||||||||||||||||||||.|
Iran9_rfp1a     501 CGGCCTGTTCCTTCTCTCCGTCGACCTCGACCGGGTCGTCAAGCCCAACG   550

Wildtyp-rfp1a   551 TCGCCGTCCTGCGCAAGTGCGGGCTAGGTGTTTGTGATATTGCCAAGCTG   600
                    |||||||||||||||||||||||||||.||||||||||||||||||||||
Iran9_rfp1a     551 TCGCCGTCCTGCGCAAGTGCGGGCTAGATGTTTGTGATATTGCCAAGCTG   600

Wildtyp-rfp1a   601 CTCATCCAAATGCCGAGGATCGTCACCGCCAGCCCCGAGCGCACCCTCGC   650
                    ||||||||||||||||||||||||||||||||||||.|.|||||||||||
Iran9_rfp1a     601 CTCATCCAAATGCCGAGGATCGTCACCGCCAGCCCGGGGCGCACCCTCGC   650

Wildtyp-rfp1a   651 GATGGTCGCGTGCGCCGAGCGCTTGGGTGTGCCCCGTGGCTCCGGGATGT   700
                    ||||||||||||||||||||||||||||||||||||||||||||||||||
Iran9_rfp1a     651 GATGGTCGCGTGCGCCGAGCGCTTGGGTGTGCCCCGTGGCTCCGGGATGT   700
```

Fig. 7 (cont.)

```
Wildtyp-rfp1a   701 TTAGGCAGGCGCTGCAGGCCGTCGCATGCCTCAGCGAGGACAAGATTGCC  750
                    ||||||||||||||||||||||||||||||.|||||||||||||||||||
Iran9_rfp1a     701 TTAGGCAGGCGCTGCAGGCCGTCGCATCCCTCAGCGAGGACAAGATTGCC  750

Wildtyp-rfp1a   751 GCCAAAGTGGAGCAGTTGAAGAAGACACTGAGGTGGTCGGATGCCGATGT  800
                    ||||||||||||||||||||||||||||||||||||||||||||||||||
Iran9_rfp1a     751 GCCAAAGTGGAGCAGTTGAAGAAGACACTGAGGTGGTCGGATGCCGATGT  800

Wildtyp-rfp1a   801 CGGCATTGCTGTCCGCAAGTGGCCGACTGTGCTGAGGTGGTCAAGGGACA  850
                    ||||||||||||||.|||||||||||||.|||||||||||||||||||||
Iran9_rfp1a     801 CGGCATTGCTGTCTGCAAGTGGCCGGCTGTGCTGAGGTGGTCAAGGGACA  850

Wildtyp-rfp1a   851 TGCTGCAGCGCAAGTCCGAGTTCCTCTTCTCTGAGGTGGGCTTGGAACCG  900
                    ||||||||||||||||||||||||||||||||||||||||||||||||||
Iran9_rfp1a     851 TGCTGCAGCGCAAGTCCGAGTTCCTCTTCTCTGAGGTGGGCTTGGAACCG  900

Wildtyp-rfp1a   901 GCGTACGTTGCTCACCGTCCGGCAATGCTCGGTCTTAGCTTGGAGCGCCG  950
                    ||||||.|||||||||||||||||||||||||||||||||||||||||||
Iran9_rfp1a     901 GCGTACATTGCTCACCGTCCGGCAATGCTCGGTCTTAGCTTGGAGCGCCG  950

Wildtyp-rfp1a   951 GCTCAAGCCCAGGTACTATGTTATGAGGTTTCTTAAGGAAAATGGATTGC  1000
                    .|||||||||.|||||||||||||||||||||||||||||||||||||||
Iran9_rfp1a     951 CCTCAAGCCCCGGTACTATGTTATGAGGTTTCTTAAGGAAAATGGATTGC  1000

Wildtyp-rfp1a  1001 TCAGTCATGCCAGAGACTACTATTGTATGGTCTTGGTCAGCGAGAAGGTA  1050
                    ||||||||||||||||||||||||||||||||||||||||||||||||||
Iran9_rfp1a    1001 TCAGTCATGCCAGAGACTACTATTGTATGGTCTTGGTCAGCGAGAAGGTA  1050
```

Fig. 7 (cont.)

```
Wildtyp-rfp1a  1051 TTTGTGGAGCGGTTCATACGCCCCCACAAGCAAGCTGTGCCACGCATTGC  1100
                    ||||||||||||||||||||||||||||||||||||||..||||.|||||
Iran9_rfp1a    1051 TTTGTGGAGCGGTTCATACGCCCCCACAAGCAAGCTGCACCACACATTGC  1100

Wildtyp-rfp1a  1101 TGAAGACTATGCAGCCGCTTGCATAGGGGAGGTGCCTGCTAGATTCAGAT  1150
                    ||||||||||||||||||||||||||||||||||||||||||||||||||
Iran9_rfp1a    1101 TGAAGACTATGCAGCCGCTTGCATAGGGGAGGTGCCTGCTAGATTCAGAT  1150

Wildtyp-rfp1a  1151 TTACATGA  1158
                    ||||||||
Iran9_rfp1a    1151 TTACATGA  1158
```

Fig. 8

```
Wildtyp-rfp1b    1 ATGCTCCTCCTCCTCCGGCAGCGCGTCCTCTCCGCCGCGCCATCTCCATC   50
                   ||||||||||||||||||||||||||||||||||||| ||||||||||.||
Iran9-rfp1b      1 ATGCTCCTCCTCCTCCGGCAGCGCGTCCTCTCCGCTGCGCCATCTCCTTC   50

Wildtyp-rfp1b   51 CACCTCCC---------CTCTCCACCGCCTCCTCTCCGCGGCCGCGCCCG   91
                   ||||||||         |||||||||||||||.|||.|||||||||||
Iran9-rfp1b     51 CACCTCCCCACTCCTCTCTCTCCACCGCCTCCTCTGCGCCGCCGCGCCCG  100

Wildtyp-rfp1b   92 CCGTTTCCCGGAACCCTAGCTTCGCCGTGGAGGAGTACCTCGTCTCCACC  141
                   .|               |||||||||||||||.||.||.|||||||||..||||
Iran9-rfp1b    101 TC---------AACCCTAGCTTCGCCGTCGACGACTACCTCGTCGGCACC  141

Wildtyp-rfp1b  142 TGCGGCCTCACCCGTGCCCAGGCACTCAAGGCCTCCGCCAAGCTCTCCCA  191
                   |||||||||.||||||||||||||||||||||.||||||||||||.|||||
Iran9-rfp1b    142 TGCGGCCTCAGCCGTGCCCAGGCACTCAAGGCATCCGCCAAGCTGTCCCA  191

Wildtyp-rfp1b  192 CCTCAAGTCCCCCGCCAAGCCCGACGCCGTCCTCGCCTTCCTCGCCGGAC  241
                   |||||||||||||||||||.||||||||||||||||||||||||||||||
Iran9-rfp1b    192 CCTCAAGTCCCCCGCCAACCCCGACGCCGTCCTCGCCTTCCTCGCCGGAC  241

Wildtyp-rfp1b  242 TCGGCCTCTCCGGCGCCGACATCGCTGCCCTCGTCGCCAAGGACGCGCGG  291
                   ||||||||||||||||||||..|.||.|||.||||||||||||...|...|
Iran9-rfp1b    242 TCGGCCTCTCCGGCGCCGATGTGGCGGCCGTCGTCGCCAAGGATCCCAAG  291

Wildtyp-rfp1b  292 TTCCTCTGCGCCGGCGTGGAGAGAACCCTGTCCCCATCGTCGCTGGGCT  341
                   |||||||||||||||||||||||.|||||||.|||||.||||||||||||
Iran9-rfp1b    292 TTCCTCTGCGCCGGCGTGGAGACAACCCTGGCCCCCGTCGTCGCTGGGCT  341
```

Fig. 8 (cont.)

```
Wildtyp-rfp1b  342 CACCGGCCTTGGCCTGTCAAATGCTGAGACTGCGCGCCTCGTCTCGCTTG  391
                   ||||||||.||.||||||||||||||||||||||||||||||||||||||
Iran9-rfp1b    342 CACCGGCCTGGGTCTGTCAAATGCTGAGACTGCGCGCCTCGTCTCGCTTG  391

Wildtyp-rfp1b  392 CCCCCGACAAATTCCGCCAGAGATCCATCGTCTCCAAGCTAGAGTACTAC  441
                   ||||||||||||||||||||||||||||||||||||||||||.||||||
Iran9-rfp1b    392 CCCCCGACAAATTCCGCCAGAGATCCATCGTCTCCAAGCTAGACTACTAC  441

Wildtyp-rfp1b  442 CTGCCGCTCGTCGGCTCCATCGACAACTTGGTCCGGTCGCTCAAACACGG  491
                   |||||||||.||||||||||||||||||||||||||||||||||||||||
Iran9-rfp1b    442 CTGCCGCTCTTCGGCTCCATCGACAACTTGGTCCGGTCGCTCAAACACGG  491

Wildtyp-rfp1b  492 CGCCGGCATCCTCGGCTCCGACCTCGAGAGGGTGGTCAAGCCCAATGTTA  541
                   ||||||||||||||||||||||||||||||||||||||||||||||||||
Iran9-rfp1b    492 CGCCGGCATCCTCGGCTCCGACCTCGAGAGGGTGGTCAAGCCCAATGTTA  541

Wildtyp-rfp1b  542 GTCTCCTAGCAGAGTGCGGGCTAGGTGCTTGTGATATTGCCAAGCTGTTC  591
                   ||||||||||||||||||||||||||||||||||||||||||||||||||
Iran9-rfp1b    542 GTCTCCTAGCAGAGTGCGGGCTAGGTGCTTGTGATATTGCCAAGCTGTTC  591

Wildtyp-rfp1b  592 GTCCAAATACCGAGGATGCTGTGTGCTAAACCAGAGCGTGTCCTGGAGAT  641
                   ||||||||||||||||||||||||||||||||||||||||||||||||||
Iran9-rfp1b    592 GTCCAAATACCGAGGATGCTGTGTGCTAAACCAGAGCGTGTCCTGGAGAT  641

Wildtyp-rfp1b  642 GGTTGCGTGTGCCGAAAGTATAGGTGTGTCCCGTGGCTCTGGAATGTTCT  691
                   |||||||||||||||||||||||||||||.||||||||||||||||||.
Iran9-rfp1b    642 GGTTGCGTGTGCCGAAAGTATAGGTGTGCCCCGTGGCTCTGGAATGTTCA  691
```

Fig. 8 (cont.)

```
Wildtyp-rfp1b  692 GGCAAGCGCTGCACACCGTCGCATACGTCAGCGTGGACAATATCGCTGCC  741
                   ||||.|||||||||.|.|||.|||||.||||||...||||||...||.|.||.
Iran9-rfp1b    692 GGCACGCGCTGCACGCTGTCTCATACTTCAGCGACGACAAGCTCACCGCT  741

Wildtyp-rfp1b  742 AGAGTGGACTACTTGAAGAAGACGTTTAGGTGGTCAGATATTGAGGTTGG  791
                   |.||||||||||||||||||||||.||||||||||.|||...||||||||.
Iran9-rfp1b    742 AAAGTGGACTACTTGAAGAAGACATTTAGGTGGTCGGATGCCGAGGTTGC  791

Wildtyp-rfp1b  792 CATTGCTGTGTCCAAGGGTCCATTTCTGCTTAGGAGGTCAAAGGATATGC  841
                   |||||||||||||||||||||||||||||||.||||||||||||||||||.|
Iran9-rfp1b    792 CATTGCTGTGTCCAAGGGTCCATTTCTGCTGAGGAGGTCAAAGGATATTC  841

Wildtyp-rfp1b  842 TGAAACACAGGTCGGAGTTCCTTATCACTGAGCTAGGGTTGCAGCCGGCC  891
                   ||||.||||||.||.||||||||||||||||||.||||||||||||||||||
Iran9-rfp1b    842 TGAAGCACAGCTCCGAGTTCCTTATCACTGAGGTAGGGTTGCAGCCGGCC  891

Wildtyp-rfp1b  892 TACATTGCTCATCGGCCGGCTATGCTCACTTACAGCCTGGAGGGCCGGCT  941
                   ||||||||||||||||||||||||||||||||||||||||||||||||||
Iran9-rfp1b    892 TACATTGCTCATCGGCCGGCTATGCTCACTTACAGCCTGGAGGGCCGGCT  941

Wildtyp-rfp1b  942 CAGGCCCCGCTACTATGTTGTGAGATTTCTCAAGGAAAATGGATTGCTAG  991
                   ||||||||||||||||||||||||||||||||||||||||||||||||||
Iran9-rfp1b    942 CAGGCCCCGCTACTATGTTGTGAGATTTCTCAAGGAAAATGGATTGCTAG  991

Wildtyp-rfp1b  992 AGCACGGGCGGAGCTACTATACAACACTGATTAGTACTGAGAAGGTTTTC  1041
                   ||||||||||||||||||||||||||||||||||||||||||||||||||
Iran9-rfp1b    992 AGCACGGGCGGAGCTACTATACAACACTGATTAGTACTGAGAAGGTTTTC  1041
```

Fig. 8 (cont.)

```
Wildtyp-rfp1b   1042 ATGGAAAAGTTCATACGCCCTCACAAGGAAGCCGCACCACACCTCGCTGA 1091
                     ||||||||||||||||||||||||||||||||||||||||||||||||||
Iran9-rfp1b     1042 ATGGAAAAGTTCATACGCCCTCACAAGGAAGCCGCACCACACCTCGCTGA 1091

Wildtyp-rfp1b   1092 AGACTACGCGGCTGCTTGCAAAGGACAAGTGCCGGCTAGATTCAGATTTA 1141
                     |||||||||||||||||.||||||||||||||||||||||||||||||||
Iran9-rfp1b     1092 AGACTACGCGGCTGCTTACAAAGGACAAGTGCCGGCTAGATTCAGATTTA 1141

Wildtyp-rfp1b   1142 CATGA 1146
                     |||||
Iran9-rfp1b     1142 CATGA 1146
```

Fig. 9

```
Wildtyp-rfp1a    1 MLRLRSCLVTHLLSSPTTSPLPSLHRLLSAAAAPAVSPSSGFDVDDYLVS    50
                   ||||||||.|||||||.|||||||||||||||||||||||||.:||||
Iran9-rfp1a      1 MLRLRSCLVAHLLSSPTPSPLPSLHRLLSAAAAPAVSPSSGFQVEDYLVS    50

Wildtyp-rfp1a   51 TCGLTRAQALKATPKLSHLKSPANPDAVRSFLAGLGLSGADVAALVARDP   100
                   |||||||||||..|||||||||||||||||||||||||||||||||||||
Iran9-rfp1a     51 TCGLTRAQALKTAPKLSHLKSPANPDAVRSFLAGLGLSGADVAALVARDP   100

Wildtyp-rfp1a  101 LFLCAGVDGNLGPAVAGLTDLGLSRAEVARLVSLSPDRFRRKSVVPKVRY   150
                   ||||||:|||||||||||||||||||:|||||||||||||||||||||||
Iran9-rfp1a    101 LFLCAGVEGNLGPAVAGLTDLGLSRSEVARLVSLSPDRFRRKSVVPKVRY   150

Wildtyp-rfp1a  151 YLPLFGSPADLLSGVKTGLFLLSVDLDRVVKPNVAVLRKCGLGVCDIAKL   200
                   ||||||||||||||||||||||||||||||||||||||||||.|||||||
Iran9-rfp1a    151 YLPLFGSPADLLSGVKTGLFLLSVDLDRVVKPNVAVLRKCGLDVCDIAKL   200

Wildtyp-rfp1a  201 LIQMPRIVTASPERTLAMVACAERLGVPRGSGMFRQALQAVACLSEDKIA   250
                   |||||||||||.||||||||||||||||||||||||||||||||.|||||||
Iran9-rfp1a    201 LIQMPRIVTASPGRTLAMVACAERLGVPRGSGMFRQALQAVASLSEDKIA   250

Wildtyp-rfp1a  251 AKVEQLKKTLRWSDADVGIAVRKWPTVLRWSRDMLQRKSEFLFSEVGLEP   300
                   ||||||||||||||||||||||.|||.|||||||||||||||||||||||
Iran9-rfp1a    251 AKVEQLKKTLRWSDADVGIAVCKWPAVLRWSRDMLQRKSEFLFSEVGLEP   300

Wildtyp-rfp1a  301 AYVAHRPAMLGLSLERRLKPRYYVMRFLKENGLLSHARDYYCMVLVSEKV   350
                   ||:||||||||||||||||||||||||||||||||||||||||||||||
Iran9-rfp1a    301 AYIAHRPAMLGLSLERRLKPRYYVMRFLKENGLLSHARDYYCMVLVSEKV   350

Wildtyp-rfp1a  351 FVERFIRPHKQAVPRIAEDYAAACIGEVPARFRFT    385
                   ||||||||||||.|.||||||||||||||||||||
Iran9-rfp1a    351 FVERFIRPHKQAAPHIAEDYAAACIGEVPARFRFT    385
```

Fig. 10

```
Wildtyp-rfp1b    1 MLLLLRQRVLSAAPSPSTSP---LHRLLSAAAPAVSRNPSFAVEEYLVST    47
                   ||||||||||||||||||||   |||||.||||.   ||||||::|||.|
Iran9-rfp1b      1 MLLLLRQRVLSAAPSPSTSPLLSLHRLLCAAAPV---NPSFAVDDYLVGT    47

Wildtyp-rfp1b   48 CGLTRAQALKASAKLSHLKSPAKPDAVLAFLAGLGLSGADIAALVAKDAR    97
                   |||:||||||||||||||||||.|||||||||||||||||:||:||||.:
Iran9-rfp1b     48 CGLSRAQALKASAKLSHLKSPANPDAVLAFLAGLGLSGADVAAVVAKDPK    97

Wildtyp-rfp1b   98 FLCAGVERTLSPIVAGLTGLGLSNAETARLVSLAPDKFRQRSIVSKLEYY   147
                   ||||||.||:|:||||||||||||||||||||||||||||||||||||:||
Iran9-rfp1b     98 FLCAGVETTLAPVVAGLTGLGLSNAETARLVSLAPDKFRQRSIVSKLDYY   147

Wildtyp-rfp1b  148 LPLVGSIDNLVRSLKHGAGILGSDLERVVKPNVSLLAECGLGACDIAKLF   197
                   |||.||||||||||||||||||||||||||||||||||||||||||||||
Iran9-rfp1b    148 LPLFGSIDNLVRSLKHGAGILGSDLERVVKPNVSLLAECGLGACDIAKLF   197

Wildtyp-rfp1b  198 VQIPRMLCAKPERVLEMVACAESIGVSRGSGMFWQALHTVAYVSVDNIAA   247
                   ||||||||||||||||||||||||||.||||||..|||.|:|.|.|.:.|
Iran9-rfp1b    198 VQIPRMLCAKPERVLEMVACAESIGVPRGSGMFRHALHAVSYFSDDKLTA   247

Wildtyp-rfp1b  248 RVDYLKKTFRWSDIEVGIAVSKGPFLLRRSKDMLKHRSEFLITELGLQPA   297
                   :|||||||||||.||.|||||||||||||||:|||.||||||:|||||
Iran9-rfp1b    248 KVDYLKKTFRWSDAEVAIAVSKGPFLLRRSKDILKHSSEFLITEVGLQPA   297

Wildtyp-rfp1b  298 YIAHRPAMLTYSLEGRLRPRYYVVRFLKENGLLEHGRSYYTTLISTEKVF   347
                   ||||||||||||||||||||||||||||||||||||||||||||||||||
Iran9-rfp1b    298 YIAHRPAMLTYSLEGRLRPRYYVVRFLKENGLLEHGRSYYTTLISTEKVF   347

Wildtyp-rfp1b  348 MEKFIRPHKEAAPHLAEDYAAACKGQVPARFRFT      381
                   |||||||||||||||||||||||.||||||||||
Iran9-rfp1b    348 MEKFIRPHKEAAPHLAEDYAAAYKGQVPARFRFT      381
```

RESTORER PLANTS

CROSS-REFERENCE TO RELATED APPLICATIONS

This application is a divisional of U.S. application Ser. No. 16/064,304, filed Jun. 20, 2018, which is a U.S. National Phase of International Patent Application No. PCT/EP2016/082268, filed Dec. 21, 2016, which claims priority to German Patent Application No. 102015016445.7, filed on Dec. 21, 2015.

The entire contents of these applications are incorporated herein by reference in their entirety.

SEQUENCE LISTING

This application contains a Sequence Listing which has been submitted in ASCII format via EFS-Web and is hereby incorporated by reference herein in its entirety. The ASCII text file was created on Jun. 29, 2017, is named Sequence_Listing.txt and is 53,790 bytes in size.

FIELD OF THE INVENTION

The present invention relates to the technical field of plant breeding and green biotechnology, in particular the field of the production of hybrid plants using molecular biological methods, marker technology and genetic engineering. In particular, hybrid cereals are provided which are obtained by restoring pollen fertility for the cytoplasmic male sterility (P-CMS) which is produced by the Pampa cytoplasm, and/or which comprise complete restoration of pollen fertility for the cytoplasmic male sterility (P-CMS) which is produced by the Pampa cytoplasm. They are characterized by the fact that negative, usually yield-reducing effects remain which are otherwise connected with the introgression of chromosomal segments which contain the locus responsible for restoration in cultivars. In this respect, the present invention provides plants, in particular rye plants which, as the male pollen parent, are capable of restoring pollen fertility for the P-CMS whereupon, in hybrid plants from a cross of these pollen parents with a female CMS parent, a linkage drag otherwise coupled with the restoration property is reduced or is even completely eliminated.

Furthermore, the present invention relates to nucleic acid molecules which carry the necessary information for restoration of the P-CMS, DNA and vectors which contain such a nucleic acid molecule, corresponding host cells as well as a protein which can be coded for by the nucleic acid molecule and antibodies directed against it. Furthermore, the invention concerns the use of the nucleic acid molecules, DNA, vectors and antibodies in the production of hybrid plants, for example.

BACKGROUND OF THE INVENTION

Because of its pronounced stress tolerance in nutrient-deficient, dry locations as well as in catchment areas with limited pesticide use, rye exhibits substantial yield advantages compared with barley and wheat, and thus holds specific promise for sustainable agriculture. The use of cytoplasmic male sterility (CMS) in rye, inter alia, has opened up the possibility of breeding hybrid varieties with high yield potentials by exploiting heterosis (Geiger, H. H., and T. Miedaner, "hybrid rye and heterosis." *Genetics and Exploitation of Heterosis in Crops. Crop Science Society.* America, Madison, Wisconsin, USA (1999): 439-450). The importance of hybrids in rye as an agricultural cultivation variety in Europe is steadily increasing. In Germany, Denmark or Austria alone, hybrid rye already takes up more than 70% of the total production of rye. In other regions too, in particular in Eastern Europe, in future years there is expected to be a significant increase in hybrid rye cultivation. The main uses for rye are in animal fodder and in bread production, for which the rye is usually mixed with other cereals. Furthermore, rye is gaining increasing significance as a substrate for obtaining bioenergy.

Currently, most hybrid systems in rye are based on exploiting Pampa (P) cytoplasm which, together with non-restorers, mediates male sterility (P-CMS) in the nuclear genome. This was discovered at the end of the 1960s in an Argentinian breed (Geiger, H. H., and F. W. Schnell. "Cytoplasmic male sterility in rye (*Secale cereale* L.)." *Crop Science* 10.5 (1970): 590-593). This CMS exhibits excellent stability to environmental conditions and is stably maintained in all European breeding populations in current non-restorer genotypes. The search for efficient restorers for the male fertility of P-CMS, was richly rewarded in primitive rye accessions such IRAN IX, Pico Gentario or Altevogt 14160 (Geiger H H, Miedaner T (1996) Genetic basis and phenotypic stability of male-fertility restoration in rye. Vortr plantszüchtg 35:27-38; Miedaner T, Glass C, Dreyer F, Wilde P, Wortmann H, Geiger H H (2000) Mapping of genes for male fertility restoration in "Pampa" CMS winter rye (*Secale cereale* L.). Theor Appl Genet 101:1226-1233; Falke K C, Wilde P, Miedaner T (2009) Rye introgression lines as source of alleles for pollen-fertility restoration in Pampa CMS. Plant Breeding 128:528-531). IRAN IX is a self-incompatible rye population which was collected from the Elburz-Karaj region by Kuckuck (1956; Report to the government of Iran on the distribution and variation of cereals in Iran. FAO Report No. 517:1-22) and deposited in the gene bank of the former Bundesforschungsanstalt für Landwirtschaft [Federal Agricultural Research Centre, FAL]. The Pico Gentario accession originates from Argentina and the Altevogt 14160 population also originates from Iran. Both are also self-incompatible and can be obtained from the Botanical Gardens of the Polish Academy of Sciences in Warsaw. Compared with restorer genotypes which originate from central European sources, the restorers from IRAN IX, Pico Gentario or Altevogt 14160 exhibit a high and stable restoration capability. In contrast to current sources from central Europe, this manifests itself in very good pollen shedding, a property which plays a decisive role in minimizing ergot. Ergot infestation is one of the most economically significant diseases of rye (*Claviceps purpurea* [Fr.] Tul.). As a result, since 2008, the susceptibility of rye varieties to ergot has been officially entered in the variety list of the Federal Plant Variety Office and also by the Polish Plant Variety Office (COBORU) when evaluating rye hybrids. Improving the pollen shedding trait in hybrid varieties, for example with winter rye, by effective restorer loci such as Rfp1, is currently the most effective and sustainable strategy for minimizing the contamination of crops with ergot in hybrid rye. Overall, the introgression of these restorer sources into pollen parent lines constitutes a significant advance for the restoration of fertility in hybrids.

Mapping studies to localise the restorer locus Rfp1 of the donor IRAN IX, Rfp2 of the donor Pico Gentario or the locus from Altevogt 14160 each produced a position on the long arm of chromosome 4R (Miedaner et al. 2000. Mapping of genes for male fertility restoration in "Pampa" CMS winter rye (*Secale cereale* L.). Theor Appl Genet 101:1226-1233; Stracke et al. 2003. Development of PCR-based markers linked to dominant genes for male-fertility restoration in Pampa CMS of rye (*Secale cereale* L.), Theor Appl Genet (2003) 106:1184-1190; Falke et al. 2009. Rye introgression lines as source of alleles for pollen-fertility restoration in Pampa CMS. Plant Breeding 128:528-531, Hackauf et al. 2012. Development of COS markers for the Restorer Gene Rfp1 in Rye. Molecular Breeding 30: 1507-1518). Studies with associated selection markers have shown that several restorer genes could possibly be clustered in the region concerned on chromosome 4 RL, or the restorer gene concerned could be an allele of one and the same gene locus (Hackauf et al. (2012) "Development of conserved ortholog set markers linked to the restorer gene Rfp1 in rye." *Molecular breeding* 30.3: 1507-1518).

Although the use of the present restorer loci is advantageous on the one hand in view of restoration capability and pollen shedding, on the other hand, the associated introgression segments containing the restorer loci reduce the agronomic performance of today's breeding populations. In particular, the grain yield is so significantly deleteriously affected by the genome region flanking the restorer genes (linkage drag) that the advantage of the heterosis effect in the hybrids is drastically cut down or even completely destroyed. Furthermore, the possibility has also been discussed that the observed linkage drag effect or at least a portion thereof is actually a pleiotropic effect of the restorer gene. Despite intensive backcross studies accompanied by extensive marker development over a period which has now lasted more than ten years, until now, only a coarse genetic position has been determined. By means of continuous selection over more or less closely coupled foreground markers and the target gene, the size of the introgression fragment with the restorer locus has been largely maintained, thus also maintaining a large number of unsuitable donor genes, making the observed linkage drag effect directly plausible. Hackauf et al., (2012) ("Development of conserved ortholog set markers linked to the restorer gene Rfp1 in rye." *Molecular breeding* 30.3 (2012): 1507-1518) show for Rfp1 the most up-to-date situation regarding mapping of the genome region of interest around the restorer locus on 4R. By using a comparative approach to gene mapping on the basis of completely decoded grass genomes, they were able to limit the introgression segment including the Rfp1 locus itself to an interval of approximately 2.0 cM, flanked by the markers tc135788 and tc176835, or to an interval of 0.7 cM, flanked by the markers tc256739 and tc300731. However, the restorer gene itself could not be identified, nor until now have substantiated results been obtained regarding the extent and localization of the reduction in agronomic performance. It is also not known to produce recombinants for which the change in the introgression segment and the agronomic performance could be correlated.

The objective of the present invention is therefore to further develop the introgression segments at the basis of the aforementioned restorer loci so that they indeed maintain the desired restoration property, however the reductions in performance are no longer exhibited or are significantly reduced or minimized. In particular, the objective of the invention was to embed, and thus provide, the restorer genes which constitute an essential fundamental of hybrid breeding programs in grasses, preferably in cereals, into high resolution fine mapping of the associated region. Furthermore, in the context of the invention, genotypes should be made available which, with the aid of close-coupled markers around the restorer locus, describe haplotypes for the target region which can be precisely, quantitatively and qualitatively ascribed to the change in agronomic performance. Furthermore, the objective of the invention is to identify markers which are embedded in the restorer gene itself so that with them, the restorer gene can be provided for breeding purposes.

DESCRIPTION OF THE INVENTION

The above objective is achieved by the provision of a plant, in particular from the gramineous order (*Poales*), which is suitable, as a male pollen parent, for restoring the pollen fertility for the Pampa cytoplasmic male sterility (P-CMS). Preferably, it is a plant from the sweetgrass family (*Poaceae*) or from the genus *Secale* or *Hordeum* and particularly preferably a plant from the species *Secale cereale* or *Hordeum vulgare*. The plant is further characterized in that in the plant or in a hybrid plant obtainable from a cross of the plant with a female CMS parent from the same species, a linkage drag effect (see Hackauf et al. 2012) otherwise coupled with the restoration property, preferably a yield-reducing effect, is reduced or completely eliminated. With the aid of the present invention, in this manner, a plant can be provided in which, in the restorer locus, negative unwanted agronomic properties could be decoupled from the restorer genes Rfp1a and Rfp1b. This decoupling means that a high yield can be connected with an efficient restoration capability.

In a particular embodiment, cells of the plants have a cytoplasm which mediates Pampa cytoplasmic male sterility (CMS). Hence, the present invention also provides a hybrid plant with a high yield potential which has a very efficient restoration capability, or a plant which, as a pollen parent, is suitable for restoring pollen fertility for the Pampa cytoplasmic male sterility (CMS), preferably completely. Simultaneously, the linkage drag, which can significantly reduce the agronomic performance, in particular a reduction in yield, is reduced or completely eliminated.

In a preferred embodiment, a plant is provided which comprises a chromosomal segment which comprises at least one nucleic acid molecule which is capable of mediating the restoration property for the Pampa cytoplasmic male sterility. Preferably, the chromosomal segment is an interval between the marker loci tc256739, ctg32 or ctg24met2a5 and tc300731 or 7_01_H_1441 on chromosome 4R from a donor selected from the group consisting of IRAN IX, Pico Gentario and Altevogt 14160. Furthermore, the described chromosomal segment may also be found in other related donors. Such donors can in particular be found in Mediterranean regions, for example Turkey or Spain, having regard to the genetic structure of the chromosomal segment as well as the at least one nucleic acid molecule described herein. In this regard, for example, molecular markers in accordance with the invention such as those described below may be employed. Thus, the present invention is not limited to donors from the group consisting of IRAN IX, Pico Gentario and Altevogt 14160 but, even if not explicitly mentioned, also encompasses more closely related donors which can act as the source of the chromosomal segment in accordance with the invention and of the at least one nucleic acid molecule in accordance with the invention.

Such a chromosomal segment may, for example, be one of the following intervals: between the marker loci tc256739 and tc300731, between the marker loci ctg32 and tc300731, between the marker loci ctg24met2a5 and tc300731, between the marker loci ctg2 and tc300731, between the marker loci ctg16b and tc300731, between the marker loci c40745_1 and tc300731, between the marker loci P20 and tc300731, between the marker loci tc256739 and 7_01_H_1441, between the marker loci ctg32 and 7_01_H_1441, between the marker loci ctg24met2a5 and 7_01_H_1441, between the marker loci ctg2 and 7_01_H_1441, between the marker loci ctg16b and 7_01_H_1441, between the marker loci c40745_1 and 7_01_H_1441, between the marker loci P20 and 7_01_H_1441, between the marker loci tc256739 and 72F13_c2_mTERF, between the marker loci tc256739 and P20, between the marker loci tc256739 and c40745_1, between the marker loci tc256739 and ctg16b, between the marker loci ctg32 and 72F13_c2_mTERF, between the marker loci ctg32 and P20, between the marker loci ctg32 and c40745_1, between the marker loci ctg32 and ctg16b, between the marker loci ctg24met2a5 and 72F13_c2_mTERF, between the marker loci ctg24met2a5 and P20, between the marker loci ctg24met2a5 and c40745_1, between the marker loci ctg24met2a5 and ctg16b, between the marker loci ctg2 and 72F13_c2_mTERF, between the marker loci ctg2 and P20, between the marker loci ctg2 and c40745_1 or between the marker loci ctg2 and ctg16b. Furthermore, the linkage drag effect is preferably that linkage drag effect which was originally coupled with the chromosomal segment from which the restoring nucleic acid molecule originates. Furthermore, the nucleic acid molecule is preferably a nucleic acid molecule which has a nucleotide sequence which codes for a mitochondrial transcription termination factor (mTERF), a homologue, an analogue, an orthologue or a functional fragment thereof. "At least one nucleic acid molecule" may mean one, two, three, four or five nucleic acid molecules; preferably, "at least one nucleic acid molecule" means one or two nucleic acid molecules. The source of the chromosomal segment which comprises at least one nucleic acid molecule which is capable of mediating the restoration property for the Pampa cytoplasmic male sterility may be the primitive rye accessions IRAN IX, Pico Gentario and Altevogt 14160 (Geiger et al., Vortr plantszüchtg 35 (1996), 27-38; Miedaner et al., Theor Appl Genet 101 (2000), 1226-1233; Falke et al., Plant Breeding 128 (2009), 528-531). IRAN IX is a self-incompatible rye population from Elburz-Karaj, collected by Kuckuck (FAO Report No. 517 (1956), 1-22) and held in the gene bank of the Bundesforschungsanstalt für Landwirtschaft [Federal Agricultural Research Centre, FAL]. The Pico Gentario accession from Argentina and the Altevogt 14160 population from Iran are also self-incompatible and were both provided by the Botanical Gardens of the "Polish Academy of Sciences" in Warsaw, Poland.

In a particularly preferred embodiment, the at least one nucleic acid molecule has a nucleotide sequence which is selected from the group consisting of: (i) a nucleotide sequence with one of SEQ ID NO: 1 or SEQ ID NO: 28 or a functional fragment thereof, (ii) a nucleotide sequence which codes for an amino acid sequence with one of SEQ ID NO: 2 or SEQ ID NO: 29 or a functional fragment thereof, (iii) a nucleotide sequence which is complementary to a nucleotide sequence in accordance with (i) or (ii), (iv) a nucleotide sequence which hybridizes with a sequence in accordance with (iii) under stringent conditions, (v) a nucleotide sequence which has an identity of at least 70%, 75%, 80%, 85% or 90%, preferably of at least 91%, 92%, 93% 94% or 95%, or particularly preferably of at least 96%, 97%, 98%, 99% or 99.5% with the nucleotide sequence in accordance with (i) or (ii), (vi) a nucleotide sequence which codes for an amino acid sequence which has an identity of at least 65%, 70%, 75%, 80%, 85% or 90%, preferably of at least 91%, 92%, 93% 94% or 95%, or particularly preferably of at least 96%, 97%, 98%, 99% or 99.5% with one of SEQ ID NO: 2 or SEQ ID NO: 29 or a functional fragment thereof, (vii) a nucleotide sequence which codes for an amino acid sequence which, compared with the amino acid sequence shown in SEQ ID NO: 2 or SEQ ID NO: 29, exhibits discrepancies in the amino acid sequence in the form of amino acid deletions, substitutions, additions and/or insertions in the amino acid sequence, preferably of no more than 30%, 25% or 20%, preferably no more than 18%, 16%, 14%, 12% or 10% or particularly preferably no more than 9%, 8%, 7%, 6%, 5%, 4%, 3%, 2%, 1% or 0.5% over the entire amino acid sequence. Preferably, the at least one nucleic acid molecule codes for one or more mitochondrial transcription termination factors (mTERF) or a functional fragment thereof. The mTERF protein family shares several important functions with what is known as the pentatricopeptide (PPR) family. Like the mTERF protein family, the pentatricopeptide (PPR) family is also an unusual family of RNA binder proteins which is characterized by degenerate helical repeats. In the PPR family, this consists of approximately 35 amino acids (Small et al., Trends Biochem. Sci. 25 (2000), 46-47), in contrast to the mTERF repeats, which are mainly characterized by approximately 31 amino acids, which form three instead of two helices (Hammani et al., Nucleic Acids Res 42 (2014), 5033-5042). It is not possible to exclude the possibility that the presence of one or more functional PPR genes could have a deleterious effect on the positive effect of the plants described above with improved properties. Thus, the nucleic acid molecule of the plant in one embodiment preferably does not have a functional pentatricopeptide (PPR) gene which originates from the donor.

As described above under (vii), the at least one nucleic acid molecule may code for an amino acid sequence which, compared with the amino acid sequence of SEQ ID NO: 2 or of SEQ ID NO: 29, contains an amino acid sequence with discrepancies in the form of amino acid substitutions, deletions, insertions and/or additions. Preferably, such a nucleic acid molecule is capable of binding to a complementary sequence to SEQ ID NO: 1 or 2 or to SEQ ID NO: 28 or 29 under stringent conditions.

As will be shown in the examples below, close-flanking markers of the Rfp1 gene could be identified and thus close-coupled markers be produced for high resolution mapping of the Rfp1 gene in rye; inter alia, these enabled the restorer gene to be flanked and the Rfp1 target region to be elucidated in cereal genomes. Thus, for the first time, a marker-based transfer of the target gene into new breeding material is possible, such that an efficient selection against the unwanted genetic background of the donor genome is included.

In a preferred embodiment, the chromosomal segment of the plant has one or more of the following marker loci of the donor: ctg2 (amplification product of the primer with SEQ ID NOs: 4 and 5), P20 (amplification product of the primer with SEQ ID NOs: 6 and 7), 72F13_c2_mTERF (amplification product of the primer with SEQ ID NOs: 8 and 9) or ctg16b (amplification product of the primer with SEQ ID NOs: 10 and 11). The restoration property of the plant may also be characterized by the absence of one or more of the following marker loci of the donor: 7_01_H_1441 (amplification product of the primer with SEQ ID NOs: 12 and 13), ctg24met2a5 (amplification product of the primer with SEQ ID NOs: 14 and 15), or ctg32 (amplification product of the primer with SEQ ID NOs: 16 and 17).

In a particularly preferred embodiment, the chromosomal segment of the plant comprises the marker loci of the donor ctg32, ctg24met2a5, ctg2, ctg16b and c40745_1 (amplification product of the primer with SEQ ID NOs: 18 and 19) and the marker loci of the donor tc256739 (amplification product of the primer with SEQ ID NOs: 21 and 22), 72F13_c2_mTERF, P20, 7_01_H_1441 and tc300731 (amplification product of the primer with SEQ ID NOs: 23 and 24) are absent on the chromosomal segment.

In a further particularly preferred embodiment, the chromosomal segment of the plant comprises the marker loci of the donor ctg32, ctg24met2a5, ctg2 and ctg16b, and the marker loci of the donor tc256739, c407451_1, 72F13_c2_mTERF, P20, 7_01_H_1441 and tc300731 are absent on the chromosomal segment.

In a further particularly preferred embodiment, the chromosomal segment of the plant comprises the marker loci of the donor ctg32, ctg24met2a5 and ctg2, and the marker loci of the donor tc256739, ctg16b, c40745_1, 72F13_c2_mTERF, P20, 7_01_H_1441 and tc300731 are absent on the chromosomal segment.

In a further particularly preferred embodiment, the chromosomal segment of the plant comprises the marker loci of the donor 72F13_c2_mTERF, P20 and 7_01_H_1441, and the marker loci of the donor tc256739, ctg32, ctg24met2a5, ctg2, ctg16b, c40745_1 and tc300731 are absent on the chromosomal segment.

In a further particularly preferred embodiment, the chromosomal segment of the plant comprises the marker loci of the donor 72F13_c2_mTERF and P20, and the marker loci of the donor tc256739, ctg32, ctg24met2a5, ctg2, ctg16b, c40745_1, 7_01_H_1441 and tc300731 are absent on the chromosomal segment.

In a further particularly preferred embodiment, the chromosomal segment of the plant comprises the marker loci of the donor c407451, 72F13_c2_mTERF, P20 and 7_01_H_1441, and the marker loci of the donor tc256739, ctg32, ctg24met2a5, ctg2, ctg16b and tc300731 are absent on the chromosomal segment.

In a further particularly preferred embodiment, the chromosomal segment of the plant comprises the marker loci of the donor c407451, 72F13_c2_mTERF and P20, and the marker loci of the donor tc256739, ctg32, ctg24met2a5, ctg2, ctg16b, 7_01_H_1441 and tc300731 are absent on the chromosomal segment.

In a further particularly preferred embodiment, the chromosomal segment of the plant comprises the marker loci of the donor ctg16b, c40745_1, 72F13_c2_mTERF, P20 and 7_01_H_1441, and the marker loci of the donor tc256739, ctg32, ctg24met2a5, ctg2 and tc300731 are absent on the chromosomal segment.

In a further particularly preferred embodiment, the chromosomal segment of the plant comprises the marker loci of the donor ctg16b, c40745_1, 72F13_c2_mTERF and P20, and the marker loci of the donor tc256739, ctg32, ctg24met2a5, ctg2, 7_01_H_1441 and tc300731 are absent on the chromosomal segment.

In a further particularly preferred embodiment, the chromosomal segment of the plant comprises the marker loci of the donor ctg2, ctg16b, c40745_1, 72F13_c2_mTERF, P20 and 7_01_H_1441, and the marker loci of the donor tc256739, ctg32, ctg24met2a5 and tc300731 are absent on the chromosomal segment.

In a further particularly preferred embodiment, the chromosomal segment of the plant comprises the marker loci of the donor ctg2, ctg16b, c40745_1, 72F13_c2_mTERF and P20, and the marker loci of the donor tc256739, ctg32, ctg24met2a5, 7_01_H_1441 and tc300731 are absent on the chromosomal segment.

In a further particularly preferred embodiment, the chromosomal segment of the plant comprises the marker loci of the donor ctg24met2a5, ctg2, ctg16b, c40745_1, 72F13_c2_mTERF, P20 and 7_01_H_1441, and the marker loci of the donor tc256739, ctg32 and tc300731 are absent on the chromosomal segment.

In a further particularly preferred embodiment, the chromosomal segment of the plant comprises the marker loci of the donor ctg24met2a5, ctg2, ctg16b, c40745_1, 72F13_c2_mTERF and P20, and the marker loci of the donor tc256739, ctg32, 7_01_H_1441 and tc300731 are absent on the chromosomal segment.

In a preferred embodiment, the chromosomal segment is no larger than 190 kb, no larger than 150 kb or no larger than 100 kb, preferably no larger than 75 kb or no larger than 50 kb, particularly preferably no larger than 40 kb, no larger than 30 kb, no larger than 25 kb or no larger than 20 kb. In a particularly preferred embodiment, the chromosomal segment comprises a DNA fragment of 18.425 kb, which preferably has a nucleotide sequence with SEQ ID NO: 20 or a nucleotide sequence which has an identity of at least 85% or 90%, preferably of at least 91%, 92%, 93% 94% or 95%, or particularly preferably of at least 96%, 97%, 98%, 99% or 99.5% with the nucleotide sequence with SEQ ID NO: 20.

In a further preferred embodiment, the nucleic acid molecule does not have a functional pentatricopeptide (PPR) gene which originates from the donor.

The plant of the present invention is preferably an inbred plant, a double haploid plant or a hybrid plant and/or, preferably, homozygous or heterozygous for the restoration property, for the chromosomal segment or the at least one nucleic acid molecule. The hybrid plant may be a "single-cross" hybrid, a "double-cross" hybrid, a "topcross" hybrid, a "three-way-cross" hybrid, a "triple-cross" hybrid, a "composite" hybrid, a "blended" hybrid, a fully restored hybrid, a "second generation" hybrid or another hybrid. Preferably, a plant of the present invention acts as a pollen donor in a hybrid-produced cross and/or in fertilization of grain or seeds on a hybrid plant.

The identification of the restorer genes described in this study as well as the factors responsible for linkage drag was in general carried out in grasses. Preferably, however, the results shown here were obtained in cereals, wherein the plants primarily belong to the genuses rye (*Secale*), barley (*Hordeum*) or a cereal species cultivated from rye (first partner) and wheat (second partner) known as *Triticale*. The negative effect of linkage drag close-coupled to the restorer locus Rfp1 plays a decisive role in hybrid breeding of cereals, in particular such as rye, for example and in rye, as is known, results in substantial reductions in yield. Comparable difficulties are also known for the hybrid breeding of barley. Because of the genetic similarities in the chromosomal region of the restorer locus between rye and barley as well as *Triticale*, in one embodiment of the present invention, the plant is a plant of the genus *Secale, Hordeum* or *Triticale*, preferably a plant of the species *Secale cereale* or *Hordeum vulgare*.

In addition to plants with excellent restoration properties and without linkage drag or with reduced linkage drag, the invention also encompasses seeds or descendants of these plants, wherein these comprise the defined chromosomal segment or the at least one defined nucleic acid molecule for the restoration property. Descendants also exhibit the improved restoration property without linkage drag or with reduced linkage drag. Furthermore, organs, parts, tissues or cells of the plant are provided which have the restoration property inherent in them.

The invention also concerns an oligonucleotide, preferably with a maximum length of 50 nucleotides, which has one of the following nucleotide sequences: (i) SEQ ID NOs: 4, 6, 8, 10, 12, 14, 16, 18 or a complement thereof, or (ii) SEQ ID NOs: 5, 7, 9, 11, 13, 15, 17, 19 or a complement thereof. Such oligonucleotides, when used as molecular markers or molecular markers based on such oligonucleotides, are also encompassed by the present invention. Such molecular markers which detect the presence of absence of a marker locus of the donor are, for example, based on a SNP (examples: KASPar or TaqMan markers).

The improvements described above to the chromosomal segment in accordance with the invention which, for example, originates from the donor IRAN IX, come exclusively from the comprehensive and sophisticated development and penetration of the chromosomal segment with molecular markers which are close-coupled to the restoration locus for P-CMS (see markers described above as well as Table 2) and the flanking regions, which presumably carry the agronomically disadvantageous genes (linkage drag). In addition, a fundamental prerequisite is that the markers are suitable for high throughput screening. In the context of the present invention, the production, identification and evaluation of recombinants has been carried out for the first time, although, because of the large genetic distance between the central European elite populations as recipients of the chromosomal segment and the Iranian or Argentinian donor population, the recombination frequency is extraordinarily low. These difficulties are known to the person skilled in the art from the literature (Ruge B, Linz A, Pickering R, Proeseler G, Greif P, Wehling P (2003) Mapping of Rym14$^{Hb}$, a gene introgressed from *Hordeum bulbosum* and conferring resistance to BaMMV and BaYMV in barley. Theor Appl Genet 107:965-971).

In addition to the extraordinary advance in the field of genotyping the Rfp1 target region, the present invention also enabled a novel highly diagnostic phenotyping system to be developed. The "Near Isogenic Bulk (NIB)" phenotyping tests (see Example 1 and 2) have for the first time enabled a reliable determination of the linkage drag effect to be made with the required precision, as only in this manner could the linkage drag effect be phenotypically separated from the effects of the genetic background. In this regard, linkage drag effects could be calculated as a difference ($\Delta_{E-D}$) between test crossing means from NIB partners which carry the elite allele (E) and corresponding NIB partners which carry the donor allele (D) for all markers in the chromosomal interval (see also FIG. 2).

In a further aspect, the present invention concerns a method for producing a plant, in particular from the gramineous order (Poales), preferably from the sweet grass family (Poaceae), which is suitable, as a male pollen parent, for restoring the pollen fertility for the P-CMS wherein, in a hybrid plant from a cross with a female CMS parent, a linkage drag otherwise coupled with the restoration property, preferably a yield-reducing effect, is reduced or completely eliminated. Such a method comprises the following step: removal of one or more chromosomal intervals which contain one or more of the following marker loci of the donor: 7_01_H_1441, ctg24met2a5 or ctg32, from the genome of a plant, preferably from chromosome 4R, wherein the inventive chromosomal segment with the Rfp1a gene and/or Rfp1b gene (see also FIG. 1) as described above remains. As an example, the removal of one or more chromosomal intervals may be carried out by genetic recombination during a crossing process between two plants, wherein one plant carries the known Rfp1 locus heterozygously. This conventional breeding technique for the production of a genetic recombination leads to the result that at least one of the donor intervals identified above with linkage drag is replaced by genomic sequences from the recurrent parent which is preferably free from unwanted genes. In this regard, removal may comprise the following steps: (I) crossing a first plant, comprising the restoration locus from a donor selected from the group consisting of IRAN IX, Pico Gentario and Altevogt 14160, with a second plant which does not have this restoration locus; (II) selecting descendants which have the inventive chromosomal segment as described above. Preferably, the selection is marker-based; suitable markers are accessible to the person skilled in the art through the present disclosure. This marker-based selection of the restorer genes can contribute considerably to accelerating the breeding process, because the desired information about the presence of the restorer gene can be acquired early on and without complicated test crossings.

In this regard, the present invention also encompasses a method for detecting a plant, in particular from the gramineous order (Poales), preferably from the sweet grass family (Poaceae), which is suitable, as a male pollen parent, for restoring the pollen fertility for the P-CMS wherein, in a hybrid plant from a cross with a female CMS parent, a linkage drag otherwise coupled with the restoration property, preferably a yield-reducing effect, is reduced or completely eliminated. This method comprises detecting, in the plant, alleles from at least two markers originating from a donor selected from the group consisting of IRAN IX, Pico Gentario and Altevogt 14160, wherein at least one marker is localized on or in the chromosomal interval between tc256739 and ctg2 and at least one marker is localized on or in the chromosomal interval between ctg16b and tc300731, or wherein at least one marker is localized on or in the chromosomal interval between tc256739 and c40745_1 and at least one marker is localized on or in the chromosomal interval between 7_01_H_1441 and tc300731, Alternatively, the method comprises the detection in the plant of the presence or absence of at least one marker allele originating from a donor selected from the group consisting of IRAN IX, Pico Gentario and Altevogt 14160, on or in the Rfp1 locus, and selection of plants in which the at least one marker allele is present. Preferably, the Rfp1 locus means a chromosomal section between the marker loci tc256739, ctg32 or ctg24met2a5 and tc300731 or 7_01_H_1441 on chromosome 4R from a donor selected from the group consisting of IRAN IX, Pico Gentario and Altevogt 14160. The Rfp1 locus may, for example, be one of the following sections: between the marker loci tc256739 and tc300731, between the marker loci ctg32 and tc300731, between the marker loci ctg24met2a5 and tc300731, between the marker loci ctg2 and tc300731, between the marker loci ctg16b and tc300731, between the marker loci c40745_1 and tc300731, between the marker loci P20 and tc300731, between the marker loci tc256739 and 7_01_H_1441, between the marker loci ctg32 and 7_01_H_1441, between the marker loci ctg24met2a5 and 7_01_H_1441, between the marker loci ctg2 and 7_01_H_1441, between the marker loci ctg16b and 7_01_H_1441, between the marker loci c40745_1 and 7_01_H_1441, between the marker loci P20 and 7_01_H_1441, between the marker loci tc256739 and 72F13_c2_mTERF, between the marker loci tc256739 and P20, between the marker loci tc256739 and c40745_1, between the marker loci tc256739 and ctg16b, between the marker loci ctg32 and 72F13_c2_mTERF, between the marker loci ctg32 and P20, between the marker loci ctg32 and c40745_1, between the marker loci ctg32 and ctg16b, between the marker loci ctg24met2a5 and 72F13_c2_mTERF, between the marker loci ctg24met2a5 and P20, between the marker loci ctg24met2a5 and c40745_1, between the marker loci ctg24met2a5 and ctg16b, between the marker loci ctg2 and 72F13_c2_mTERF, between the marker loci ctg2 and P20, between the marker loci ctg2 and c40745_1 or between the marker loci ctg2 and ctg16b. As an example, for the detection, one or more of the following oligonucleotides which has one of the following nucleotide sequences may be used as a marker: (i) SEQ ID NOs: 4, 6, 8, 10, 12, 14, 16, 18 or a complement thereof, or (ii) SEQ ID NOs: 5, 7, 9, 11, 13, 15, 17, 19 or a complement thereof. In the context of the present invention, by means of the markers described above, recombinant genotypes have been identified and the respective remaining introgression segment has been described: see Example 3. As can be seen in Example 3, the marker P20 plays the most important role in the identification and description, because using it, further marker sequences could be identified and a plurality of marker combinations could be designed; see Table 2 and Example 6.

Alternatively, modern biotechnology offers the person skilled in the art a variety of further tools which enable precise genome engineering to be carried out: genetic engineering approaches with the aid of which the elimination of linkage drag-carrying nucleotide sequences from a plant genome can be supported or directly obtained, comprise the use of TALE nucleases (TALENs) or zinc finger nucleases (ZFNs) as well as CRISPR/Cas systems which, inter alia, have been described by way of example in German patent document DE 10 2013 014 637 for the elimination of linkage drag-carrying nucleotide sequences from the genome of *Helminthosporium turcicum*-resistant (hybrid) maize; see DE 10 2013 014 637 on pages 13 and 14 in paragraphs [0038] to [0042] and the references cited therein. These techniques, which are also described in international patent application WO 2014/104878, may be used in an equivalent manner in the production of the present plants in accordance with the invention.

The present invention also encompasses a combination of the conventional breeding technique and modern biotechnology. Thus, for example, with the aid of this novel genome editing approach, recombination "hot spots" can be produced in a plant which occur at suitable sites for directly promoting the removal of linkage drag. Thus, the present invention provides the person skilled in the art with the necessary information regarding localization of the linkage drag as well as the position of the restoration gene/restoration genes.

Furthermore, the novel genome editing approaches also allow for direct introduction of the chromosomal segment in accordance with the invention with reduced or entirely eliminated linkage drag. In this regard, this invention also encompasses a further method for the production of a plant in accordance with the invention, in particular from the gramineous order (*Poales*), preferably from the sweet grass family (*Poaceae*), which is suitable, as a male pollen parent, for restoring the pollen fertility for the Pampa cytoplasmic male sterility (CMS) wherein, in a hybrid plant from a cross with a female CMS parent, a linkage drag otherwise coupled with the restoration property, preferably a yield-reducing effect, is reduced or completely eliminated. Such a method comprises the following steps: (I) providing a portion of a plant which preferably does not carry the restoration locus of the present invention, as the target structure containing the target nucleic acid region, preferably a genomic DNA which corresponds to the chromosomal positioning of that of the Rfp1 locus; (II) providing one or more recombinant constructs which together comprise or code for the components of the genome editing tool; (III) providing at least one vector for introducing the recombinant construct/constructs; (IV) providing at least one further recombinant construct comprising the inventively defined nucleic acid molecule, the recombinant DNA, the expression cassette or the chromosomal segment for targeted homology-directed repair of the target nucleic acid region in the target plant structure or insertion into the target nucleic acid region in the target plant structure; (V) introducing the recombinant constructs from (II) and (IV) into the target plant structure; (VI) cultivating the target plant structure under conditions which activate the components of the genome editing tool and thereby allow a targeted modification to be carried out in the target nucleic acid region in the target plant structure, in order to obtain a target plant structure comprising at least one cell which comprises the targeted modification of the target nucleic acid region; and (VII) regenerating a plant from the at least one cell.

In a further aspect, the present invention concerns a method for the production of an inventive hybrid plant, preferably from the gramineous order (Poales), particularly preferably from the sweet grass family (*Poaceae*) or from the genus *Secale* or *Hordeum* and more particularly preferably from the species *Secale cereale* or *Hordeum vulgare*. This method comprises, in a first step (1), the method for the production of a plant which is capable, as a male pollen parent, of restoring the pollen fertility for the Pampa cytoplasmic male sterility (CMS), as defined in the preceding paragraphs. In a further step (2) of this method, the plant produced in step (1) or a descendant thereof, which still comprises the inventive chromosomal segment or the inventive nucleic acid molecule, is crossed as a male pollen parent with a female CMS parent, preferably from the same species. In this case, the male pollen parent and/or the female CMS parent is preferably a double haploid plant, an inbred plant, a CMS single cross or what is known as a pollen parent synthetic. In a step (3), the hybrid seed is harvested from the female CMS parent. An optional step (4) comprises sowing the hybrid seed in order to produce the hybrid plant and further optional steps (5) comprise harvesting the seed from the hybrid plant and (6) sowing the seed from the hybrid plant. Furthermore, the present invention encompasses seed or seeds and plants or hybrid plants which are obtained or can be obtained using the above method.

In a further aspect, the present invention also concerns nucleic acid molecule which is suitable for mediating the restoration property with reduced or completely eliminated linkage drag, wherein the nucleic acid molecule comprises a nucleotide sequence which is selected from the group consisting of: (i) a nucleotide sequence with one of SEQ ID NO: 1 or SEQ ID NO: 28 or a functional fragment thereof, (ii) a nucleotide sequence which codes for an amino acid sequence with one of SEQ ID NO: 2 or SEQ ID NO: 29 or a functional fragment thereof, (iii) a nucleotide sequence which is complementary to a nucleotide sequence in accordance with (i) or (ii), (iv) a nucleotide sequence which hybridizes with a sequence in accordance with (iii) under stringent conditions, (v) a nucleotide sequence which has an identity of at least 70%, 75%, 80%, 85% or 90%, preferably of at least 91%, 92%, 93% 94% or 95%, or particularly preferably of at least 96%, 97%, 98%, 99% or 99.5% with the nucleotide sequence in accordance with (i) or (ii), (vi) a nucleotide sequence which codes for an amino acid sequence which has an identity of at least 65%, 70%, 75%, 80%, 85% or 90%, preferably of at least 91%, 92%, 93% 94% or 95%, or particularly preferably of at least 96%, 97%, 98%, 99% or 99.5% with the SEQ ID NO: 2 or a functional fragment thereof, (vii) a nucleotide sequence which codes for an amino acid sequence which, compared with the amino acid sequence shown in SEQ ID NO: 2 or SEQ ID NO: 29, exhibits discrepancies in the amino acid sequence in the form of amino acid deletions, substitutions, additions and/or insertions in the amino acid sequence, preferably of no more than 30%, 25% or 20%, preferably no more than 18%, 16%, 14%, 12% or 10% or particularly preferably no more than 9%, 8%, 7%, 6%, 5%, 4%, 3%, 2%, 1% or 0.5% over the entire amino acid sequence. Because of the exact identification and fine mapping of the restoration property of the restorer locus Rfp1, it is also possible to use the nucleic acid molecule defined above in other ways in order to obtain the improved properties of the plant. For this reason, the present invention also encompasses an expression cassette, recombinant DNA or vectors which each comprise the nucleic acid molecule.

In one embodiment, the nucleic acid molecule is comprised by a recombinant DNA. In this case, as a rule, a promoter and/or other transcription or translation control elements will be included in it or associated with it. The promoters used will primarily be promoters which allow transcription of the DNA only in prescribed cells. In addition to the promoters, there are a plurality of further transcription control elements such as, for example, enhancers, operators, repressors and transcription termination signals, although this is not limiting, which are functionally connected to the DNA, in order to produce a targeted cell-specific transcription. Promoters and other transcription regulation elements are generally known and accessible to the person skilled in the art in the prior art; see, for example, WO 00/75359 on page 23, line 5 to page 24, line 17.

The vector may be a plasmid, a cosmid, a phage or an expression vector, a transformation vector, shuttle vector or cloning vector; it may be double or single-stranded, linear or circular, or it may transform a prokaryotic or eukaryotic host either by integration into its genome or extrachromosomally. Preferably, the nucleic acid molecule in accordance with the invention is operatively connected to one or more regulatory sequences which allow the transcription and, optionally, expression in a prokaryotic or eukaryotic host cell; see, for example, Sambrook et al., Molecular Cloning: A Laboratory Manual 3rd Ed. Cold Spring Harbor Laboratory Press. Cold Spring Harbor, NY, 2001 and the international application WO 00/75359 on page 21, line 20 to page 22, line 32. A regulatory sequence, preferably DNA, may be homologous or heterologous to the nucleic acid in accordance with the invention. The nucleic acid may, for example, be under the control of a suitable promoter or a terminator. Suitable promoters may be promoters which are constitutively induced (for example: 35S promoter from the "Cauliflower mosaic virus" (Odell et al. 1985), which are tissue-specific, stress-specific or development-specific (for example: anther-specific expression). Suitable promoters may also be synthetic or chimeric promoters which do not occur in nature, composed of a plurality of elements and containing a minimal promoter as well as at least one cis-regulatory element upstream of the minimal promoter which acts as a binding site for special transcription factors. Chimeric promoters can be designed to desired specifications and are induced or re-primed by various factors. Examples of such promoters can be found in Gurr & Rushton (Gurr, S J; Rushton, P J. Engineering plants with increased disease resistance: what are we going to express? Trends in Biotechnology, 2005, 23. Jg., No. 6, p. 275-282) or Venter (Synthetic promoters: genetic control through cis engineering. Trends in Plant Science, 2007, 12. Jg., No. 3, p. 118-124). An example of a suitable terminator is the nos-terminator (Depicker, A, Stachel, S, Dhaese, P, Zambryski, P and Goodman, H (1982) J. Mol. Appl. Genet., 1, 561-575).

In addition to the vectors described above, the present invention also provides a method which comprises introducing the described vector into a host cell. The vector may, for example, be introduced by conjugation, mobilization, biolistic transformation, *agrobacterium*-induced transformation, transfection, transduction, vacuum filtration or electroporation. Such methods as well as methods for the preparation of the described vectors are familiar to the person skilled in the art (Sambrook et al. 2001, Molecular cloning: a laboratory manual (3-volume set) (Vol. 999). Cold Spring Harbor, New York: Cold Spring Harbor Laboratory Press). Furthermore, the prior art contains various methods by means of which transgenic plants can be produced and the restoration trait can be introduced. These include direct and indirect methods. The methods encompass particle bombardment (Weeks et al. Plant Physiol. 102, (1993) 1077-1084; Vasil et al., Bio/Technology 10 (1992), 662-674), *agrobacterium* transformation (Chan et al., Plant Mol. Biol. 22 (1993), 491-506), electroporation of regeneratable tissue (Shillito et al. 1985 "High efficiency direct gene transfer to plants." *Nature Biotechnology* 3.12: 1099-1103), silicon carbide-mediated gene transfer (Dalton et al., Plant Sci. 132 (1998), 31-43) and protoplast-mediated gene transfer (Shimamoto et al., Nature, 338 (1989), 274-276), biolistic or *agrobacterium*-mediated gene transfer (WO 01/73084). Introduction of the restoration trait may also be carried out by introgression (Harper et al., Annals of Botany 107: (2011), 1313-1320) or also by means of a genetic engineering strategy. Many novel genetic engineering methods for introducing DNA and also for inactivating genomic sequences are known to the person skilled in the art (for example the genome editing method based zinc finger nucleases, TALENs or on a CRISPR/Cas system).

Alternatively or in addition, the present invention also concerns host cells which comprise the nucleic acid molecule as a transgene, expression cassette, recombinant DNA as a transgene or the vector as described above. A "host cell" in the context of the invention may be a prokaryotic (for example bacterial) or eukaryotic cell (for example a plant cell or a yeast cell). Preferably, the host cell is an *agrobacterium* such as *Agrobacterium tumefaciens* or *Agrobacterium rhizogenes* or a plant cell which comprises the nucleic acid molecule, the expression cassette, the recombinant DNA or the vector of the present invention. The person skilled in the art will be aware of both many methods such as conjugation or electroporation, with which the nucleic acid molecule, the expression cassette, the recombinant DNA or the vector of the present invention can be introduced into an *agrobacterium*, as well as methods such as various transformation methods (biolistic transformation, *agrobacterium*-mediated transformation), with which the nucleic acid molecule, the expression cassette, the recombinant DNA or the vector of the present invention can be introduced into a plant cell (Sambrook et al. 2001).

By identifying the restoration mediating genes, it is also possible to use it in transgenic plants wherein linkage drag associated with them can be reduced to a minimum. In this manner, the invention also encompasses the provision of a transgenic plant or seeds thereof which comprise a plant cell as defined above. An example of such a transgenic plant cell or plant is a plant cell or plant which is transformed, preferably in a stable manner, with the inventive nucleic acid molecule, with the expression cassette, with the recombinant DNA or with the vector of the present invention. The transgenic plant has a newly-mediated restoration property for pollen fertility for the Pampa cytoplasmic male sterility (CMS) or an improved restoration property for the pollen fertility for the Pampa cytoplasmic male sterility (CMS) compared with a wild type plant which is isogenic but does not have the inventive nucleic acid molecule, with the expression cassette, with the recombinant DNA or with the vector of the present invention. Preferably, these transgenic plants additionally have a newly-mediated resistance to a pathogen, preferably to a fungus, in particular to the fungus *Claviceps purpurea* (Fr.), or an enhanced resistance to a pathogen, preferably to a fungus, in particular to the fungus *Claviceps purpurea* (Fr.), compared with a wild type plant which is isogenic, but not transformed with the inventive nucleic acid molecule, with the expression cassette, with the recombinant DNA or with the vector of the present invention, preferably in a stable manner.

In addition to the nucleic acid molecule which codes for the restoration property with reduced or completely eliminated linkage drag, the present invention further concerns an mTERF protein or homologue, analogue, orthologue or a functional fragment thereof which can be coded by the nucleic acid molecule as well as an antibody which specifically binds to the mTERF protein or homologue, analogue, orthologue or a functional fragment thereof. The mTERF protein preferably comprises an amino acid sequence with one of SEQ ID NO: 2 or SEQ ID NO: 29 or an amino acid sequence which has an identity of at least 65%, 70%, 75%, 80%, 85% or 90%, preferably of at least 91%, 92%, 93% 94% or 95%, or particularly preferably of at least 96%, 97%, 98%, 99% or 99.5% with the SEQ ID NO: 2 or SEQ ID NO: 29. Furthermore, the present invention also concerns an antibody which specifically binds to the mTERF protein. The recombinant production of proteins and functional fragments thereof is familiar to the person skilled in the art and has been described, for example, in Sambrook et al. (Molecular Cloning: A Laboratory Manual 3rd Ed. Cold Spring Harbor Laboratory Press. Cold Spring Harbor, NY, 2001 Wingfield, P. T. 2008. Production of Recombinant proteins. Current Protocols in Protein Science. 52:5.0:5.0.1-5.0.4). Polyclonal or monoclonal antibodies to the protein of the present invention may be produced by the person skilled in the art using known methods such as those described by E. Harlow et al. (Antibodies: A Laboratory Manual (1988)). The production of monoclonal antibodies as well as of Fab- and F(ab')$_2$ fragments, which are also useful in protein detection methods, may be carried out using various conventional methods as described by Goding (Mononoclonal Antibodies: Principles and Practice, p. 98-118, New York: Academic Press (1983)).

The use of antibodies for the production and selection of hybrid plants or transgenic plants with an enhanced yield have, for example, been described in the international patent application WO 2011/061656 in paragraphs [00678] and [00847] and the references cited therein. These techniques may equally be used in the production of the plants of the present invention.

In a further aspect, the present invention provides a method for producing a plant, in particular from the gramineous order (Poales), which is suitable, as a male pollen parent, for restoring the pollen fertility for the Pampa cytoplasmic male sterility (CMS). Such a method comprises the following steps: A) mutagenizing plant cells or portions of a plant and subsequently regenerating plants from the mutated plant cells or mutagenized portions or mutagenizing plants, and B) identifying a plant from A) which comprises an endogenous DNA sequence which is identical to a nucleic acid sequence selected from the group consisting of: (i) the nucleotide sequence with one of SEQ ID NO: 1 or SEQ ID NO: 28 or a functional fragment thereof, (ii) the nucleotide sequence which codes for an amino acid sequence with one of SEQ ID NO: 2 or SEQ ID NO: 29 or a functional fragment thereof, (iii) the nucleotide sequence which is complementary to a nucleotide sequence in accordance with (i) or (ii), (iv) the nucleotide sequence which hybridizes with a sequence in accordance with (iii) under stringent conditions, (v) the nucleotide sequence which has an identity of at least 70%, 75%, 80%, 85% or 90%, preferably of at least 91%, 92%, 93% 94% or 95%, or particularly preferably of at least 96%, 97%, 98%, 99% or 99.5% with the nucleotide sequence in accordance with (i) or (ii), (vi) the nucleotide sequence which codes for an amino acid sequence which has an identity of at least 65%, 70%, 75%, 80%, 85% or 90%, preferably of at least 91%, 92%, 93% 94% or 95%, or particularly preferably of at least 96%, 97%, 98%, 99% or 99.5% with SEQ ID NO: 2 or a functional fragment thereof, (vii) the nucleotide sequence which codes for an amino acid sequence which, compared with the amino acid sequence shown in SEQ ID NO: 2 or SEQ ID NO: 29, exhibits discrepancies in the amino acid sequence in the form of amino acid deletions, substitutions, additions and/or insertions in the amino acid sequence, preferably by no more than 30%, 25% or 20%, preferably no more than 18%, 16%, 14%, 12% or 10% or particularly preferably no more than 9%, 8%, 7%, 6%, 5%, 4%, 3%, 2%, 1% or 0.5% over the entire amino acid sequence, or which has at least one mutation in a regulatory sequence of the endogenous DNA sequence which acts so that the identified plant has a newly-mediated restoration property for the pollen fertility for the Pampa cytoplasmic male sterility (CMS) or an improved restoration property for the pollen fertility for the Pampa cytoplasmic male sterility (CMS) compared with a non-mutated wild type plant which is otherwise isogenic and/or which has a newly-mediated resistance against a pathogen, preferably against a fungus, in particular against the fungus *Claviceps purpurea* (Fr.), or an enhanced resistance against a pathogen, preferably against a fungus, in particular against the fungus *Claviceps purpurea* (Fr.) compared with a non-mutated wild type plant which is otherwise isogenic.

Preferably, the endogenous DNA sequence from step B) codes for an mTERF protein, particularly preferably for the mTERF protein with one of SEQ ID NOs: 2 or SEQ ID NO: 29 or a homologue, analogue or orthologue thereof. Preferably, the regulatory sequence of the endogenous DNA sequence from step B) is a promoter or a portion thereof. An example of a regulatory sequence of the endogenous DNA sequence is the promoter with SEQ ID NO: 3.

A "mutation" means a modification on a DNA level, i.e. a change in the genetics and/or epigenetics. As an example, a modification in the genetics may be the exchange of at least one nucleobase in the endogenous DNA sequence or in a regulatory sequence of the endogenous DNA sequence. If such a nucleobase exchange occurs, for example in a promoter, then this may result in a modified activity of the promoter because, for example, cis-regulatory elements are modified in a manner such that the affinity of a transcription factor to the mutated cis-regulatory element is modified compared with the wild type promoter, so that the activity of the promoter with the mutated cis-regulatory element is raised or reduced, depending on whether the transcription factor is a repressor or inductor or whether the affinity of the transcription factor to the mutated cis-regulatory element is strengthened or weakened. If such a nucleobase exchange occurs, for example in a coding region or the endogenous DNA sequence, this may lead to an amino acid exchange in the encoded protein, which may result in an alteration in the activity or stability of the protein compared with the wild type protein. Possible amino acid exchanges can be discerned by comparing the amino acid sequences. FIG. 9 shows a comparison of the wild type sequence of rfp1a (SEQ ID NO: 33) with that of the restoration property-mediating amino acid sequence from IRAN9 (SEQ ID NO: 29). As an example, the following potential amino acid exchanges may be derived: in position 10 of SEQ ID NO: 29, at which the restoration property-mediating mTERF protein comprises an alanine (A) and a corresponding (non-restoring protein) from the wild type (SEQ ID NO: 33) comprises a threonine (T), at position 18 of SEQ ID NO: 29, at which the restoration property-mediating mTERF protein comprises a proline (P) and a corresponding (non-restoring protein) from the wild type (SEQ ID NO: 33) comprises a threonine (T), at position 43 of SEQ ID NO: 29, at which the restoration property-mediating mTERF protein comprises a glutamine (Q) and a corresponding (non-restoring protein) from the wild type (SEQ ID NO: 33) comprises an aspartic acid (D), at position 45 of SEQ ID NO: 29, at which the restoration property-mediating mTERF protein comprises a glutamic acid (E) and a corresponding (non-restoring protein) from the wild type (SEQ ID NO: 33) comprises an aspartic acid (D), at position 62 of SEQ ID NO: 29, at which the restoration property-mediating mTERF protein comprises a threonine (T) and a corresponding (non-restoring protein) from the wild type (SEQ ID NO: 33) comprises an alanine (A), at position 63 of SEQ ID NO: 29, at which the restoration property-mediating mTERF protein comprises an alanine (A) and a corresponding (non-restoring protein) from the wild type (SEQ ID NO: 33) comprises a threonine (T), at position 108 of SEQ ID NO: 29, at which the restoration property-mediating mTERF protein comprises a glutamic acid (E) and a corresponding (non-restoring protein) from the wild type (SEQ ID NO: 33) comprises an aspartic acid (D), at position 126 of SEQ ID NO: 29, at which the restoration property-mediating mTERF protein comprises a serine (S) and a corresponding (non-restoring protein) from the wild type (SEQ ID NO: 33) comprises an alanine (A), at position 193 of SEQ ID NO: 29, at which the restoration property-mediating mTERF protein comprises an aspartic acid (D) and a corresponding (non-restoring protein) from the wild type (SEQ ID NO: 33) comprises a glycine (G), at position 213 of SEQ ID NO: 29, at which the restoration property-mediating mTERF protein comprises a glycine (G) and a corresponding (non-restoring protein) from the wild type (SEQ ID NO: 33) comprises a glutamic acid (E), at position 243 of SEQ ID NO: 29, at which the restoration property-mediating mTERF protein comprises a serine (S) and a corresponding (non-restoring protein) from the wild type (SEQ ID NO: 33) comprises a cysteine (C), at position 272 of SEQ ID NO: 29, at which the restoration property-mediating mTERF protein comprises a cysteine (C) and a corresponding (non-restoring protein) from the wild type (SEQ ID NO: 33) comprises an arginine (R), at position 276 of SEQ ID NO: 29, at which the restoration property-mediating mTERF protein comprises an alanine (A) and a corresponding (non-restoring protein) from the wild type (SEQ ID NO: 33) comprises a threonine (T), at position 303 of SEQ ID NO: 29, at which the restoration property-mediating mTERF protein comprises an isoleucine (I) and a corresponding (non-restoring protein) from the wild type (SEQ ID NO: 33) comprises a valine (V), at position 363 of SEQ ID NO: 29, at which the restoration property-mediating mTERF protein comprises an alanine (A) and a corresponding (non-restoring protein) from the wild type (SEQ ID NO: 33) comprises a valine (V), or at position 365 of SEQ ID NO: 29, at which the restoration property-mediating mTERF protein comprises a histidine (H) and a corresponding (non-restoring protein) from the wild type (SEQ ID NO: 33) comprises an arginine (R). In an analogous manner, potential amino acid exchanges may also be deduced from FIG. 10, which shows a comparison of the wild type amino acid sequences of rfp1b (SEQ ID NO: 31) with that of the restoration property-mediating amino acid sequence from IRAN9 (SEQ ID NO: 2). Further potential mutations as modifications on a DNA level (for example in the form of nucleotide exchanges or insertions/deletions) may also be deduced in an analogous manner from comparisons of the coding nucleotide sequences of rfp1a and rfp1b in FIGS. 7 and 8.

A further example of a modification in the genetics is the deletion of nucleotides in the regulatory sequence and/or the endogenous DNA sequence as well as the addition of nucleotides in the regulatory sequence and/or in the endogenous DNA sequence. An example of the regulation of genes by insertion of nucleotides by means of transposon mutagenesis in maize is shown by Das & Martienssen (Das, Lekha, and Robert Martienssen. "Site-selected transposon mutagenesis at the hcf106 locus in maize." The Plant Cell 7.3 (1995): 287-294.). A modification to the epigenetics may, for example, be accomplished by means of a modified methylation pattern for the DNA.

The person skilled in the art is aware how a "mutation" within the meaning of the invention can be obtained by means of the mutagenization process in step A) of the method for the production of a plant cell/plant. The mutagenization here includes both conventional mutagenesis and also site-specific mutagenesis or "genome editing". In conventional mutagenesis, a modification on the DNA level is not carried out in a targeted manner. The plant cell or plant is exposed to mutagenetic conditions such as, for example, by TILLING using UV light irradiation or using chemical materials (Till, Bradley J., et al. "Discovery of induced point mutations in maize genes by TILLING." BMC Plant Biology 4.1 (2004): 12.). A further method for carrying out random mutagenesis is mutagenesis with the aid of a transposon.

Site-specific mutagenesis enables modifications on a DNA level to be deliberately introduced to predetermined sites in the DNA. Examples which may be used in this regard are TALENS (WO 2010/079430, WO 2011/072246), meganucleases (Silva, George, et al. "Meganucleases and other tools for targeted genome engineering: perspectives and challenges for gene therapy." Current gene therapy 11.1 (2011): 11.), homing endonucleases (Stoddard, Barry L. "Homing endonucleases: from microbial genetic invaders to reagents for targeted DNA modification." Structure 19.1 (2011): 7-15.), zinc finger nucleases (Lloyd, Alan, et al. "Targeted mutagenesis using zinc-finger nucleases in *Arabidopsis*." Proceedings of the National Academy of Sciences of the United States of America 102.6 (2005): 2232-2237), or a CRISPR/Cas-system (Gaj, Thomas, Charles A. Gersbach, and Carlos F. Barbas. "ZFN, TALEN, and CRISPR/Cas-based methods for genome engineering." Trends in biotechnology 31.7 (2013): 397-405.). As an example, the mutation occurs in all copies or alleles or where appropriate in all homologues of the corresponding endogenous DNA sequences. In respect of a diploid organism such as, for example, *Secale cereale* or *Hordeum vulgare*, this may typically mean at least two modifications.

The identification of a plant in step B) may, for example, be carried out with the aid of molecular markers or probes. DNA probes are, for example, primers or primer pairs which can be used in a PCR reaction. As an example, Tilling mutants can be detected or identified by sequencing the target gene in a TILLING population or other methods which detect mispairing in the DNA such as, for example, melting point analyses or the use of mispairing-specific nucleases. Thus, the present invention encompasses primer/primer pairs, such as primers for detecting mTERF or a mutated form thereof. Furthermore, mutants produced by means of transposons may be detected by using transposon-specific primers and target gene-specific primers in the PCR over the whole population and subsequent sequencing of PCR products, Such primers are also encompassed by the present invention. Mutation-determined modification of the expression rate or the degree of expression may, for example, be determined using RT-PCR in plant tissues, a mutation-determined modification to the stability by testing with ubiquitin binding sites, for example, and predicting modifications in the tertiary structure. Furthermore, recombinant expression of the wild type proteins and the corresponding mutated proteins and biochemical activity tests are suitable. The person skilled in the art will be aware of other methods and means in the prior art which can be used to identify a plant or plant cell in step B).

The present invention also concerns molecular markers which detect the presence or absence of a mutation in the endogenous DNA sequence or in a regulatory sequence of the endogenous DNA sequence. Such markers are based, for example, on an SNP and are specific for the mutation (examples: KASP or TaqMan marker). Examples of suitable SNPs for marker development for *Secale cereale* can be found in the sequence comparison of FIGS. 7 and 8.

The present invention also concerns a plant which can be produced or is produced by the present method, or a portion of this plant. Similarly, the present invention also encompasses a descendant of the plant which has the at least one mutation and thus a newly-mediated restoration property for the pollen fertility for the Pampa cytoplasmic male sterility (CMS) or an improved restoration property for the pollen fertility for the Pampa cytoplasmic male sterility (CMS) compared with a non-mutated wild type plant which is otherwise isogenic, and/or which has a newly-mediated resistance against a pathogen, preferably against a fungus, in particular against the fungus *Claviceps purpurea* (Fr.), or an enhanced resistance against a pathogen, preferably against a fungus, in particular against the fungus *Claviceps purpurea* (Fr.) compared with a non-mutated wild type plant which is otherwise isogenic.

In a farther aspect, the present invention provides a method for producing a transgenic plant which has a newly-mediated restoration property for the pollen fertility for the Pampa cytoplasmic male sterility (CMS) or an improved restoration property for the pollen fertility for the Pampa cytoplasmic male sterility (CMS) compared with a non-mutated wild type plant which is otherwise isogenic, and/or which has a newly-mediated resistance against a pathogen, preferably against a fungus, in particular against the fungus *Claviceps purpurea* (Fr.), or an enhanced resistance against a pathogen, preferably against a fungus, in particular against the fungus *Claviceps purpurea* (Fr.) compared with a non-mutated wild type plant which is otherwise isogenic. The method may comprise the following steps: A) providing the nucleic acid molecules, the expression cassette or the recombinant DNA described above, or providing the vector described above, B) transformation, preferably stable transformation, of at least one plant cell by introducing the nucleic acid molecule, the expression cassette, the recombinant DNA or the vector from A), C) regenerating transgenic plants from the at least one transformed plant cell from B), and optionally D) identification of a plant which has a newly-mediated restoration property for the pollen fertility for the Pampa cytoplasmic male sterility (CMS) or an improved restoration property for the pollen fertility for the Pampa cytoplasmic male sterility (CMS) compared with a non-mutated wild type plant which is otherwise isogenic, and/or which has a newly-mediated resistance against a pathogen, preferably against a fungus, in particular against the fungus *Claviceps purpurea* (Fr.), or an enhanced resistance against a pathogen, preferably against a fungus, in particular against the fungus *Claviceps purpurea* (Fr.) compared with a non-mutated wild type plant which is otherwise isogenic, from C). The method for the production of the transgenic plant also encompasses the provision of two or more of the nucleic acid molecules described above, optionally also different embodiments of the nucleic acid molecule in accordance with the invention and optionally in one or more expression cassettes or vectors, and transformation of plant cells by introduction of the two or more nucleic acid molecules.

The present invention also concerns a transgenic plant which can be produced or is produced using said method, or a portion of this plant. Similarly, the present invention also encompasses a descendant of the transgenic plant which has a newly-mediated restoration property for the pollen fertility for the Pampa cytoplasmic male sterility (CMS) or an improved restoration property for the pollen fertility for the Pampa cytoplasmic male sterility (CMS) compared with a non-mutated wild type plant which is otherwise isogenic, and/or which has a newly-mediated resistance against a pathogen, preferably against a fungus, in particular against the fungus *Claviceps purpurea* (Fr.), or an enhanced resistance against a pathogen, preferably against a fungus, in particular against the fungus *Claviceps purpurea* (Fr.) compared with a non-mutated wild type plant which is otherwise isogenic.

In a further aspect, the present invention concerns a method for mediating or increasing the restoration property for the pollen fertility for the Pampa cytoplasmic male sterility (CMS) in a plant cell or a plant and/or for mediating or increasing the resistance against a pathogen, preferably against a fungus, in particular against the fungus *Claviceps purpurea* (Fr.). Such a method may comprise the following steps: A) transformation, preferably stable transformation, of at least one plant cell by introducing the inventive nucleic acid molecules, the recombinant DNA or the expression cassette of the present invention described above, or the vector of the present invention described above, optionally B) regenerating transgenic plants from the at least one transformed plant cell from A). The method for the production of the transgenic plant cell/plant also encompasses the transformation of two or more of the inventive nucleic acid molecules described above, optionally also different embodiments of the inventive nucleic acid molecule and optionally one or more expression cassettes or vectors of the present invention.

Furthermore, the present invention concerns the use of the plant described above, the descendant described above or said transgenic plant for the production of a hybrid plant in accordance with the invention or a transgenic plant in accordance with the invention, preferably from the genus *Secale* or *Triticale*, preferably a plant of the species *Secale cereale*, in which its pollen fertility for the Pampa CMS has been restored and/or which has an enhanced resistance against a fungal pathogen, in particular against the fungus *Claviceps purpurea* (Fr.).

Furthermore, the entities described above such as oligonucleotides, nucleic acids, expression cassettes, recombinant DNA, vectors and antibodies may also be of use in the production of the plant or the transgenic plant. In this regard, the present invention also encompasses the use of the oligonucleotide described above, the nucleic acid molecule, the recombinant DNA, the vector or the antibody in the production of a hybrid plant in accordance with the invention or of a transgenic plant in accordance with the invention. In a preferred embodiment, the hybrid plant is selected from the genus *Secale* or *Triticale*, preferably a plant of the species *Secale cereale*, in which its pollen fertility for the Pampa CMS has been restored and/or which has an enhanced resistance against a fungal pathogen, in particular against the fungus *Claviceps purpurea* (Fr.). In particular, the oligonucleotides and nucleic acids as well as recombinant DNA, vectors and antibodies may also be of use in the production of a transgenic plant.

In a further aspect, the present invention concerns the use of a nucleic acid molecule which codes for an mTERF protein, or of encoded mTERF proteins in a plant, in particular from the gramineous order (Poales), preferably from the sweet grass family (Poaceae), in order to restore a cytoplasmic male sterility (CMS), in particular the Pampa CMS. Preferably, restoration is carried out by crossing the plant containing the nucleic acid molecule as a paternal parent with a second plant, preferably from the same species, containing the CMS cytoplasm. Preferably, the nucleic acid molecule is the nucleic acid molecule in accordance with the invention described above, which is capable of mediating the restoration property, or in the case of the mTERF protein, it is the mTERF protein in accordance with the invention.

Further embodiments and advantages of the present invention will become apparent from the detailed description, figures and the examples.

First of all, some of the terms used in this application will be defined in more detail below: The term "allele" should be understood to mean two or more different nucleotide sequences which are located at a specific gene locus on a chromosome. A first allele is on one chromosome, a second on a second chromosome at the same position. If the two alleles are different, they are heterozygous, and if the alleles are the same, they are homozygous. Different alleles of a gene (gene alleles) differ in at least one SNP (single nucleotide polymorphisms). Depending on the context of the description, an "allele" also means only a single SNP which, for example, allows a distinction between the donor of RFP1 and recurrent parents. Different gene alleles can also be detected by using markers. Such gene alleles at a specific locus are also known as "marker alleles". Depending on the context of the description, a "marker locus" should also be understood to mean a marker allele at a specific locus.

The expressions "chromosome fragment", "chromosome segment" as well as variations in the terms such as "chromosomal segment" or "chromosomal fragment", unless otherwise stated, are equivalent and describe a specific chromosomal DNA section of a specific chromosome which comprises at least one gene. An "integrated chromosomal fragment" thus originates from a donor source. In the context of the invention, the sequential succession of genes within an integrated chromosomal fragment corresponds to that sequence that is present in the original chromosomal fragment of the donor source. A chromosomal fragment or a portion thereof may constitute a specific "haplotype", wherein the chromosomal fragment then comprises specific SNPs through which the haplotype is uniquely specified and can be identified.

The terms "distal" and "proximal" describe the position of a chromosomal interval or a genetic fragment in relation to a specific reference location (for example a specific polynucleotide, another chromosomal interval or a gene) on a whole chromosome, wherein "distal" means that the interval or the section is located on the side of the reference location away from the chromosome centromer, and "proximal" means that the interval or the section is located on the side of the reference location which is facing the chromosome centromer.

The terms "coupled", "close-coupled" or "close-flanking" should be understood to mean that two loci (for example two genetic sections or two markers (marker loci or marker alleles)) on a gene map are less than 2 cM, less than 1 cM, less than 0.5 cM, less than 0.2 cM, less than 0.1 cM, less than 0.05 cM or less than 0.01 cM apart from each other.

The term "yield" in the context of the present invention concerns the productivity per unit area of a specific plant product with commercial value. As an example, the "yield" of rye is usually measured in metric tonnes of seed or grain per hectare (ha) and season or in metric tonnes of dry biomass per hectare (ha) and season. Unless stated otherwise, or specified otherwise, the "yield" may refer to the absolute fresh or dry matter, the relative fresh or dry matter, the silage yield (also Total Dry Matter) or the grain yield. The yield is influenced by genetic and environmental factors and is principally a combination of many agronomic properties which are based on traits of a plant which are based on general elements and which, over the season, contribute to the final yield. Examples of these individual agronomic properties are vegetative vitality, stress tolerance, disease resistance or tolerance, herbicide resistance, tillering tendency, flowering point, seed setting, grain/ear count, thousand grain weight, stability and lodging tendency, threshability, etc.

A "functional fragment" of a nucleic acid molecule means a section of a nucleic acid molecule which has a functionality which is identical to or comparable with the total nucleic acid molecule from which the functional fragment derives. As such, the functional fragment may have a nucleotide sequence which, over a length of at least 50%, 55%, 60%, 65%, 70%, 75%, 80%, 85%, 90%, 92%, 94% 96%, 97%, 98% or 99%, is identical to or homologous with the total nucleic acid molecule. A "functional fragment" of a protein means a section of the amino acid sequence of a protein which has a functionality which is identical to or comparable with the total amino acid sequence of the protein from which the functional fragment derives. As such, the functional fragment may have an amino acid sequence which, over a length of at least 50%, 55%, 60%, 65%, 70%, 75%, 80%, 85%, 90%, 92%, 94% 96%, 97%, 98% or 99%, is identical to or homologous with the total amino acid sequence of the protein.

In the context of the invention, the term "homologue" should be understood to mean a protein of the same phylogenetic origin, the term "analogue" should be understood to mean a protein which exerts the same function, but is of another phylogenetic origin, and the term "orthologue"

should be understood to mean a protein from another species which exerts the same function.

The term "hybridization" or "hybridizing" should be understood to mean a procedure in which a single-stranded nucleic acid molecule pairs to a nucleic acid strand which is as complementary as possible, i.e. base-pairs. Examples of standard methods for hybridization are described in Sambrook et al., Molecular Cloning: A Laboratory Manual 3rd Ed. Cold Spring Harbor Laboratory Press. Cold Spring Harbor, NY, 2001. Preferably, this should be understood to mean at least 60%, more preferably at least 65%, 70%, 75%, 80% or 85%, particularly preferably 90%, 91%, 92%, 93%, 94%, 95%, 96%, 97%, 98% or 99% of the bases of the nucleic acid molecule base-pair with the nucleic acid strand which is as complementary as possible. The possibility of such pairing depends on the stringency of the hybridization conditions. The term "stringency" relates to the hybridization conditions. High stringency is when a base pairing is made difficult, and low stringency is when base pairing is easier. The stringency of the hybridization conditions depends, for example, on the salt concentration or ionic strength and the temperature. In general, the stringency can be increased by raising the temperature and/or reducing the salt content. The term "stringent hybridization conditions" should be understood to mean those conditions in which a hybridization primarily takes place only between homologous nucleic acid molecules. The term "hybridization conditions" here relates not only to the conditions prevailing during actual pairing of the nucleic acids, but also to the conditions prevailing during the associated washing steps. Examples of stringent hybridization conditions are conditions under which, primarily, only those nucleic acid molecules hybridize which have at least 70%, preferably at least 75%, at least 80%, at least 85%, at least 90% or at least 95% sequence identity. Examples of stringent hybridization conditions are: hybridization in 4×SSC at 65° C. and then washing several times in 0.1×SSC at 65° C. for approximately 1 hour. The term "stringent hybridization conditions" used here may also mean: hybridization at 68° C. in 0.25 M sodium phosphate, pH 7.2, 7% SDS, 1 mM EDTA and 1% BSA for 16 hours and then washing twice with 2×SSC and 0.1% SDS at 68° C. Preferably, a hybridization is carried out under stringent conditions.

The term "interval" or "chromosomal interval" means a continuous linear section on a genomic DNA which is present in an individual chromosome in planta or on a chromosomal fragment and which is usually defined by indicating two markers which determine the end points of the interval on the distal and proximal side. In this regard, the markers which define the terminals of the interval may also be part of the interval. Furthermore, two different intervals may also overlap. In the description, an interval is specified by the indication "between marker A and marker B". A terminal marker of an interval may also be located in a defined marker region to one side of the interval. A marker region is then defined by providing two flanking markers and constitutes a chromosomal section on which further markers can lie, in addition to the flanking markers. Flanking markers determine the end points of a marker region and are themselves part of the marker region. If two end markers of an interval are markers in different marker regions either side of an interval, then in the description an interval is specified by the statement "between a marker in a marker region X which is flanked by the markers C and D, and a marker in a marker region Y which is flanked by the markers E and F".

The term "introgression" as used in the context of the present invention means the transmission of at least one desired gene allele to a genetic locus from one genetic background to another. As an example, an introgression of a desired gene allele at a specific locus can be transmitted to a descendant by sexual crossing between two parents of the same species. Alternatively, for example, the transmission of a gene allele may also occur by recombination between two donor genomes in a fused protoplast, wherein at least one donor protoplast carries the desired gene allele in its genome. In each case, the descendants, which then comprise the desired gene allele, are then back-crossed repeatedly with a line which comprises an excellent genetic background, and selected for the desired gene allele. The result is fixing of the desired gene allele in a selected genetic background.

The term "linkage drag" is used in general to describe the phenotypical expression of unwanted donor genes which reside in the same genomic region as the target QTL (Quantitative Trait Locus) and thus are closely coupled with it. As an example, this includes the observation that, by means of introgression of the chromosomal fragment which carries the restorer gene(s), donor genes which have a negative effect are transferred into the introgression line, so that the introgression line then performs less well for specific agronomic traits than the original recipient line.

In the case of restoration of male fertility, Rfp1-carrying introgression segments usually manifest linkage drag in the form of deleterious effects on the yield, i.e. grain yield and other properties such as plant height, grains per ears and thousand grain weight; see, for example, Hackauf et al., J. Kulturpfl. 61 (2009), 15-20; Hackauf et al., Molecular Breeding 30 (2012), 1507-1518.

The feature that in an inventive hybrid plant, a linkage drag otherwise coupled with the restoration property is reduced or (completely) eliminated, relates to the linkage drag which would otherwise occur in a hybrid plant (control plant). The control plant has in its genome a chromosomal segment on chromosome 4R with at least one interval from marker locus tc256739 to marker locus tc176835 from a donor selected from the group consisting of IRAN IX, Pico Gentario and Altevogt 14160. This is the same for the interval Xp15/55-Xscxx04 segment from IRAN IX; see Hackauf et al., Molecular Breeding 30 (2012), 1507-1518. Unless otherwise stated, alternatively or in addition, the term "feature that in an inventive hybrid plant, a linkage drag otherwise coupled with the restoration property is reduced or completely eliminated" should also be understood to mean the improvement in a property of the hybrid plant in accordance with the invention compared with a control plant. Thus, for example, this could be applied to an increased pollen shedding which results in the minimization of ergot infestation.

A "locus" is a position on a chromosome where one or more genes or one or more gene alleles can be found, which cause or influence an agronomic trait. In particular, "locus" here means the Rfp1 locus which restores the pollen fertility for the Pampa cytoplasmic male sterility (CMS).

The term "marker" describes a nucleotide sequence which is used as a reference or orientation point. A marker for detecting a recombination event should be suitable for monitoring differences or polymorphisms within a plant population. For markers, these differences are on the DNA level and, for example, are polynacleotide sequence differences such as, for example, SSRs (simple sequence repeats), RFLPs (restriction fragment length polymorphisms), FLPs (fragment length polymorphisms) or SNPs (single nucleotide polymorphisms). Markers may be derived from genomic or expressed nucleic acids such as, for example, spliced RNA, cDNA or ESTs and may also refer to nucleic acids which are used as probes or primer pairs and as such are suitable for amplification of a sequence fragment using a PCR-based method. Markers which recognize genetic polymorphisms between members of a population can be detected by means of established methods from the prior art (An Introduction to Genetic Analysis. 7th Edition, Griffiths, Miller, Suzuki et al., 2000). Examples of these are: DNA sequencing, PCR-based, sequence-specific amplification, detection of RFLPs, or detection of polynucleotide polymorphisms using allele-specific hybridization (ASH), detection of SSRs, SNPs or RFLPs. Moreover, methods for the detection of ESTs (expressed sequence tags) and RAPD (randomly amplified polymorphic DNA) are also known. Depending on the context, the term "marker" in the description may also mean a specific chromosomal position in the genome of a species where a specific marker (for example SNP) can be found. Such a marker position may be used in order to monitor the presence or absence of a coupled locus, for example a coupled locus which contributes to the expression of a specific phenotypical trait (for example Rfp1 or linkage drag). As an example, the marker locus may also be used in order to observe the segregation of alleles at a locus (QTL or individual gene) which is genetically or physically close-coupled with the marker position.

"Operatively connected" means connected in a common nucleic acid molecule in such a manner that the connected elements are positioned and/or orientated with respect to each other such that a transcription of the nucleic acid molecule can take place. A DNA which is operatively connected with a promoter is under the transcriptional control of that promoter.

Particle "organs" mean, for example, leaves, plant stem, trunk, roots, vegetative buds, meristems, embryos, anthers, ovulae, seeds or fruits, in particular seed grain. The term "plant portion" or "plant portions" includes, but is not limited to the plant stem or the stalk, leaves, flowers, inflorescences, roots, fruit and seeds as well as the pollen. Furthermore, plant "portions" means an aggregation of a plurality of organs, for example a flower or a seed, or a portion of an organ, for example a cross section through the plant stem. Examples of plant "tissue" are callus tissue, soft tissue, meristem tissue, leaf tissue, shoot tissue, root tissue, plant tumour tissue or reproductive tissue as well as the formative tissue, functional tissue (known as the parenchymal tissue), vascular tissue, strengthening tissue and covering tissue (known as the epidermis). However, the tissue is not limited to this list. The term plant "cells" should be understood to mean, for example, isolated cells with a cell wall or aggregates thereof or protoplasts.

In the context of the invention, unless stated otherwise, a "plant" derives from any dicotyledon, monocotyledon and gymnosperm species. Preferably, the plants are monocotyledon and are of importance in agriculture and market gardening or for the production of bioenergy (bioethanol, biogas, etc). Examples include *Gossypium* sp., *Zea mays, Brachypodium distachyon, Triticum* sp., *Hordeum vulgare, Oryza sativa*, Sorghum sp., Musa sp., *Saccharum officinarum, Secale cereale, Avena* sp., lawn and forage grass. A plant in accordance with the invention is preferably a plant from the genus *Secale*, in particular the species rye (*Secale cereale*).

The expression "resistance" or "resistant" to a pathogen should be understood to mean the resistance or defensive power of a plant or plant cell to the damaging influences of the pathogen and extends from inhibiting the development of disease to complete suppression of the development of the disease. As an example, the resistance of Rfp1-carrying hybrids to ergot is a resistance based on an "escape" mechanism: spores of the fungus are mechanically denied access to the gynoecium because of the fast-closing husks following fertilization by the pollen. A mediated resistance may be a newly-attained resistance or an increase in an already existing partial resistance. In connection with the present invention, a plant/plant cell is resistant or has a resistance to the pathogen ergot, i.e, a hybrid plant which exhibits an increased resistance to a pathogen, preferably against a fungus, in particular against the fungus *Claviceps purpurea* (Fr.).

The term "cereal plants" should be understood in particular to mean monocotyledon plants which belong to the gramineous order (*Poales*), preferably to the sweet grass (*Poaceae*) family. Examples in this case are plants which belong to the genuses *Avena* (yeast), *Triticum* (wheat), *Secale* (rye), *Oryza* (rice), *Panicum, Pennisetum, Setaria, Sorghum* (millet), *Zea* (maize) etc., preferably *Hordeum* (barley). *Secale* (rye), i.e. a *Secale cereale, p. africanum, p. ancestrale, p. dalmaticum, p. kuprijanovii, p. montanum, p. silvestre, S.vavilovii* plant, is particularly preferred.

A "transgenic plant" refers to a plant the genome of which has integrated into it at least one polynucleotide, preferably a heterologous polynucleotide. Preferably, the polynucleotide is stably integrated, which means that the integrated polynucleotide remains stable in the plant, is expressed and is also inherited in the descendants in a stable manner. The stable introduction of a polynucleotide into the genome of a plant also includes integration into the genome of a plant of the preceding parental generation, whereupon the polynucleotide can be further inherited in a stable manner. The term "heterologous" means that the introduced polynucleotide, for example, originates from a cell or an organism with a different genetic background from the same species or from another species, or is homologous to the prokaryotic or eukaryotic host cell, but is then localized in a different genetic environment and thus is different from a corresponding polynucleotide which is possibly naturally present. A heterologous polynucleotide may be present in addition to a corresponding endogenous gene.

The term "yield-reducing effect" should be understood to mean the phenotypical expression of a DNA sequence which is coupled or close-coupled with the target gene, in this case the restorer gene, and thus co-segregates. This is a frequent problem in backcrossing programs with exotic donors, namely the joint inheritance of desired and unwanted genes for the purposes of breeding described, for example, by Brinkmann et al., Crop Sci. 17 (1977), 165-168 and Tanksley et al., Bio/Technology 7, (1989) 257-264. This complex of the restorer gene and further unwanted genes, which are in part yield-reducing, has until now always been transmitted in part or in full into the breeding material, whereupon the introgression lines, for example, in addition to the advantageous restoration property, contain other negative traits which, for example, and depending on the location, bring about a significant reduction in yield. Correspondingly, linkage drag here is advantageously a negative yield effect which is connected with efficient restoration capability.

A reduction or alleviation of linkage drag occurs when its negative phenotypical properties as regards the control plant are only 0 to 75%, which corresponds to a reduction of 25-100%. In a preferred embodiment, the reduction is 50-100% or 75-100%. In a particularly preferred embodiment, the negative properties which are connected with linkage drag are almost completely or completely eliminated and the reduction in the linkage drag is between 90% and 100%. A reduction or alleviation of linkage drag for hybrid plants in particular may also mean a linkage drag effect on the yield of less than 7 dt/ha (quintals per hectare), less than 6.5 dt/ha or less than 6 dt/ha, preferably less than 5.5 dt/ha, less than 5 dt/ha, less than 4.5 dt/ha or less than 4 dt/ha, or most particularly less than 3.5 dt/ha, less than 3 dt/ha, less than 2.5 dt/ha or less than 2 dt/ha compared with a corresponding near-isogenic plant or hybrid plant which does not contain the inventive chromosomal segment or the inventive nucleic acid molecule. In order to quantify the linkage drag, the linkage drag effect can be standardized as a percentage of the performance of the NIB-E partner, as will be described below in Examples 1 and 2.

The term "vector" or "vector system" as used here in connection with genome editing refers to a transport means for introducing a recombinant construct comprising nucleic acids or even polypeptides as well as optional further sequences such as regulatory sequences or localization sequences, directly or indirectly into a desired target cell or target plant structure into the desired cellular compartment. Direct introduction is carried out into a target plant cell or target plant structure which contains nucleic acids which, in accordance with the present disclosure, are to be modified in a specific manner. Indirect introduction comprises introduction into a structure, for example cells of leaves or other plant organs or tissue which in fact are not of direct interest to the target plant cell, but wherein the systemic propagation and onward transmission of the vector comprising a recombinant construct in accordance with the present disclosure into the target plant structure, for example meristem tissue or cells or stem cells, is ensured. The term "vector" in the context of the transfection of amino acid sequences encompasses suitable agents for peptide or protein transfection such as, for example, ionic lipid mixtures or agents which are suitable for transfection of a nucleic acid, such as, for example, carrier materials by means of which nucleic acid and amino acid sequences can be introduced into a cell by bombardment with particles such as gold and tungsten particles, for example. Furthermore, this term also encompasses viral vectors, i.e. modified viruses such as, for example, those which derive from the following viruses: Barley Stripe Mosaic Virus (BSMV), Brome Mosaic virus (BMV), Maize yellow dwarf virus (MYDV) and bacterial vectors such as *Agrobacterium* spp., for example *Agrobacterium tumefaciens*. Finally, the term also encompasses suitable transport means for introducing linear nucleic acids (single- or double-stranded) into a target cell. The person skilled in the art in this field will be aware of other sequences which a vector must contain in order to be functional in a desired target cell. Conventional production, working-up and use of vectors of this type are also known to the person skilled in the art in this field.

The term "recombinant construct" as described herein in connection with genome editing refers to a construct comprising, inter alia, plasmids or plasmid vectors, cosmids, synthetic yeast or bacterial chromosomes (YACs and BACs), phagemids, bacteriophage vectors, an expression cassette, single-stranded or linear nucleic acid sequences or amino acid sequences, and viral vectors, i.e. modified viruses which can be introduced into a target cell in accordance with the present disclosure. A recombinant construct in accordance with the invention may comprise genome editing tools or parts thereof. As an example, CRISPR/Cas tools or parts thereof comprise at least one gRNA or at least one Cas nuclease variant and/or at least one further effector domain, either in the form of a nucleic acid or an amino acid sequence. TALENs tools or parts thereof comprise, for example, at least one TAL effector domain and/or at least nuclease variants, preferably a type II endonuclease such as FokI, for example. Furthermore, the recombinant construct may comprise regulatory sequences and/or localization sequences. The recombinant construct may be integrated into a plasmid vector and/or be isolated from a plasmid vector, for example in the form of a polypeptide sequence or a single or double-stranded nucleic acid not connected to a plasmid vector. After introduction, the construct is intrachromosomal or, as is preferable, extra-chromosomal and is not integrated into the genome and usually in the form of a double-stranded or single-stranded DNA, a double-stranded or single-stranded RNA or a polypeptide.

Embodiments and Implementations of the Present Invention Will Now be Described by Way of Example with Reference to the Accompanying Figures and Sequences:

FIG. 1: Genetic and physical map of the Rfp1 locus. A) High resolution genetic map of the Rfp1 locus on the long arm of the rye chromosome 4R. The numbers under the uppermost horizontal line describe the number of recombination events observed between the associated markers among 4563 individual test plants. Information regarding the marker codings are listed in Table 2. B) Rfp1-spanning contig of BAC clones from the Sce-B-R05104 library. C) Predicted genes on the Rfp1 locus. The bold boxes represent exons of functional genes or gene fragments, pseudogenes or mutated genes. The orientation of the genes is indicated by horizontal arrows. The vertical line in the mTERF gene 175019_c7 describes an early stop codon in the gene sequence. The abbreviations F and C indicate that for the marker concerned, a dominant restorer genotype specific for fertility (F) or a co-dominant inheritance (C) has been observed.

FIG. 2: Mapping of functional restorer genes on Rfp1 locus. With the aid of molecular selection markers, in two exemplary test series, recombinant individual plants with different lengths of donor chromosomal segments (D) were identified in the genetic background of a pollen parent line (E). The expression of the functional restorer genes Rfp1a and Rfp1b was determined in test crossing descendencies for each recombinant plant with the highly diagnostic male-sterile tester genotype Lo6-P(SR). Table 2 lists the marker haplotype of the NIB partner D which carries the donor introgression segment. $\Delta_{E\text{-}D}$: difference between the means of test crossings from NIB partners which each homozygously carry the elite allele (E) or the donor allele (D). This difference in the mean over 7 locations determines the linkage drag effect for grain yield absolutely in dt/ha and as a percentage of NIB partner E. LSD5%: limiting difference, 5% level of significance.

Figure 3:
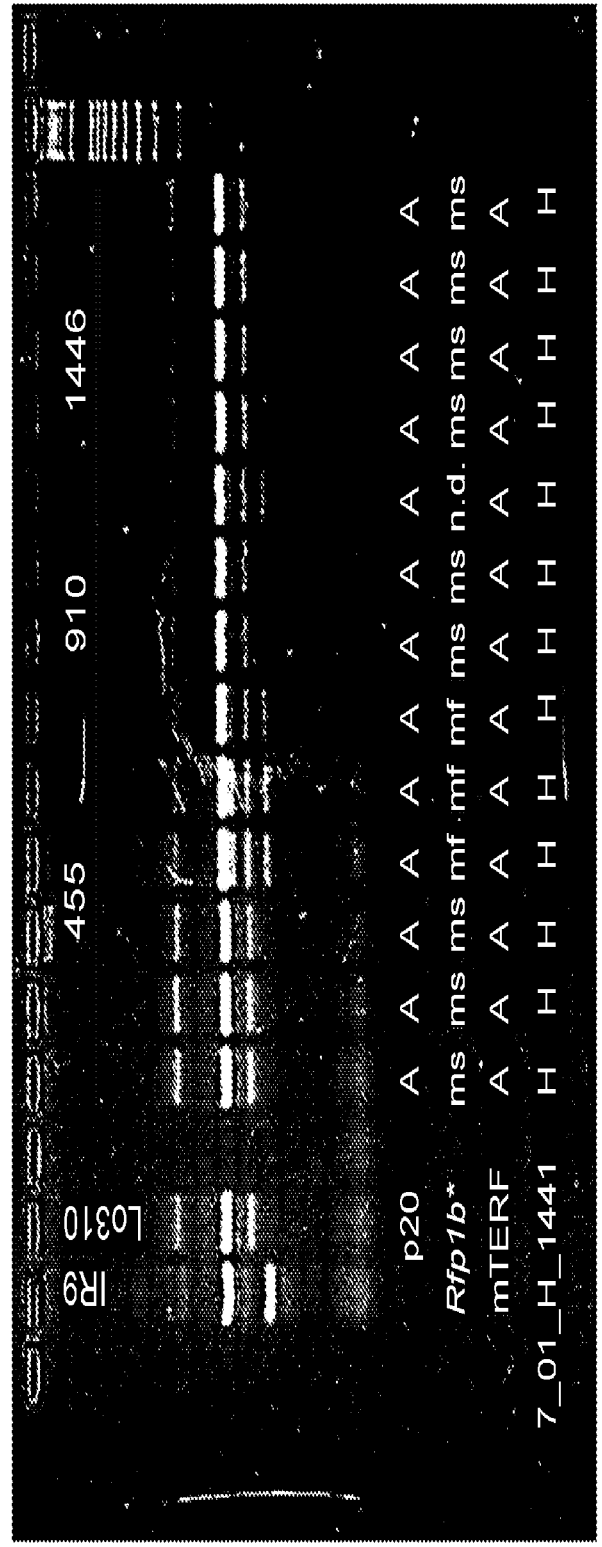

FIG. 3: Mapping of restorer gene Rfp1b. From 13 recombinant plants, the allele of the donor genotype IR9 could be unambiguously determined between the markers P20 and 7_01_H_1441 at the marker locus 72F13_c2_mTERF in 4 plants. The Rfp1b phenotype was detected in test crossing descendencies of the recombinant genotypes with the CMS tester Lo6-P(SR) and matched perfectly with the marker genotypes of the mitochondrial transcription tERmination factor (mTERF) mapped by means of 72F13_c2_mTERF [A=homozygous carrier of elite allele; H=heterozygous carrier of elite or donor allele; Rfp1b*=Rfp1 or elite phenotypes were detected using the pollen shedding of respectively 15 individual test crossing descendants of the recombinant genotype and the highly diagnostic tester from Lo6-P(SR).]

Figure 4:
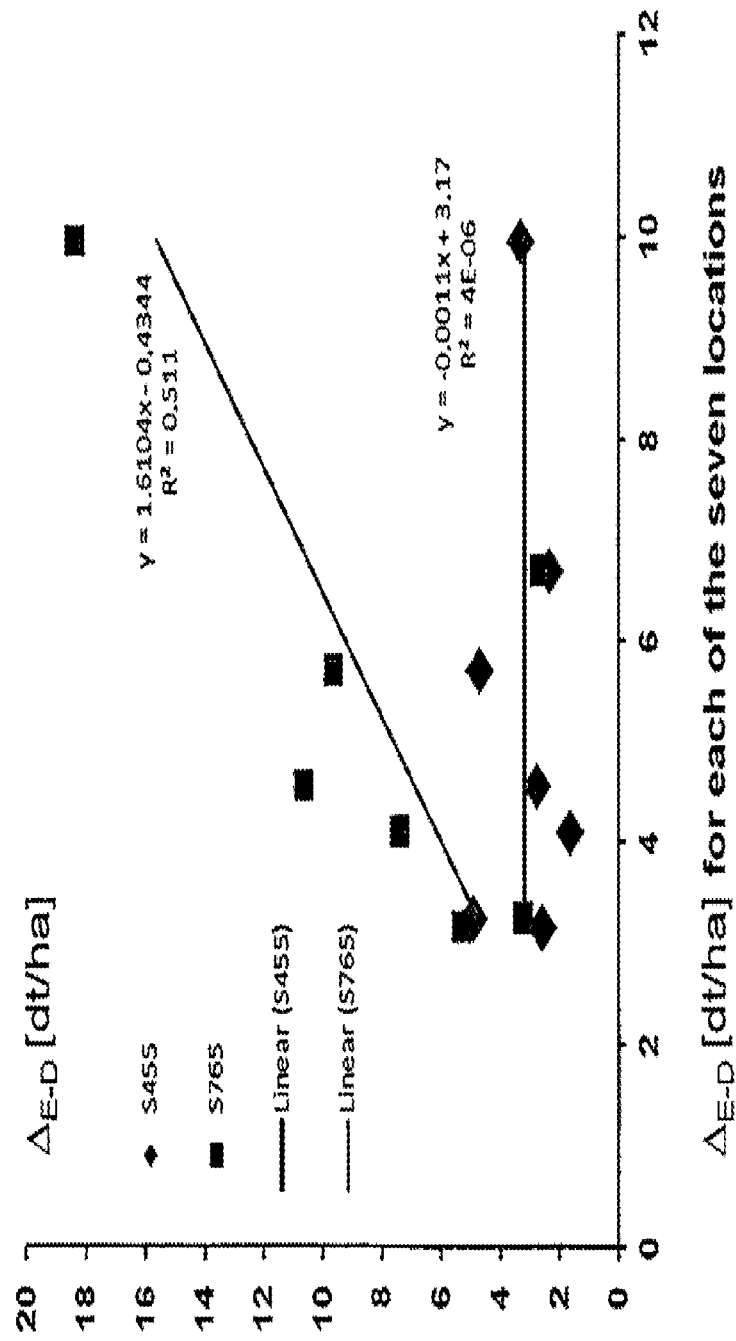

FIG. 4: Shows the linkage drag effect for grain yield ($\Delta_{E-D}$) for the introgression segment 455 and 765 (y-axis), plotted against the mean linkage drag effect for each of the seven locations (x-axis). The recombinants with the short introgression segment 455 exhibited a low linkage drag effect, and the recombinants 765 with the long introgression segment exhibited a large linkage drag effect. It was also clear from the experimental data that the linkage drag effects for the seven environments were very different. Clearly, adverse weather conditions during the shooting phase were responsible for the stress conditions.

Figure 5:
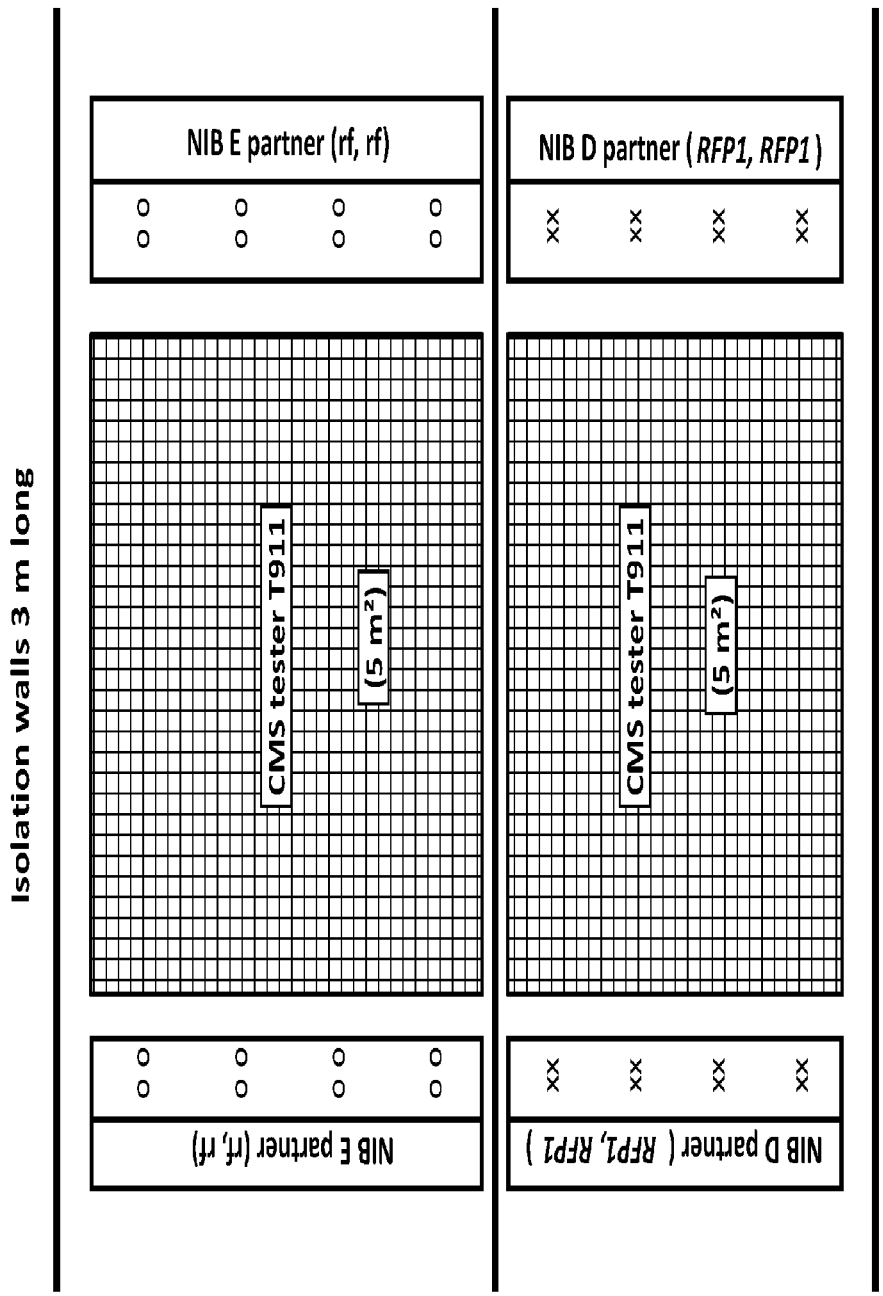

FIG. 5: Production of test crossing seed with Near-Isogenic Bulk partners as the pollen parent and CMS "single cross" tester T911 as the female parent. The use of NIB partners (NIB pairs) is shown in isolation parcels which acted for seed production from test crossing seed. In this regard, NIB partners dusted a CMS "single cross" tester which represented the opposing heterotic pool. Seed which was harvested on the CMS testers was then sown in field experiments with multiple environments in order to determine the linkage drag effect phenotypically.

Figure 6:
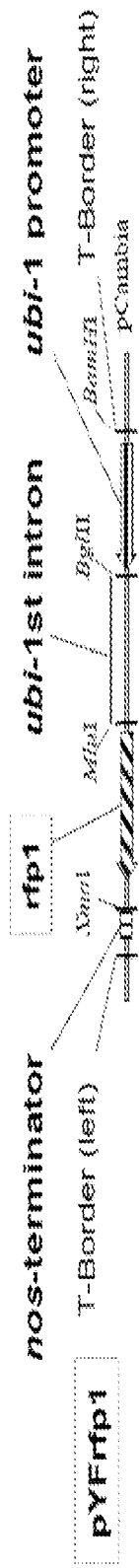

FIG. 6: Expression cassette in the vector pYFrfp1 containing the restoration gene rfp1b (SEQ ID NO: 1) under the control of the ubiquitin promoter from maize with the first intron and nos-terminators.

FIG. 7: Comparison of the nucleotide sequence of the wild type rfp1a gene ("Wildtyp-rfp1a") (SEQ ID NO: 32) with the nucleotide sequence of the rfp1a gene from IRAN9 ("Iran9_rfp1a") (SEQ ID NO: 28).

FIG. 8: Comparison of the nucleotide sequence of the wild type rfp1b gene ("Wildtyp-rfp1b") (SEQ ID NO: 30) with the nucleotide sequence of the rfp1b gene from IRAN9 ("Iran9_rfp1b") (SEQ ID NO: 1).

FIG. 9: Comparison of the amino acid sequence of the wild type rfp1a protein ("Wildtyp-rfp1a") (SEQ ID NO: 33) with the amino acid sequence of the rfp1a protein from IRAN9 ("Iran9_rfp1a") (SEQ ID NO: 29).

FIG. 10: Comparison of the amino acid sequence of the wild type rfp1b protein ("Wildtyp-rfp1b") (SEQ ID NO: 31) with the amino acid sequence of the rfp1b protein from IRAN9 ("Iran9_rfp1b") (SEQ ID NO: 2).

The following examples illustrate the invention without in any way limiting the subject matter of the invention. Unless stated otherwise, standard methods were employed.

EXAMPLES

Example 1: Exemplary "Near Isogenic Bulk"—Development of Rye Line 455 in Lo310 Background As can be seen in FIG. 5, for all recombinant genotypes, NIB D and E partners were produced in which bulks each of more than 100 $BC_6S_1$ plants, which were homozygous carriers or non-carriers of the Rfp1, were outcrossed with the single cross CMS tester T911. Boundary isolation walls ensured that no foreign pollination occurred. The test crossing seed produced in this manner was then used in field trials in multiple environments. Test crossing plants were verified for the correct pedigree by (i) subsequent marker analysis and (ii) evaluation of the pollen shedding in the field trials. All of the evaluated test crossing plants which were generated from the NIB D partners exhibited full pollen shedding, while those which originated from the E partners exhibited a very significantly reduced and only partially restored male fertility.

Example 2: Field Trials

The yield evaluation trials were carried out at locations with different environmental conditions. Thus, for example, in 2012, there were seven locations in Germany (D) and Poland (PL). As can be seen in Table 1, the locations were selected so that they represented agricultural conditions in Central Europe with, additionally, different stress conditions (drought stress and nitrogen deficiency). In the low nitrogen regime, nitrogen was applied in quantities which were substantially below the usual doses. In an unwatered trial, natural precipitation constituted the only source of water, while in the watered trials, an additional quantity of water of approximately 25 mm per week was applied. In this manner, it was possible to measure effects of the Rfp1 introgression segments in very different environments. The results were then used (1) to determine the introgression segment-specific linkage drag effect, (2) to identify introgression segments with high environmental stability, and (3) to identify diagnostic environments which make the linkage drag discernible to a greater extent.

TABLE 1

Description of the trial locations and the applied treatments in 2012 (BEK = Bekedorf (Lower Saxony); KON = Kondratowice (Lower Silesia); BBG = Bernburg (Saxony-Anhalt); KO2 and KO3 = Bergen (Lower Saxony); PET_I and PET_N = Petkus with watering (I) and nitrogen variants (N) (Brandenburg); Ground points: index measuring the quality of an area of farmland. The scale of possible values extends from 1 (very poor) to 100 (very good).)

| Location | State | Ground points | Precipitation mean [mm] | Agronomic regime |
|---|---|---|---|---|
| BEK | D | 51 | 769 | |
| KON | PL | 55 | 581 | local agricultural practice |
| BBG | D | 93 | 469 | |
| KO2 | D | 43 | 769 | low nitrogen |
| KO3 | D | 43 | 769 | not watered |
| PET_I | D | 28 | 636 | watered |
| PET_N | D | 28 | 636 | not watered |

A "split plot" trial design was used for all environments. The main plots used the test crossings of the recombinant $BC_6S_1$ lines. The subplots were the respective near-isogenic D and E bulk NIB pairs. The "NIB D partner" was the homozygous carrier of the donor introgression segment, while the "NIB E partner" was the homozygous carrier of the corresponding elite line segment. The corresponding D and E partners were sown directly adjacent to each other in order to minimize environmental differences and thus to be able to measure the differences due to the introgression segment with more accuracy. Trial units of the yield experiments were the test crossings from 7 $BC_6S_1$ lines, which themselves represented four different haplotypes. As an example, the results for the recombinant with the shortest introgression segment (455) are shown compared with that with the longest introgression segment (765) in detail. The latter is already significantly shorter than the segments which are currently available for hybrid varieties which have already been approved.

The preparation and implementation of the field trials were in accordance with the general rules and are well known to the person skilled in the art. The statistical analysis of the data was carried out in two steps: firstly, at each individual location, a variance analysis was calculated for all repeats with the aim of determining the accuracy of the trial and to determine respective location-specific yield averages for the recombinant lines and their introgression segments. In a second step, said averages were then used for the analysis regarding the environments.

Drastic and statistically significant differences (t-test) for the linkage drag effect were detected, for example, between the recombinant genotypes 455 and 765. As can be seen in FIG. 2, the linkage drag effect averaged over the locations ($\Delta_{E-D}$) was 3.7 dt/ha for haplotype 455, while it was nearly twice that (7.0 dt/ha) for haplotype 765. The differences between the two recombinants manifested themselves particularly clearly at location PET_N under high stress due to spring drought. Here, the linkage drag effect ($\Delta_{E-D}$) for recombinant 765 rose to 18 dt/ha, while it remained at only 3 dt/ha for haplotype 455. At another location (BBG) under moderate stress conditions, the linkage drag effect ($\Delta_{E-D}$) dropped to 11 dt/ha for the haplotype 765, which, however, was a multiple of that shown by haplotype 455 with only about 3 dt/ha. Fundamentally similar relationships were found in the experiments carried out in 2014. Here again, shortening of the introgression segment corresponded to a reduction in linkage drag for yield. In order to be able to compare the experiments in 2012 and 2014 with each other, it was recommended that the linkage drag effect be standardized as a percentage of the performance of the NIB partner. FIG. 2 illustrates that the linkage drag for the recombinants with the shortest introgression segments (1120 and 455) were only between 3.9% and 4.7%, while the recombinants with the longest introgression segments (1110 and 765), with 6.2% and 7.1%, suffered substantial performance losses. However, the yield reductions cited latterly are still relatively small when set in context, i.e. currently known introgression segments which contain the two markers tc256739 and tc300731 cause linkage drag effects of more than 10%.

The locations differ in their diagnostic value for detection of linkage drag (see FIG. 4). Means for $\Delta_{E-D}$ over all tested introgression segments in 2012 (Series 018/2012) were from 3.2 (PET_I), 3.3 (KON), 4.1 (KO2), 4.6 (BBG), 5.7 (Ko3), 6.7 (BEK) to 10.0 (PET_N) dt/ha. The smallest mean linkage drag effect was observed in the watered trials in Petkus (PET_I), in which the availability of water was not limited. In contrast, the unwatered trials in the same macro-environment (PET_N) were very strongly influenced by drought in the pre-flower phase. It can be seen (FIG. 4) that the segment from 765 reacted significantly to environmental stress (regression coefficient on the mean linkage drag effect: 1.6 dt/ha). In contrast to this, the segment from 455 exhibited a very high environmental stability which could be confirmed in the PET-N stress environment.

Example 3: Identification of Recombinant Genotypes

In order to identify recombinant genotypes and in order to describe the respective remaining introgression segments, the following markers were used: ctg24, ctg32, ctg16b, P20, c40745, wherein the marker P20 played the most significant role in all of the subsequent studies. From a publicly available rye BAC library developed from cv. Blanco, which is not a carrier of the Rfp1 gene (Shi B J, et al. (2009): Physical analysis of the complex rye (Secale cereale L.) Alt4 aluminium (aluminum) tolerance locus using a whole-genome BAC library of rye cv. Blanco. Theor Appl Genet. 119(4):695-704), and with the aid of marker P20, BACs could be identified as a source for further marker sequences. It was possible to isolate and sequence a highly promising BAC. This opened up the possibility of providing a BAC library of restorer gene-carrying genotypes (denoted here as "IR9" or ROS104), which can be viewed with specific DNA probes using PCR. Although no Rfp1 locus-spanning BAC contig could be produced, the locus flanking BAC clones could be identified with the aid of this library. Multiple marker combinations could be designed using the sequences: see Table 2. These were used for the selection of new recombinants and partially converted into a new marker system (SNP-based).

Furthermore, with the aid of the investigations with mTERF, a novel Rf gene could be identified which until now has not been described as being of relevance to fertility restoration for any plant species. For the first time it has been shown that at the 4R introgression segment, two standalone and also equal-valued Rf genes are effective having regard to restoration.

With the aid of close-flanking markers and a phenotyping test, for both Rf genes involved, it could be shown that the respective donor introgression segments could be made even smaller and the restoration capability could be maintained in full.

Example 4: Development of Close-Coupled Markers

In order to develop close-coupled markers for the Rfp1 locus in rye, as well as in order to isolate the functional restorer gene, a Rfp1 allele from the exotic breed IRAN IX was used as the most efficient source of fertility restoration. Bound up with this very efficient restoration performance, however, is a linkage drag which can cause a significant reduction in yield, depending on the respective location.

In addition to the close-coupled marker P20, for fine mapping of the Rfp1 region, further proximal close-coupled markers were provided. Essentially, this was carried out using two strategies which enabled one recombinatorily shortened genomic interval per molecular marker to be selected and thus, finally, to enable the unwanted linkage drag to be identified and reduced.
1) The first strategy is based on the exploitation of conserved synteny between rye and Brachypodium as well as rye and barley. In this manner, novel close-coupled markers were derived using gene information from the two cited model grass/cereals varieties.
2) The second strategy starts from the assumption that the close coupling of the marker P20 also indicates a close physical coupling, and is based on the chromosome walking method. This means that, by means of close-coupled markers, a freely available rye BAC library was searched (population variety "Blanco" (Shi et al., Theor Appl Genet 119 (2009), 695-704), in order to produce an initial BAC contig as the starting point for a contig analysis of the Rfp1 locus. For this, a newly established BAC library of the restorer gene-carrying genotype (described here as "IR9" or ROS104) could be viewed with specific DNA probes using PCR.

With the aid of these libraries, BAC clones could be identified from which new markers could be derived which finally authorized selection of a smaller interval about Rfp1.

Example 5: Mapping of New Markers in the Population ROS13024-BC1 and Identification of Two Independent but Equivalently-Acting Loci for the Restoration Property (Rfp1a and Rfp1b)

As a supplement to the marker P20, in the context of the present invention, individual new markers suitable for selection were developed on the basis of the isolated BAC clones from the ROS104 BAC library. The markers obtained using the isolated bac clones were used for high resolution mapping in advanced breeding material, whereupon finally, the target interval could be further resolved. The mapping of these markers in the target interval as well as relative to the target gene was carried out in multiple experiments on internally developed, splitting populations. The markers and associated primer sequences, with the aid of which the loci for the restoration property could be identified in plants, are summarized in Table 2 below.

With the aid of the newly established selection markers, surprisingly, for the first time it was possible to show, in the mapping studies that were carried out, that the restoration property can be associated with two independent but closely coupled and almost equivalently acting restorer genes (Rfp1a and Rfp1b) at the Rfp1 locus (FIG. 1). In addition, it was shown that one of the Rf genes involved, namely the Rfp1b gene, is a gene which codes for an mTERF protein. In addition, Rfp1a has a very high sequence agreement with and can most probably be denoted as an mTERF gene. Because until now it was not known that such a gene was relevant in cereals for fertility restoration and/or pollen shedding, this result was completely unexpected.

As a consequence, with the aid of the present invention and the associated experiments, it has been shown for the first time that two independent and also almost equally-acting Rf genes having regard to restoration are located in the 4R introgression segment. Moreover, these two genes can now, for example with the aid of the markers described in this invention, also be separately evaluated for breeding purposes and can be used separately or in combination with each other. Thus, one aspect of the present invention concerns the use of the Rf gene Rfp1a alone or in combination with Rfp1b. In a further embodiment, the Rf gene Rfp1b may be used independently of Rfp1a. Preferably, both of the equivalently acting loci cited above lead to a restoration of fertility.

enabled a reliable identification to be carried out of only approximately 20 plants which could be characterized by recombination in the region of the valuable Rfp1 gene variant. In this manner, the genetic interval around Rfp1 in the genetic background of the line Lo727 was defined by the flanking markers ctg2 and 7_01_H_1441, for which a genetic separation of approximately 0.2 cM or approximately 120 kb could be calculated (FIG. 1). The genetic map produced documented that the target interval around Rfp1 could be resolved in the desired manner with the aid of the newly developed marker. Firstly, the first gene-based markers as well as the marker c40745_1 were used for selection on the genetic background of an elite pollen parent genotype. The marker P20 was employed to detect the segment with the restorer gene Rfp1. In a test series (018/2012), it was then possible to observe the expression of Rfp1 and, connected with it, the complete restoration of male fertility for different lengths of Rfp1 introgression segments (bottom of FIG. 2) using test crossings with the male stamp CMS tester Lo6-P(SR).

This discovery proves (1) coupling between Rfp1 and P20, as well as (2) the value of the developed selection marker for recombinatorial reduction of the donor chromosomal segment.

Building on this result, in further experiments (for example Ro12011), further cleaving BCx families were initially genotyped with the marker P20. In an experiment denoted test series 12-1-23, approximately 3200 individual plants were identified which inherited pure for the allele for the elite line Lo310. With the gene-based markers defined above, 4 recombinant plants with different lengths of Rfp1 introgression segments were identified in this material group (top of FIG. 2). In test crossings with these 4 lines as well as the control genotype #1058 without Rfp1 donor segment with the male-sterile CMS tester Lo6-P(SR), the expression of Rfp1 could be observed in 3 entirely male-fertile descendants of the lines 1110, 1039 and 1120. The genetic consti-

TABLE 2

Marker overview (Tm = melting temperature; *described in Hackauf et al, 2012)

| Marker ID | Derived from BAC | Forward primer (5'-3') [SEQ ID NO] | Reverse primer (5'-3') [SEQ ID NO] | Tm [° C.] | Product size [bp] | Performance | Category |
|---|---|---|---|---|---|---|---|
| tc256739* | Barley EST | 21 | 22 | 60 | 200/300 | codominant | COS |
| #1: ctg32 | 541014 contig32 | 16 | 17 | 60 | 371 | fertile pool specific | gene based STS |
| #2: ctg24met2a5 | 541O14 contig24 | 14 | 15 | 60 | 1148 | codominant | gene based STS |
| #3: ctg2 | 541014 contig2 | 4 | 5 | 60 | 221 | codominant | ISBP |
| #4: ctg16b | 541014 contig16 | 10 | 11 | 60 | 516 | codominant | gene based STS |
| #5: c40745_1 | SceAssembly02 | 18 | 19 | 60 | 675 | codominant | gene based STS |
| #6: P20 | 72F13 contig2 | 6 | 7 | 65 | 424 | fertile pool specific | gene based STS |
| #7: 72F13_c2_mTERF | 72F13 contig2 | 8 | 9 | 68 | 475 | fertile pool specific | gene based STS |
| #8: 7_01_H_1441 | 72F13 contig1 | 12 | 13 | 60 | 480 | fertile pool specific | STS |
| tc300731* | Wheat EST | 23 | 24 | 55 | 340/300 | codominant | COS |

In one of the experiments which were carried out (Ro14037), almost 5000 individual plants of a BCxS1 population were genotyped. In this regard, a genetic polymorphism between the Rfp1 donor chromosomal segment and the pollen parent line Lo727 could be detected. The genetic fingerprint produced on the basis of this marker tution of the recombinants led to the conclusion that a further, independent and equivalently acting restorer gene was located in the region of the target interval. This restorer gene coupled with the ctg2 marker was denoted Rfp1a, while the restorer gene coupled with P20 was given the notation Rfp1b (see also FIG. 1).

For the exact localization of the restorer gene Rfp1b, additional mapping experiments were carried out (for example Ro13030). In analogous manner to the experiments above, BCx interval plants in which the donor chromosomal segment had already been recombinatorially shortened with the aid of the gene-based marker from BAC clone 541014 were initially genotyped with the marker P20. In this manner, almost 4300 genotypes were identified which inherited pure for the elite allele of the pollen parent line Lo310 at this marker gene site. With the aid of the marker 7_01_H_1441, for example, a total of 13 recombinants to marker P20 could be detected in this material group (FIG. 3). In 4 of these 13 recombinants, the donor allele from the genetic source could be observed at the marker locus 72F13_c2_mTERF. For 3 of these 4 recombinants, test crossing descendants were established in which the male fertility had been completely restored. In contrast, the test crossing descendants of the 9 carriers of the non-restorer marker allele of mTERF exhibited a completely male-sterile phenotype.

By matching the observed phenotypes with the marker genotypes of a mitochondrial transcription tERmination factor (mTERF), it was possible to calculate a genetic separation between P20 and Rfp1b of r=0.094 cM. This recombination estimate was in very good agreement with the recombination estimate of r=0.011 cM calculated for the earlier experiments between P20 and the mTERF gene.

Example 6: Rfp1 Contig Production with the Aid of the BAC Library ROS104

BAC clones selected from the ROS104 BAC library acted as the basis for the development of probes and primers to continue the chromosome walking. An approximately 350 kbp contig was derived in this manner. By means of the markers and the mapping thereof in the advanced breeding material, it was shown that this contig carried markers which flanked the two restorer loci (FIG. 1 and Table 2). Experiments showed that there was no PPR protein-coding gene in this interval, but in it there were 3 so-called mTERF (mitochondrial transcription termination factor) genes or gene fragments which were therefore clearly to be seen as candidate genes for Rfp1.

On the basis of the earlier work, a BAC contig of the Rfp1 locus in the background of a restorer genotype (elite inbred line Lo310 from the pollen parent pool) was constructed and the presence of two Rf genes was demonstrated by analyses of recombinant descendants.

Example 7: Validation of Results

In addition to the detection of the identified Rfp1b gene by genetic recombination in Example 5, the functionality of the gene was also tested in a transgenic approach. To this end, the protocol for *Agrobacterium tumefaciens*-mediated rye transformation by Herzfeld (2002. Development of a genetic transformation protocol for rye (*Secale cereale* L.) and characterisation of transgene expression after biolistic or *Agrobacterium*-mediated gene transfer. Dissertation, IPK, Germany) was used. To this end, donor plants from the inbred line L22 were cultivated in a greenhouse at approximately 20° C. with 16 h of light up to the flowering point, and then immature caryopses were surface-sterilized and immature embryos were prepared. These were placed with the scutellum side uppermost onto callus-inducing medium (containing MS salts (Murashige and Skoog, 1962. "A revised medium for rapid growth and bio assays with tobacco tissue cultures." *Physiologia plantarum* 15.3: 473-497.), 100 mg/l caseine hydrolysate, 500 mg/l glutamine, 30 g/l saccharose, 2.5 mg/l 2.4-D, pH 5.8, 3.0 g/l phytagel) and pre-cultivated in darkness at 25° C. over a period of 5 days before transformation. For the purposes of the transformation, following earlier precultivation, the immature embryos were placed on 6× microplates (Greiner Cellstar) and suspended in 10 ml of liquid callus-inducing medium. For the osmotic treatment, the liquid medium was exchanged against 10 ml of osmotic medium (containing MS salts (Murashige and Skoog, 1962), 100 mg/l caseine hydrolysate, 500 mg/l glutamine, 30 g/l saccharose, 6.0 mg/l 2.4-D, 72.9 g/l mannitol, pH 5.8) and the explants were plasmolysed over a period of 4-6 h.

Next, the osmotic medium was removed again and the calluses were inoculated with approximately 300 µl of *agrobacterium* suspension. Next, a vacuum treatment at 500 mbar was carried out over one minute followed by an incubation for 10 min. The explants were washed twice in 10 ml of infection medium (containing MS salts (Murashige and Skoog, 1962), 100 mg/l caseine hydrolysate, 500 mg/l glutamine, 15 g/l saccharose, 15 g/l glucose, 6.0 mg/l 2.4 D, pH 5.2, 200 µM acetosyringone) and co-cultivated overnight at 22° C. After 14-16 h, the explants were again washed several times in infection medium and finally transferred to solid co-cultivation medium (infection medium supplemented with 3.0 g/l phytagel), keeping the scutellum side directed upwards. The explants were cultivated for two more days and then transferred to solid callus-inducing medium which had been enriched with 150 mg/l of timentin to inhibit the growth of agrobacteria.

After 14 days, the calluses were transferred onto selective regeneration medium (containing MS salts (Murashige and Skoog, 1962), 100 mg/l caseine hydrolysate, 500 mg/l glutamine, 30 g/l saccharose, pH 5.8, 5.0 g/l agarose type I, 150 mg/l timentin, 30 mg/l paromomycin). After a further three weeks, the calli were transferred into suitable cultivation receptacles which contained selective regeneration medium with 50 mg/l of paromomycin sulphate for shoot lengthening.

The vector pYFrfp1 (FIG. 6) containing the restoration gene rfp1b (SEQ ID NO: 1) under the control of the ubiquitin promoter from maize with the first intron and the 35-S terminator inserted into the vector pPZP111 were introduced by electroporation (Mersereau et al., 1990. "Efficient transformation of *Agrobacterium tumefaciens* by electroporation." Gene 90.1: 149-151) into the *agrobacterium* strain AGLO (Lazo et al., 1991. "A DNA transformation-competent *Arabidopsis* genomic library in *Agrobacterium*." *Nature Biotechnology* 9.10 (1991): 963-967). An AGLO (pYFrfp1) culture was cultivated overnight in 50 mg/l LB medium to saturation (OD660 2-2.5). 2 ml was centrifuged at 5000 rpm for 5 min and the pellet was dissolved in 1 ml of LB medium as well as 1 ml of infection medium. Prior to infection of the implants, the bacteria were incubated for approximately two hours (OD660 1.5-2.0).

In order to analyse the tDNA, the binding region of the tDNA border and the rye genome was amplified using inverse PCR (Ochman et al., 1990. "Amplification of flanking sequences by inverse PCR." *PCR protocols: A guide to methods and applications:* 219-227). To this end, the DNA of the transgenic rye plants was digested with BamHI or BglII, circularized with T4 DNA-Ligase and then used as the template for the PCR. The amplification was carried out in the context of a nested PCR with the GeneAmp-PCR System 9700 (Perkin Elmer). The reaction conditions corresponded to those recommended by the manufacturer, wherein 200 ng of template DNA was used in the first reaction and 0.5 µl from the first reaction was used as the template for the second reaction, so that the final volume was 25 μl.

For the right border (RB) for the first reaction (28 cycles at 94° C. for 30 s, 48° C. for 60 s and 72° C. for 2 min), the following primers were used: RB1R 5'-CTG AAT GGC GAA TGC TAG AGC AG-3' (SEQ ID NO: 25) (LacZ region) and UBIF 5'-CTG CAG TGC AGC GTG ACC CG-3' (SEQ ID NO: 26) (3' region of maize ubiquitin promoter). For the second reaction (32 cycles at 94° C. for 30 s, 52° C. for 60 s and 72° C. for 2 min) the following primers were used: RB2R 5'-CGT TTC CCG CCT TCA GTT TAA AC-3' (SEQ ID NO: 27) and UBIF primer. PCR amplification products with blunt ends were obtained in which two DNA polymerase was added to the second reaction mixture. These amplification products were cloned into the PCR vector (Invitrogen, San Diego, Calif.) and then a sequence analysis was carried out on it.

Successfully transformed rye plants were propagated and crossed with Pampa male sterile inbred lines. Descendants which carried and expressed the restoration gene rfp1b as a transgene exhibited a restoration of male sterility.

As an alternative to the transgenic approach described above, the gene function can also be produced by knockout of the restoration gene in a restorer line. To this end, the person skilled in the art could, for example, also employ TILLING or genome editing (for example TALENs or CRISPR/Cas) in order, for example, to introduce an early stop codon into the coding sequence or to displace the reading frame by insertion/deletion. The result would be a non-functional mTERF protein and a loss of restoration capability.

Example 8: Characterization of Plant Material with Regard to Pollen Shedding The above results now enable a plant breeder to use the desired restoration for Pampa CMS together with an excellent pollen shedding in the development of new cereal plants, in particular rye and barley. During the course of this, negative agronomic traits on the yield have been significantly reduced and the risk of ergot infestation has simultaneously been minimized. The degree of pollen shedding which is obtained with a male pollen parent in accordance with the invention can be determined on a scale of 1 to 9 (Geiger H H, Morgenstern K (1975) Angewandt-genetische Studien zur cytoplasmatischen Pollensterilitat bei Winterroggen [Applied genetic studies on cytoplasmic pollen sterility in winter rye]. Theor Appl Genet 46:269-276). In this regard, values of 1 to 3 mean non-dehiscent, empty anthers with a small amount of degeneration; values of 4 to 6 indicate a partially removed male sterility with <10% to >50% fertile anthers; values from 7 to 8 denote pollen-shedding anthers with increased anther size; and a value of 9 corresponds to a completely male-fertile plant like that expected in normal cytoplasm. Test crossings produced plants in accordance with the invention which had a value of 7 or higher, preferably even a value of 8 or higher or, almost regularly, a value of 9.

In Germany, ergot susceptibility of new rye varieties has been tested in field trials with artificial inoculation over several years and in different locations. The evaluation of the ergot susceptibility in this regard is based on a score system of 1 (very slightly susceptible) to 9 (very strongly susceptible). As can be seen in Table 3, hybrid varieties which carry a restoration gene from the donors IRAN IX, Pico Gentario or Altevogt 14160 (#1-#4), because of the excellent pollen shedding, exhibit a significantly reduced infestation with ergot pathogens (*Claviceps purpurea*).

TABLE 3

Stages of expression for ergot susceptibility for four hybrid varieties which carry restoration genes for the donors IRAN IX, Pico Gentario or Altevogt 14160 (left hand half; #1 to #4) and for four hybrid varieties with other restoration systems (right hand half).

| Hybrid varieties which carry restoration genes from donors IRAN IX, Pico Gentario or Altevogt 14160 | Value | Hybrid varieties with other restoration genes or restoration systems | Value |
|---|---|---|---|
| Visello | 3 | SU Drive | 6 |
| Minello | 4 | SU Forsetti | 5 |
| Palazzo | 4 | SU Performer | 6 |
| KWS Bono | 4 | SU Mephisto | 6 |

In the context of the particular harvest results, the MRI (Max Rubner-Institut, Bundesforschungsinstitut für Ernährung and Lebensmittel [Federal Research Institute for Nutrition and Foodstuffs]) regularly collates ergot infestation data from the rye harvest in German agriculture. An evaluation of this data shows that the occurrence of ergot can be more than halved if, instead of hybrid varieties with a stage of expression of 5 to 6, varieties are used which, with a stage of expression of 3-4, are significantly less susceptible as regards ergot.

Example 9: Structural Comparison of rfp1a and rfp1b on a DNA and Amino Acid Level Structural comparisons of rfp1a and rfp1b on a DNA (Table 4) and amino acid level (Table 5) show a comparatively high agreement between non-restoring wild type and restoring IRAN9. Surprisingly, however, rfp1a and rfp1b from IRAN9 exhibit a very low agreement with only 76% on a DNA level and only 66% or 68% on a protein level, although both have a restoration-mediating action. This shows that the tendency of mTERF proteins to restore male fertility is possible over a wide structural variability.

TABLE 4

Comparison of identities of cDNAs of rfp1a and rfp1b

| | | rfp1a | | rfp1b | |
|---|---|---|---|---|---|
| | | Wild type | Iran9 | Wild type | Iran9 |
| rfp1a | Wild type | — | 97% | 76% | 76% |
| | Iran9 | | — | 76% | 76% |
| rfp1b | Wild type | | | — | 95% |
| | Iran9 | | | | — |

TABLE 5

Comparison of identities of cDNAs of rfp1a and rfp1b

| | | rfp1a | | rfp1b | |
|---|---|---|---|---|---|
| | | Wild type | Iran9 | Wild type | Iran9 |
| rfp1a | Wild type | — | 96% | 67% | 68% |
| | Iran9 | | — | 66% | 67% |
| rfp1b | Wild type | | | — | 90% |
| | Iran9 | | | | — |

Example 10: Detection of Restoration Capability of rfp1a and rfp1b Genes Alone and in Combination as Well as from Different Sources Table 6 clearly shows that test crossing plants which are equipped with only one copy, rfp1a or rfp1b, have a slightly smaller but on the whole entirely sufficient pollen shedding and anther size when compared with plants which have both copies.

TABLE 6

Anther score, according to Geiger & Morgenstern (1975), of test cross plants (Tx . . .) with different rfp1 copy configurations:

| Test crosses | rfp1 copy configuration | Mean of restored test cross plants | |
|---|---|---|---|
| | | Anther score | Anther length (mm) |
| TxBC7(Lo310) 1120 | rfp1a | 8 | 7 |
| TxBC7S1(Lo310) 3308 | rfp1a | 8 | 7 |
| TxBC6S1(Lo310) 455 | rfp1b | 8 | 7 |
| TxBC6S1(Lo310) 217 | rfp1a and rfp1b | 9 | 8 |
| TxBC6S1(Lo310) 765 | rfp1a and rfp1b | 9 | 8 |
| TxBC4(Lo316xIRAN IX) | rfp1a and rfp1b | 9 | 8 |
| TxBC2(Lo316xAltevogt) | rfp1a and rfp1b | 9 | 8 |
| TxLo310 (original line) | — | | 3 |

The invention claimed is:

1. A plant of the genus *Secale* suitable, as a male pollen parent, for restoring the pollen fertility for the Pampa cytoplasmic male sterility (CMS), wherein
   a) in the plant or in a hybrid plant from a cross with a female CMS parent, a linkage drag effect on the yield otherwise coupled with the restoration property is less than 7 quintals per hectare (dt/ha) compared with a corresponding near-isogenic plant or hybrid plant which does not contain the chromosomal segment or the nucleic acid molecule as defined in b), and
   b) the plant comprises a chromosomal segment which has at least one introgressed nucleic acid molecule which is capable of mediating the restoration property, and the at least one introgressed nucleic acid molecule has a nucleotide sequence which is selected from the group consisting of:
   (i) a nucleotide sequence comprising SEQ ID NO: 28,
   (ii) a nucleotide sequence which codes for the amino acid sequence of SEQ ID NO: 29,
   (iii) a nucleotide sequence which is complementary to a nucleotide sequence in accordance with (i) or (ii),
   (iv) a nucleotide sequence which has an identity of at least 99% with the nucleotide sequence in accordance with (i) or (ii),
   (v) a nucleotide sequence which codes for an amino acid sequence which has an identity of at least 99% with SEQ ID NO: 29, and
   (vi) a nucleotide sequence which codes for an amino acid sequence which, compared with the amino acid sequence shown in SEQ ID NO: 29, exhibits discrepancies in the amino acid sequence in the form of conservative amino acid mutations.

2. The plant as claimed in claim 1, wherein the chromosomal segment is an interval between the marker loci tc256739, ctg32 or ctg24met2a5 and tc300731 or 7_01_H 1441 on chromosome 4R from a donor selected from the group consisting of IRAN IX, Pico Gentario and Altevogt 14160.

3. The plant as claimed in claim 1, wherein the chromosomal segment has one or more of the following marker loci of the donor: ctg2, P20, 72F13_c2_mTERF or ctg16b.

4. The plant as claimed in claim 1, wherein the chromosomal segment is characterized by the absence of one or more of the following marker loci of the donor: 7_01_H_1441, ctg24met2a5 or ctg32.

5. The plant as claimed in claim 1, wherein the chromosomal segment is no larger than 190 kb.

6. The plant as claimed in claim 1, wherein the plant is an inbred plant, a plant, a double haploid plant or a hybrid plant.

7. The plant as claimed in claim 1, which has an enhanced resistance against a pathogen.

8. A seed or descendant of the plant as claimed in claim 1, wherein the seed or the descendant comprises the chromosomal segment.

9. An organ, plant portion, tissue or cell of the plant as claimed in claim 1.

* * * * *

```
                        SEQUENCE LISTING

<160> NUMBER OF SEQ ID NOS: 33

<210> SEQ ID NO 1
<211> LENGTH: 1146
<212> TYPE: DNA
<213> ORGANISM: Secale cereale

<400> SEQUENCE: 1
atgctcctcc tcctccggca gcgcgtcctc tccgctgcgc catctccttc cacctcccca      60
ctcctctctc tccaccgcct cctctgcgcc gccgcgcccg tcaaccctag cttcgccgtc     120
gacgactacc tcgtcggcac ctgcgcctc  agccgtgccc aggcactcaa ggcatccgcc     180
aagctgtccc acctcaagtc ccccgccaac cccgacgccg tcctcgcctt cctcgccgga     240
ctcggcctct ccggcgccga tgtggcggcc gtcgtcgcca aggatcccaa gttcctctgc     300
gccggcgtgg agacaaccct ggcccccgtc gtcgctgggc tcaccggcct gggtctgtca     360
aatgctgaga ctgcgcgcct cgtctcgctt gcccccgaca aattccgcca gagatccatc     420
gtctccaagc tagactacta cctgccgctc ttcggctcca tcgacaactt ggtccggtcg     480
ctcaaacacg gcgccggcat cctcggctcc gacctcgaga gggtggtcaa gcccaatgtt     540
agtctcctag cagagtgcgg gctaggtgct tgtgatattg ccaagctgtt cgtccaaata     600
ccgaggatgc tgtgtgctaa accagagcgt gtcctggaga tggttgcgtg tgccgaaagt     660
ataggtgtgc cccgtggctc tggaatgttc aggcacgcgc tgcacgctgt ctcatacttc     720
agcgacgaca agctcaccgc taaagtggac tacttgaaga agacatttag gtggtcggat     780
gccgaggttg ccattgctgt gtccaagggt ccatttctgc tgaggaggtc aaaggatatt     840
ctgaagcaca gctccgagtt ccttatcact gaggtagggt tgcagccggc ctacattgct     900
catcggccgg ctatgctcac ttacagcctg gagggccggc tcaggccccg ctactatgtt     960
gtgagatttc tcaaggaaaa tggattgcta gagcacgggc ggagctacta tacaacactg    1020
attagtactg agaaggtttt catggaaaag ttcatacgcc ctcacaagga agccgcacca    1080
cacctcgctg aagactacgc ggctgcttac aaaggacaag tgccggctag attcagattt    1140
acatga                                                               1146

<210> SEQ ID NO 2
```

<211> LENGTH: 381
<212> TYPE: PRT
<213> ORGANISM: Secale cereale

<400> SEQUENCE: 2

Met Leu Leu Leu Leu Arg Gln Arg Val Leu Ala Ala Pro Ser Pro
1               5                   10                  15

Ser Thr Ser Pro Leu Leu Ser Leu His Arg Leu Leu Cys Ala Ala Ala
            20                  25                  30

Pro Val Asn Pro Ser Phe Ala Val Asp Asp Tyr Leu Val Gly Thr Cys
            35                  40                  45

Gly Leu Ser Arg Ala Gln Ala Leu Lys Ala Ser Ala Lys Leu Ser His
    50                  55                  60

Leu Lys Ser Pro Ala Asn Pro Asp Ala Val Leu Ala Phe Leu Ala Gly
65                  70                  75                  80

Leu Gly Leu Ser Gly Ala Asp Val Ala Ala Val Ala Lys Asp Pro
                85                  90                  95

Lys Phe Leu Cys Ala Gly Val Glu Thr Thr Leu Ala Pro Val Val Ala
                100                 105                 110

Gly Leu Thr Gly Leu Gly Leu Ser Asn Ala Glu Thr Ala Arg Leu Val
            115                 120                 125

Ser Leu Ala Pro Asp Lys Phe Arg Gln Arg Ser Ile Val Ser Lys Leu
    130                 135                 140

Asp Tyr Tyr Leu Pro Leu Phe Gly Ser Ile Asp Asn Leu Val Arg Ser
145                 150                 155                 160

Leu Lys His Gly Ala Gly Ile Leu Gly Ser Asp Leu Glu Arg Val Val
                165                 170                 175

Lys Pro Asn Val Ser Leu Leu Ala Glu Cys Gly Leu Gly Ala Cys Asp
                180                 185                 190

Ile Ala Lys Leu Phe Val Gln Ile Pro Arg Met Leu Cys Ala Lys Pro
        195                 200                 205

Glu Arg Val Leu Glu Met Val Ala Cys Ala Glu Ser Ile Gly Val Pro
210                 215                 220

Arg Gly Ser Gly Met Phe Arg His Ala Leu His Ala Val Ser Tyr Phe
225                 230                 235                 240

Ser Asp Asp Lys Leu Thr Ala Lys Val Asp Tyr Leu Lys Lys Thr Phe
                245                 250                 255

Arg Trp Ser Asp Ala Glu Val Ala Ile Ala Val Ser Lys Gly Pro Phe
                260                 265                 270

Leu Leu Arg Arg Ser Lys Asp Ile Leu Lys His Ser Ser Glu Phe Leu
            275                 280                 285

Ile Thr Glu Val Gly Leu Gln Pro Ala Tyr Ile Ala His Arg Pro Ala
    290                 295                 300

Met Leu Thr Tyr Ser Leu Glu Gly Arg Leu Arg Pro Arg Tyr Tyr Val
305                 310                 315                 320

Val Arg Phe Leu Lys Glu Asn Gly Leu Leu His Gly Arg Ser Tyr
                325                 330                 335

Tyr Thr Thr Leu Ile Ser Thr Glu Lys Val Phe Met Glu Lys Phe Ile
            340                 345                 350

Arg Pro His Lys Glu Ala Ala Pro His Leu Ala Glu Asp Tyr Ala Ala
                355                 360                 365

Ala Tyr Lys Gly Gln Val Pro Ala Arg Phe Arg Phe Thr
    370                 375                 380

<210> SEQ ID NO 3
<211> LENGTH: 3870
<212> TYPE: DNA
<213> ORGANISM: Secale cereale

<400> SEQUENCE: 3

```
aggagatcga ccaagtatgg tggcttttct gtactacacg tgattctaaa ggctctgtta      60
gttgatgatg cgctgatact tgctcctatt gtcctagaga ttgtatgtaa actcctaaat     120
atgttacccc tggtgcatgt attgttctgt ggttaaaggt aattaaacaa cccaatgtgc     180
tcgtgtaatt gctattcctt tcgagtcatc attagcaaat gttccaacta cacttgatat     240
atattataat tgtactagaa atgatgaata atatacccag ttcattctgg aatggcaaa      300
tccaaaataa gcagtgagtg gacgtacaca actatcttat ttgcagccaa atcaggggc      360
atcaataaat gttgtttaac atgccagatc cagtcaaata cagtgaaaat tcggatatct     420
gcttaagaaa aagggctaaa tggtgttagt ttctgttgca ggtatcaaca ctgaacctga     480
tacttgcatg ataatttact tccacactag aacagctttt tctatgcact gactctggaa     540
tagaaactca tgctctgaac ttttcattta tacactgaga aacttctggt gttataaata     600
ttctttattt ttactctacc tttgtgagca ctgttttgta atgggtcatc gcttcaccaa     660
caaagctgct tcttacttga cagttggatt tagcagcagc taatgcatgt aatttcttat     720
tattttata gaaaagccgc aaatgctcga ggagctatgt gtaacatgtg aattatgtgt      780
tttcatattc atttgtacaa tgagtcaacc atgcacgcca tcaattcttt tctggagttg     840
ataatcgaat gtaaaaaaca tattatctcc tttccattca tattaatggc atggaagcaa     900
ttagatgcag aatttacagc ggctagataa ttgattgtaa tttactccct ccgtcctta      960
aaaagtgtaa ttccaacttt gttggagggt caaactatct caatgtttga ccgagtttgt    1020
gcaaaaatat atcagcggct gcggttgcgg ttgtgggctt atcgttggag caaccgagca    1080
gtcctttctg attgttttgc tcctcgtggg tggtttttca ggcttccttt ttgggtaaat    1140
ttttaccttt ttaggttttc aggcttcttg caaagcaatt tcgtttgaaa aaaaaaagaa    1200
gagagcctgc tttgagatct ggcgatgcaa atgccaggga ccaaagccac cgctgctgtc    1260
aggctgcaga cgcaaggtta catggtcgct ggaggagaga cattggtttc agccatggcg    1320
gcgcgagctt gctcacgcac tctgaagatg cagggggaag atcagcgtta tacgtacaat    1380
cgagcgtcgc tatttggtgc agttggccgc tgtttggggg gtgaggaagg ttagatgaat    1440
gtgtaatggc tgggcttttt cgaaccctgt ctgaactctg aagagggccc gaaactatgt    1500
ttaaaccctg ctgtcgtgcg cggtatgctt catttctgtt ctaggacggt gctgattcat    1560
ggtgctggga gggtatgcga gattgatatg ttttatata tagcccggtc gctgctgatt    1620
gatttgaaaa ttgttggccg gtcaaaatcg taaaccatat ccaaaataga atacctcatt    1680
tggataaaga gcttcaaaat tagggaacat agtgaattaa acaattgaa tgggagagct    1740
tgacaaattg ttgatccggt caaaattgaa tggcccaatt ctaaattgaa tactttaatt    1800
aatcgatcca aataagccat ggtgttatcg aagatgaaaa ggcttatggg tgagccgacc    1860
tcaaagtttt ttgtacctca tggtgatttg agttttttga aacagccgac cccaaagttg    1920
ataggtactc ctattagtga aaaaaattgg ttttatgcat ttcacatttc agttcagttt    1980
tatgcatttg gataaattat tatttgtatt aatgttgttc cgatgttcta gaaatgttgg    2040
actactcatt cggtgataaa gccggtcctg gagaaggcaa gctaatggat caccgtcctc    2100
tgaagttgaa taaagatgac tatgagcgcg ttaagcgaat accatttgag aaggtaggtg    2160
```

```
gctggatttt tccaaatgtt tcttgcgtga ttactctttt ttccctatgt gaaaattttg    2220
aattctcgct tagggagcca acttccgtga cctggaaggc gtgagagtaa ggccaaacaa    2280
catcgctgag tttgaccccg agattccacg agtttacctt gagtctggca atccattggt    2340
acgtgtcgta ccgcccgccc aatatcgtca gggcttttct agtcacaatt tctgaagatt    2400
gcatgtctgt atggccaggt ccccgaatat gcaataaagt tcaggagtgg caagtctctc    2460
aggttagtag tgccttatgt tccctgtctt cttttctgaa actatatagg ccgtttggac    2520
ggctgtggtg ggacgagacg gttcctacag tggtaaccag cgcaaggccg catagccagg    2580
tcagctttct cacaagctgc ctcagttttc tgatctgacc atttaggaag cacacaacca    2640
tttgttcagt ttcgacagtg tcaggtccag aatcctctaa acacgtttcg tgttgctgcc    2700
tgcaggccat actacacccg agccaggcct tttttataag ggttgctgcc tgaaggagtt    2760 ggacatttt ataagggttc ctctttcaga tgctattgga gcttgacaag tggctcctcc    2820
tccgctgccc accttgcgtc aggcgcgcac actcgtgagc actgtgaata gtcgacacta    2880
caccttcacc ctaatccacg attctataca taagtggttt tgttgctagg ggtgggccgc    2940
ccaaatctcc tcttgtggtt tctcagcctt ttgcggcgac aatgacggtg ttgagcgatg    3000
tgtcgtgttt gtctatcgaa gttggagttt ccttttctttt ttgtatgcct cattttagcg    3060
gcgatttggt gccactgtta cgaggttctt tgcatttcgt tgaggaccaa atacgatgat    3120
attgtggtag tgtcaatgct ccccacttct tgtagtgtgt tttcaaaagc aggtttccga    3180
gtgccagcgt ggctttgacg atggtttccg ttcattttct ttattaaccc gacaaccgcc    3240
ttcttctaat accaccgcag aacttccgcc ctatactttt cggttttgtg tctcccaaaa    3300
aattgtcatg tataacaaat gttgaacaaa ttatgaatgg gaaacgcttc ttatcatacg    3360
tctgatacga agcaaacttc aaacctgtcg ccgccgccct accgatttc tttattaact    3420 actaggcaac tcccttcttc gcaaaaacaa aacaaacaaa acaaacaag gcaactccct    3480 tcttataata ctacaacgga gccggagcgg cagaaatctc gccccggttg atgatttta    3540 tcgaagaaaa cagttttct tatggatata gaattttct tgaccggtat gaataataga    3600 tgttttcta gggtggggtg tgcataatag atgttttgc gtgctagtta tatttgggtt    3660
ctgatagact cttggcaacg cgtggatgga aatgcgccgt tggatgtcat ttggatggca    3720
gggattaata atacacttca actcagccaa gttcacttca tttggatgac aagtccgtcc    3780
accacaccac cggagacaca ctcaacgcca ctcgaattcc ccaccgcccg ccgccgcccg    3840
ccgccgccgc tgttccgccg tcgcggcgcc                                    3870
```

```
<210> SEQ ID NO 4
<211> LENGTH: 20
<212> TYPE: DNA
<213> ORGANISM: Artificial Sequence
<220> FEATURE:
<223> OTHER INFORMATION: ctg2 Forward Primer

<400> SEQUENCE: 4
cagcctctgg ttgttgaggt                                                   20

<210> SEQ ID NO 5
<211> LENGTH: 20
<212> TYPE: DNA
<213> ORGANISM: Artificial Sequence
<220> FEATURE:
<223> OTHER INFORMATION: ctg2 Reverse Primer
```

```
<400> SEQUENCE: 5
catcgccact gcaaagttta                                               20

<210> SEQ ID NO 6
<211> LENGTH: 19
<212> TYPE: DNA
<213> ORGANISM: Artificial Sequence
<220> FEATURE:
<223> OTHER INFORMATION: P20 Forward Primer

<400> SEQUENCE: 6
tgtcgaaact gaacaaatg                                                19

<210> SEQ ID NO 7
<211> LENGTH: 20
<212> TYPE: DNA
<213> ORGANISM: Artificial Sequence
<220> FEATURE:
<223> OTHER INFORMATION: P20 Reverse Primer

<400> SEQUENCE: 7
ggagccaact tccgtgacct                                               20

<210> SEQ ID NO 8
<211> LENGTH: 21
<212> TYPE: DNA
<213> ORGANISM: Artificial Sequence
<220> FEATURE:
<223> OTHER INFORMATION: 72F13_c2_mTERF Forward Primer

<400> SEQUENCE: 8
tcgtcgccaa ggatcccaag t                                             21

<210> SEQ ID NO 9
<211> LENGTH: 22
<212> TYPE: DNA
<213> ORGANISM: Artificial Sequence
<220> FEATURE:
<223> OTHER INFORMATION: 72F13_c2_mTERF Reverse Primer

<400> SEQUENCE: 9
actttagcgg tgagcttgtc gt                                            22

<210> SEQ ID NO 10
<211> LENGTH: 22
<212> TYPE: DNA
<213> ORGANISM: Artificial Sequence
<220> FEATURE:
<223> OTHER INFORMATION: ctg16b Forward Primer

<400> SEQUENCE: 10
ctccaagaac tctttctcgg tc                                            22

<210> SEQ ID NO 11
<211> LENGTH: 22
<212> TYPE: DNA
<213> ORGANISM: Artificial Sequence
<220> FEATURE:
<223> OTHER INFORMATION: ctg16b Reverse Primer

<400> SEQUENCE: 11
cccaatatga agctcctagc ag                                            22

<210> SEQ ID NO 12
```

```
<211> LENGTH: 23
<212> TYPE: DNA
<213> ORGANISM: Artificial Sequence
<220> FEATURE:
<223> OTHER INFORMATION: 7_01_H_1441 Forward Primer

<400> SEQUENCE: 12
ggtcatatga agacaccatg tca                                              23

<210> SEQ ID NO 13
<211> LENGTH: 22
<212> TYPE: DNA
<213> ORGANISM: Artificial Sequence
<220> FEATURE:
<223> OTHER INFORMATION: 7_01_H_1441 Reverse Primer

<400> SEQUENCE: 13
tttcgccatt ttcgaagtag tc                                               22

<210> SEQ ID NO 14
<211> LENGTH: 20
<212> TYPE: DNA
<213> ORGANISM: Artificial Sequence
<220> FEATURE:
<223> OTHER INFORMATION: ctg24met2a5 Forward Primer

<400> SEQUENCE: 14
aaagagtaca acggtcacag                                                  20

<210> SEQ ID NO 15
<211> LENGTH: 24
<212> TYPE: DNA
<213> ORGANISM: Artificial Sequence
<220> FEATURE:
<223> OTHER INFORMATION: ctg24met2a5 Reverse Primer

<400> SEQUENCE: 15
gaagaatcct cgctatcttt agac                                             24

<210> SEQ ID NO 16
<211> LENGTH: 20
<212> TYPE: DNA
<213> ORGANISM: Artificial Sequence
<220> FEATURE:
<223> OTHER INFORMATION: ctg32 Forward Primer

<400> SEQUENCE: 16
ccgaggaaag aagccaagag                                                  20

<210> SEQ ID NO 17
<211> LENGTH: 20
<212> TYPE: DNA
<213> ORGANISM: Artificial Sequence
<220> FEATURE:
<223> OTHER INFORMATION: ctg32 Reverse Primer

<400> SEQUENCE: 17
ccttgagaat ccgatccacc                                                  20

<210> SEQ ID NO 18
<211> LENGTH: 20
<212> TYPE: DNA
<213> ORGANISM: Artificial Sequence
<220> FEATURE:
<223> OTHER INFORMATION: c40745_1 Forward Primer
```

-continued

```
<400> SEQUENCE: 18
gtcgctgctg attgatttga                                              20

<210> SEQ ID NO 19
<211> LENGTH: 20
<212> TYPE: DNA
<213> ORGANISM: Artificial Sequence
<220> FEATURE:
<223> OTHER INFORMATION: c40745_1 Reverse Primer

<400> SEQUENCE: 19
cgttgtttgg ccctactctc                                              20

<210> SEQ ID NO 20
<211> LENGTH: 18425
<212> TYPE: DNA
<213> ORGANISM: Secale cereale - 175019-N3_c9

<400> SEQUENCE: 20 gattttttt  caaaactgtg cctaaattta  acaaaattt gaaaactgtt  agtctgttag    60
agaaaaaatc gaatctatga  ccccgtcggc cacgactggg  ccgaccagcc agccgtcggc   120
ctcggctggg ccgaccaggg gcccgtcggc ctcgccctgg ccgaccagtg gcccgtcggc   180
ctcgctctgg ccgaccagtg cccgtcggcc tggcagcggc cgctcggctc gtcctgtggc   240
cgaacacgag ctaacaacag ccggatcaat ttaacaaaga caagaaaagc tgctgctggt   300
gctgcatcgg tttggttgta ctagttggtg ttgtcacgct gagccggagg tgcaattccg   360
tccacaaaca gagttaggaa aagcgaccac cgtcagccgg tctgccggtg cacgcacgta   420
cgcatgcgcc gaccaggaga attaaaggag aatctgaggc ggagaaaggc tgcgatgcaa   480
cgtgaggacg gtttcttgga tcagaccaga gcccatggtt tctccagttc tcatgcagtt   540
cccgccaatg gagcagtttg attgaggtgc atgcatgaac gtgatggctg actcggattc   600
ttgtgcgctt cctgttggcc tttgattgct tgtcacttct tatggatcgc tccacacgta   660
cgctgcatcg gagtggctct tgttggcatc caaactttga gctggatcca acagatactc   720
aaacgtactt atccagccgc cgctcggccg ctgccaggcc gacgggcact ggtcggccag   780
ggcgaggccg acgggccact ggtcggccag ggcgaggccg acgggcccct ggtcggccca   840
gccgaggccg acgctggct ggtcggccca gtcgtggccg agaggccgcc tttcggccca    900
gttaaggccg acggggtcat agattcgatt ttttctctaa cagactaaca gttttcaaat   960
tttgtataaa tttaggcaca gttttgaaaa aaatcgaaa tatgtgtatt agtattcgag   1020
agatttgttt catatgcata cttgaggaaa gagtgtagga cgacataagg ggccatggcg   1080
atggcctgca cctgcacgcc cgccatggtg ctcatccttc catttctatt gtgatggctt   1140
gcctgcagaa accaatccaa ccacagggt catccaaaaa agaagaaga agaagaagaa   1200 gaagaagaag aggggagggg aggaggatgg agggcgtgcg tgtgtaccdt tgaagtctag   1260
gtgctgcagc ccgtcgcggg cgtcgaggca tccatggcct tcctcgagga ccacgtggat   1320
gatggtgcac cggtgccggt gccgctcctc gatctggggc ctcccctccc ctcccttcc   1380 cttcccttgc tttggagagg aaggaaggtg tcacccatgg ctcgccgtgc cgagttgaat   1440
gcccgccgtc cgtctgccaa gaggagagaa ggagatggcg accgagagga gggaggaagt   1500
gaaggcggcg gcggccttca cttcctcctc tcggtcgaga gagaggaggg acgccaatcc   1560
tgttcgctgt agtccaccca atcccacgct caatgcaatc caccttttctc accgaggcac   1620
```

```
acccgagaca cacactacag aattgggccc gccgggaaag agccccaccc gtcatcggct    1680
gtagcgcgaa atagtaacgt ccagagaaac ccgtcgtaaa aaactgccag cgaggtagat    1740
cgctcgatcc agactctttg cgcacgcagt tgccccagga tggcgggtaa cacagcatgg    1800
tttatatgtt caattaatgc agagtatatc tgcatgctct acatcttgat gttctcagtg    1860
gcaattgcag ctttcaatgc aatactgagt cagtctatct ttccatgaaa aacggttctc    1920
aatatggcca tgaagatgat atgaaatccc aaattcgttg aactattttt gcgggaacaa    1980
ttctggaggg gttgatggcc acaacgtgtt gatcactgct gagtgtgcag ttttgatata    2040
gtctggtggt tgcttcctct agttcttctt atttcttcgc tgaaagtatt cattcttcct    2100
gcagtagctt tgtttataag atattaacag ttgtgaaagc aggtcatcgt tttctagtac    2160
tttgtatctg tcttggatgg cccactggct gatactttt ctgggagcat ctgatctcaa    2220
aactgaatag ttggccagta gcattttgt tgacggccta cccatatagc attacttaat    2280
ggatatatgg aaggccctgg tatttgtact ggagaagcaa attgatgttt gtatggtatg    2340
gtgctgaaaa gcagagggca tttcattcaa tacaagaata tgttaaggta atattaaaaa    2400
gggttatgac attttattct ttattagcac tatctataga tgctcatgac atttttatcc    2460
attggcatat ttgttttggg attgtaaggt gggtcttatg taccattctc tgttttgtac    2520
tttgcacttt tagatgctct tctatatttg ctttagttgt gctggttaca atcacttctg    2580
aagacacgta tgctgcaatt ggagaaaaga gaatgaagat gtcgaagact gttaccttag    2640
cgaagagatg gtcccaggga tgatatctta accaagcttg gtcttaacat tcaaggtatt    2700
gcagtaattt ttttctcag tttataccga atgtcatctc ttcgtacact cttttcagtt    2760
aaatgtcagt ctaggcatgc aagtactatc tgtcagatat atcatagtta cagaatcttg    2820
cagaatttca aacacagaca ttgtagactt gctggtggtc ctcaaattaa gaatcaagtc    2880
gtgtgggggg aggatggtgc acatttgttt cctgaggtca ggctatagaa atcggaagaa    2940
atgagatatc agctgtgtgc tcccagtaag acaacggaga tgggcacatg ctattattgg    3000
caaagagctc gtatttggaa tgaagatcaa ttgtgtgtct cttctctcgt gcctagttta    3060
gcttttggga attatcgaaa caagattaat gcaatgcagg cgaggggaag agtcgattga    3120
tgaacgaagc gacttgccag gtgaatatat gcattttttt tttcgaaaaa attactttcc    3180
tcaagtaaga attggctggg aaattaagag gagcatactg attgatttac tgaatgttat    3240
agatcaatgg tgctttcttt ctacctagac aagaagtgat tctttcttct ttctaggaga    3300
tcgaccaagt atggtggctt ttctgtacta cacgtgattc taaaggctct gttagttgat    3360
gatgcgctga tacttgctcc tattgtccta gagattgtat gtaaactcct aaatatgtta    3420
cccctggtgc atgtattgtt ctgtggttaa aggtaattaa acaacccaat gtgctcgtgt    3480
aattgctatt cctttcgagt catcattagc aaatgttcca actacacttg atatatatta    3540
taattgtact agaaatgatg aataatatac ccagttcatt ctgggaatgg caaatccaaa    3600
ataagcagtg agtggacgta cacaactatc ttatttgcag ccaaaatcag gggcatcaat    3660
aaatgttgtt taacatgcca gatccagtca aatacagtga aaattcggat atctgcttaa    3720
gaaaaagggc taaatggtgt tagtttctgt tgcaggtatc aacactgaac ctgatacttg    3780
catgataatt tacttccaca ctagaacagc ttttctatg cactgactct ggaatagaaa    3840
ctcatgctct gaacttttca tttatacact gagaaacttc tggtgttata aatattcttt    3900
atttttactc taccttgtg agcactgttt tgtaatgggg catcgcttca ccaacaaagc    3960
tgcttcttac ttgacagttg gatttagcag cagctaatgc atgtaatttc ttattatttt    4020
```

```
tatagaaaag ccgcaaatgc tcgaggagct atgtgtaaca tgtgaattat gtgttttcat   4080
attcatttgt acaatgagtc aaccatgcac gccatcaatt cttttctgga gttgataatc   4140
gaatgtaaaa aacatattat ctcctttcca ttcatattaa tggcatggaa gcaattagat   4200
gcagaattta cagcggctag ataattgatt gtaatttact ccctccgtcc tttaaaaagt   4260
gtaattccaa ctttgttgga gggtcaaact atctcaatgt ttgaccgagt ttgtgcaaaa   4320
atatatcagc ggctgcggtt gcggttgtgg gcttatcgtt ggagcaaccg agcagtcctt   4380
tctgattgtt ttgctcctcg tgggtggttt ttcaggcttc ttttttgggt aaattttttac  4440 cttttttaggt tttcaggctt cttgcaaagc aatttcgttt gaaaaaaaaa agaagagagc   4500
ctgctttgag atctggcgat gcaaatgcca gggaccaaag ccaccgctgc tgtcaggctg   4560
cagacgcaag gttacatggt cgctggagga gagacattgg tttcagccat ggcggcgcga   4620
gcttgctcac gcactctgaa gatggcaggg gaagatcagc gttatacgta caatcgagcg   4680
tcgctatttg gtgcagttgg ccgctgtttg ggggtgagg aaggttagat gaatgtgtaa    4740
tggctgggct ttttcgaacc ctgtctgaac tctgaagagg gcccgaaact atgtttaaac   4800
cctgctgtcg tgcgcggtat gcttcatttc tgttctagga cggtgctgat tcatggtgct   4860
gggagggtat gcgagattga tatgttttta tatatagccc ggtcgctgct gattgatttg   4920
aaaattgttg gccggtcaaa atcgtaaacc atatccaaaa tagaataccct catttggata   4980 aagagcttca aaattaggga acatagtgaa ttaaaacaat tgaatgggag agcttgacaa   5040
attgttgatc cggtcaaaat tgaatggccc aattctaaat tgaatacttt aattaatcga   5100
tccaaataag ccatggtgtt atcgaagatg aaaaggctta tgggtgagcc gacctcaaag   5160
ttttttgtac ctcatggtga tttgagtttt ttgaaacagc cgaccccaaa gttgataggt   5220
actcctatta gtgaaaaaaa ttggttttat gcatttcaca tttcagttca gttttatgca   5280
tttggataaa ttattatttg tattaatgtt gttccgatgt tctagaaatg ttggactact   5340
cattcggtga taaagccggt cctggagaag gcaagctaat ggatcaccgt cctctgaagt   5400
tgaataaaga tgactatgag cgcgttaagc gaataccatt tgagaaggta ggtggctgga   5460
tttttccaaa tgtttcttgc gtgattactc tttttttccct atgtgaaaat tttgaattct   5520
cgcttaggga gccaacttcc gtgacctgga aggcgtgaga gtaaggccaa acaacatcgc   5580
tgagtttgac cccgagattc cacgagttta ccttgagtct ggcaatccat tggtacgtgt   5640
cgtaccgccc gcccaatatc gtcagggctt ttctagtcac aatttctgaa gattgcatgt   5700
ctgtatggcc aggtccccga atatgcaata aagttcagga gtggcaagtc tctcaggtta   5760
gtagtgcctt atgttccctg tcttcttttc tgaaactata taggccgttt ggacggctgt   5820
ggtgggacga gacggttcct acagtggtaa ccagcgcaag gccgcatagc caggtcagct   5880
ttctcacaag ctgcctcagt tttctgatct gaccatttag gaagcacaca accatttgtt   5940
cagtttcgac agtgtcaggt ccagaatcct ctaaacacgt ttcgtgttgc tgcctgcagg   6000
ccatactaca cccgagccag gccttttttta taagggttgc tgcctgaagg agttggacat   6060
ttttataagg gttcctcttt cagatgctat tggagcttga caagtggctc ctcctccgct   6120
gcccaccttg cgtcaggcgc gcacactcgt gagcactgtg aatagtcgac actacacctt   6180
caccctaatc cacgattcta tacataagtg gttttgttgc tagggtggg ccgcccaaat    6240 ctcctcttgt ggtttctcag ccttttgcgg cgacaatgac ggtgttgagc gatgtgtcgt   6300
gtttgtctat cgaagttgga gtttcctttc ttttttgtat gcctcatttt agcggcgatt   6360
```

-continued

```
tggtgccact gttacgaggt tctttgcatt tcgttgagga ccaaatacga tgatattgtg      6420
gtagtgtcaa tgctccccac ttcttgtagt gtgttttcaa aagcaggttt ccgagtgcca      6480
gcgtggcttt gacgatggtt tccgttcatt ttctttatta acccgacaac cgccttcttc      6540
taataccacc gcagaacttc cgccctatac ttttcggttt tgtgtctccc aaaaaattgt      6600
catgtataac aaatgttgaa caaattatga atgggaaacg cttcttatca tacgtctgat      6660
acgaagcaaa cttcaaacct gtcgccgccg ccctaccgat tttctttatt aactactagg      6720
caactccctt cttcgcaaaa acaaaacaaa caaaacaaaa caaggcaact cccttcttat      6780
aatactacaa cggagccgga gcggcagaaa tctcgccccg gttgatgatt tttatcgaag      6840
aaaacagttt ttcttatgga tatagaattt ttcttgaccg gtatgaataa tagatgtttt      6900
tctagggtgg ggtgtgcata atagatgttt ttgcgtgcta gttatatttg ggttctgata      6960
gactcttggc aacgcgtgga tggaaatgcg ccgttggatg tcatttggat ggcagggatt      7020
aataatacac ttcaactcag ccaagttcac ttcatttgga tgacaagtcc gtccaccaca      7080
ccaccggaga cacactcaac gccactcgaa ttccccaccg cccgccgccg cccgccgccg      7140
ccgctgttcc gccgtcgcgg cgccatgctc ctcctcctcc ggcagcgcgt cctctccgct      7200
gcgccatctc cttccacctc cccactcctc tctctccacc gcctcctctg cgccgccgcg      7260
cccgtcaacc ctagcttcgc cgtcgacgac tacctcgtcg gcacctgcgg cctcagccgt      7320
gcccaggcac tcaaggcatc cgccaagctg tcccacctca gtcccccgc caaccccgac       7380 gccgtcctcg ccttcctcgc cggactcggc ctctccggcg ccgatgtggc ggccgtcgtc      7440
gccaaggatc ccaagttcct ctgcgccggc gtggagacaa ccctggcccc cgtcgtcgct      7500
gggctcaccg gcctgggtct gtcaaatgct gagactgcgc gcctcgtctc gcttgccccc      7560
gacaaattcc gccagagatc catcgtctcc aagctagact actacctgcc gctcttcggc      7620
tccatcgaca acttggtccg gtcgctcaaa cacggcgccg gcatcctcgg ctccgacctc      7680
gagagggtgg tcaagcccaa tgttagtctc ctagcagagt gcgggctagg tgcttgtgat      7740
attgccaagc tgttcgtcca ataccgagg atgctgtgtg ctaaaccaga gcgtgtcctg       7800
gagatggttg cgtgtgccga agtataggt gtgccccgtg gctctggaat gttcaggcac       7860
gcgctgcacg ctgtctcata cttcagcgac gacaagctca ccgctaaagt ggactacttg      7920
aagaagacat ttaggtggtc ggatgccgag gttgccattg ctgtgtccaa gggtccattt      7980
ctgctgagga ggtcaaagga tattctgaag cacagctccg agttccttat cactgaggta      8040
gggttgcagc cggcctacat tgctcatcgg ccggctatgc tcacttacag cctggagggc      8100
cggctcaggc ccgctactac tgttgtgaga tttctcaagg aaaatggatt gctagagcac      8160
gggcggagct actatacaac actgattagt actgagaagg ttttcatgga aaagttcata      8220
cgccctcaca aggaagccgc accacacctc gctgaagact acgcggctgc ttacaaagga      8280
caagtgccgg ctagattcag atttacatga accaagaatg ggctatgaga attggtaaac      8340
tgtgtacggt gcaacaaagt tttcattttg ttgaaagctg gtaattcctg tttcagtgta      8400
ctttgcctaa ctggatgttt gttgtccgct ctgttagatg ctagtatggt ctttgccaac      8460
gcttgatgaa actgatagtt tgaatcctga tatgttagtg ttatcatttg gtagagcaga      8520
aacagtgact tggttatgaa cttgtccatc ctcatgccat gttatttaac acttggaact      8580
aagtaaacaa gaacaggcca ttgtacattc cactaaaatc tctattttaa aaatttaatg      8640
tattctgggt gatgtttgct tgcaccgatg ggcataggtt tgctccgtga ctctgggata      8700
ttcaggcatg ccctgcgcat tgtcgcattc cttggcagga aaaatatagc tgccaaaatg      8760
```

```
gaatacctga agaagacatt caggttgact gatgccgagg gtaagtattc ccgtgtcttt    8820
aaggttctga ttttgttgag gacatccaag gaattggttc agagaaagtt tgagttcctc    8880
atctctgagt tggggttgga acagtcttac gttgcttatc gtccagcaat gttctattgt    8940
gaccaatgtt ctgctgtaaa gacaattaac aaatttaaat gcttactgca cctcaaaggt    9000 tttactttt ggcaccttaa gctggcaagc tttgttttag tgttcttccc tgacaagatg    9060
tttgttatct ggtatggtat gtctgtcgcg tgctagttag gtcattgcta gcacttgatg    9120
aagctagtca ttacatccac gagtcctcat atttcattat aatttttttc tttctgaatg    9180
tcaattctgg accctctttt tgtgaacagt tttggactaa ttgatggtca cagtacgttt    9240
accaatccga ggattctgtt ttgatccagt ttgttagttg cttgttctat aaattgatgg    9300
tcacagtgac tttttggaa gtggttcggc cagtgcgtat atcgcttgga gaatggctga    9360
agaagagtgg tttggctctc tgcctgctat ctatcagtga gcttgtttgg atttcgttca    9420
gtccgagagg aggatgcgga cttgatccag tctgttggtt gctgtgctct agttcgcgtg    9480
acctggaaat cttcggtata tctgccaaac ataaattaag tttaatatcc aagttcagtc    9540
tggaagacat tcaggttgac tgatgccgag ggtatgtatt cctgtgtctt taaggttctg    9600
attttgttga ggacatccaa ggaatcagtt tagcaaaagt ttgagttcct catctctgag    9660
ttggggttgg aataggcttg gagggtaaag tttcttaaga caattaacaa atttaaatgc    9720
ttactgtacc acagaggttt tacttggcac cttaagctgg caacctttgt ttcagtgttc    9780
ttgcctgaca agagttggtt gtcaggtctg gtatgtcttt cacatgctag gttggtcatt    9840
gctaacactt gatgaagcta gtaattggat ccatgagttc tcatatgtcc atatcatcat    9900
atatttgtct ctgaatgtta attctggact ctcttttcg gaacaatttt ggactaattg    9960
atggtcacaa tacatcgatc aatccgagga ttcagttttg atccagtttg tttgttgctt   10020
gttctaattc ctgtgagctg aaaatcttcg ttctttctgc agtatatata tatatatttt   10080
gaaatgatta aatgttgtga aagtaattca tgctttacta gtctgtatca gatttttcca   10140 tatttttct ccagtagtat ttcttaatgg cctatttatt ggctgataca ttcagttcta   10200
gggacaagtt atctcaaaac tgaacaatag agttgtacac tttctattta cggcctacca   10260
tctagtccaa ttaaatgcta tggctggtta aaacaaagcc tcatcaggtt ttcaccaatc   10320
aggcttacat gtgtctgaag ctgtgttgtt atatcatgat cgatgctagc gaatgattga   10380
aataatttat ttctgccttg aatgacctca ggtgttaacc tcgctgttct gtatcatttg   10440
gaaaatgaga aattgtactg gttttcatag gtggctggtg gcaagtgatg aaaactggcg   10500
tcctgcgctt ggagaatggc tgaagaatag tggtttggca ctctgtctgc tatctatcag   10560
tgagcttgtt gggatgtcgg tcagtacata aatcttttgg catttctgcc caacataaat   10620
tttgttggaa ccgtgtgcta tataggtttg ttcggtagta actccccatt tgtgctgctg   10680
cgcatatgtt tgccgtttac atttgcacct tatggtttaa taagacctcc tgctccagca   10740
gcttgtcaaa attcagcacc tatacatgac aatgctgcat ttgtttgttg ttggctgagt   10800
tacataggga gtatgttgtg atagtgattt acagttaacc cttttttgac cccttgctac   10860
catagctttt tctttcaagt cagtagcact catgccatgc gcgattatat aatgtacaat   10920
atctctcaat ttttttggaa gtggttcagt cagtgctgta acaggagggc tcaccttgga   10980
agggcggcga gtattgcttg gggccgtaga gttgtctgtt gcacaactcc cgtgtggtcc   11040
agccgacctc cgggtagcca acccaaccct gcagagaaaa cgaccacctc cttctccatg   11100
```

```
gccggcaaga ctctacatcc ctatgcttga cggagagcgc cgcctggatg ccggagaagg   11160
tgttcacggt caggagctgg tgctcgtggt cgtcgaagat acagccacca tcatgggagg   11220
caatatattt taacaaagag gtcaataaaa agtactccct ccgtcccata atgtaagaca   11280 tttttttgaat ctagtgtagt gtcataaaac atcttacatt atgggacgga ggggtagtta   11340
gcttataact cgttgttaga acatagatca agaatgatgt agtccaagtg tcttgataga   11400
atgcatcaaa attttctatt tataaatttc aacgcaatac aaaatggcct attctcaatt   11460
acatagttcc aggtgttaaa tagcatggca tgatggtctc cccagatgat cactctcttg   11520
gccgggtctt ccgggtggac taggaatgtt ttgtctcctt tgtcggctgg aaagccagat   11580 cttt ccttgg cttgattagt actagcattt ttgcacccgg attggcgaac ctcttgatag   11640
catcgagctt cactgacgct tgtgcgacct caacgagcgt cacgttcgcg acttctgctt   11700
tgagccctct ctcagtgctg ccatgaattg ttatcatggt gctcagagct agcatgatga   11760
gctagaagca cggataggat aggaggatag cgtcatgaaa ttgacgtagg cgccaagaat   11820
gaggcgactt tgaaccagat tatttccgag ctgaagttct cctcgtccca agggataacc   11880
tgccgaccga actatccgag ggggtgcacc tgcaaaacgg tacgagactg tggaagccag   11940
tggtcaaggg gaggaaatga gaccgggaga tcccccatctt ggacagagtg taggggaaga   12000
tgatgtttac gccactttca ccgtctgcca gaactcgggg aaagcagaag ccctcgatga   12060
tcggatctac aaccaaggca aatttcccag atgggaagca taggttgaat gattggttca   12120
ggcaaaggca accgctcgag tctaatcact gcaggtcctc tgttggtaat ggtgcaatca   12180
cttaaaccat gggtcaagtg aatttctgag cccggcgcat gtcagcggct tgaatgatca   12240
tgttgacgcc atggtatcga gtaggatagt gggttgctga aggccctgcg gttggttgtg   12300
accagtgcta ccccacgcga taagggtggt ggaggggtgc agaggcacgt gatcttgcag   12360
cgacgatcaa agaggaactt gagcctccta aagtatattg catcgatgta gggtggcgtg   12420
acgtcacaga gtagcccatg gttttcgacg gtgagctcga aagagccgaa agtgaagatt   12480
tggaatgaca tgtagtcatt tggcatgaac cgagatccta tctgggttca ttctttgact   12540
agtgcagccc ttgccgggtg caccaactaa tagtacgtgg aaatgccaat acccgtagta   12600
tcgtggcgaa cgcagccata agtaccagaa gggattatac acaacaaggt tacccaggtt   12660
cggaccatct gggataggta atatcctatg ccatgcttct aatatgtatt catggtcgag   12720
tacctcatgc aagtgataac aatgaagatg atgtataagc taccgacatt atatttctat   12780
gagagcatat gtgcatacct actcctagac atgtctcata tcgatggcga gggctagggt   12840
ttacagagat caatacgatc tgaggacgcc gccatcttgg cttgtatgcc aagatgatct   12900
cccaatcctt atccaggttc ctgggccgac ccctagggcc gggtcttcct taggcttcct   12960
gggccctggg gccagcttgc tgcctggttc cctccaaaag gccaccctgt tgtgttggac   13020
cgtcaacctc taaagtctaa ggacatgccc tgttactaca tagccaaagc gaccatagta   13080
aggaagacgc tcacatccct gttatcgtac taaacttatt aggtattctg tcaagccagt   13140
gataatataa attggcaaca cttttgggcg aatacaaaat agatgccatg ttcatgacta   13200
accaaacaca caaacttatg ttgaaataaa aggtgtttga ttgtctagtt gtgagcacga   13260
aaactacacc tattgcttcc ataccatcta tggcggccga ggtcgtcctt agtcagtaca   13320
atcactcgac aaagatatca catgaaaata ttgactttta gtggtatctt caatttccaa   13380
atttgatcat taatgccatg tggaaacttt gtgtgtgaaa gcgatgggta cataaattca   13440
atggtgaagg actcattagt agttagattc cagcaaaaca tgatatgtcc ttgtgttacg   13500
```

```
ctaaccgact acaaacggga tagtagattt ttttatgata caagagggtc aggggcggag  13560
ccaggattta gacataggggg ggcgagaccg gcggtaaggc caaattttt tccctcccaa   13620 actagctgct acgttgcacg gatacttgga tacgtatcgg atatgcgata cggggatacg   13680
cccgatacgt cagttttcta aaaacatgga tacggggata cgttcatata tagatgttac   13740
atatattaat tattacaaat atgaagaaaa aattaaggag cttcttggtc aaagcatgcc   13800
tcaatacgat tactcctttc ttttcttgca cttagtccac ttccattaat tggcagtgag   13860
atttgatcag gtttgctgtt caaatcaaat taattattac aaatatgaag aaaaaattaa   13920
ggagcttcta ggtcaaagca tgtctcaata cgattactcc tttcttttct tgcacttagt   13980
ccacttccat taattgacag tgagatttga tcaggtttgc tattcaaatc aatgcatcga   14040
ctctctctta ctcacctttc aattgaataa aaaacattga catacatgtt ttcacatgaa   14100
ctcacgccca tgttgggaat cttcaaaggt gcgtctttat tattgagggg gttttacgtc   14160
gaacgaggga tttcaggtat ccaaaacgga atggctttac agacgacaca gactgcacga   14220
tctgtgaacg ataacactgt acatgcatta gcaaacagaa aaaacaattg cctcctgcat   14280
gtacgcgcgt tgctggcgct gccacatgcg atcgtgcacg catcggctgt aatttcgtcg   14340
tgtgtatagc agctctctat ccaaaacgta tcgcagaagt atcctaggag tatcaaacat   14400
tatttttctt tttttaatat caaaattccg taggatactt acaagatatg tatcgggaag   14460
tatcggggca gtatccggct ggatatggac actttctgaa gtatccgtgc aacgtagact   14520
agctgaagcc aactagtttt acatccgagt acattcatcc ttaactttgc atagacacac   14580
acaacatttt gcatctgaag ccgactagac aaagttgata atcaaactac cctgaaatat   14640
gacatgaaat gtgctgctac aaaacaatat catatgtaca aataagaaaa atcattgtat   14700
aaccgaatga ttggcttta gcttgcattt aaataggttt aaatggcaaa tctgttatgc   14760
aactttgttg ttgtactaaa aaaagatcaa tgttgtcaga atacatacat agagaatcaa   14820
atccagcccc ctactcgtcc cctctaccgc taggtcgacg tagaccggct ggtcgtggtt   14880
ggaaggtgca tgatttcgaa cggttgcttg tgcctgagcg cgacgcgtca caaatcacaa   14940
ccaaaagtta aaatctgatg tataacgaat taatgataca agatgagaat tgtgagagat   15000
tagtagatca ctggttgcag caggaataat tggttgcagc acgaataatt ggcgagtaaa   15060
tcactgaacc agcttgcgtt tacgaatcag atcatgagaa gagatagcag aggcgggcgg   15120
cggcgagggc gctggagggc aacagcgcag cgctaataaa ctcacgggct aatcacagtg   15180
gataatgccc aacgctcagg agacatttaa cggaggccaa tcaacaaata tggccttgtc   15240
atgggccttt aaacgatcgc tggtgggctt ttacattggc ccttttcctt tcttcataaa   15300
tcatgttgag ttaggggggg cctattactt ctgtacctga atcatatcgc taatatctat   15360
ggcctactcg atgtttgctc gatcgatagg gggggccagg cccctgctcg accccccctt   15420
gtctccgcca ctgaagaggg tcaaccaaat cccgtacttc tgaaggatat atcagatgga   15480
gataagctga gaacttgagc aagcgtatca ttcttatggg tacaatatgt tacaaggcga   15540
gatactgttc ttgaagagtg gtgttgtcca accacttgtc cttccagaaa cggatctcag   15600
agtcatcctt tattttggta gatttgtact gggaaagatg tttacttgct gccatgaggc   15660
ctgaccataa atgtgaatca ccagcagttc ttttagtgat gcatcatgca tggcaaccat   15720
ggagcaaaag agaaccccact gaagatggtc atgttctgcc atggccttt tatctcatgc   15780 atgttggagc gagcttgcta ggaatgagag gcaagtgaaa gcgaaggcgc acttcaatta   15840
```

```
cctccaggtt ggtgactctg tatcttgaaa catctaaatt taaattctct tgctttaatc   15900
acctccaatc acacaaacta tagacatttg agaaagtatt ggtaggtgtg cattaaggaa   15960
acgtgggaaa tattgcagct ctataaatta cgaaggatgg agttgctttt agaaaactac   16020
caaagagcaa ctatatattt cttagagtga tgcatcagga atcacaagta ttggactgaa   16080
catggtgacc ttgaacatag caagcttatt gatcactgtc atggcttttt ggtctcttca   16140
agcttgttgt agctaactag ctaggattag gattgagagg caactggaag caaatgcgca   16200
ctttgataac ataggtgaca tcatagactg gttggtcaat aagtaagatg acacaaagag   16260 gttcttttcag ctagcggatt tgtccacatc cctgtcattc ctttgcaaga accaatgctt   16320
ctcacgctga ccaacacact gtgtgtttcc atcatccaag tgattggcag cctcgtctag   16380
gtgatcaaca actagctcat cgccagccaa cttaacatgg actctggatc catgttatct   16440
gcaatgagct aagaaccact caagaaaaat gtggcacggg ataatcacat gatcatctcc   16500
tccttcacta ggtgcccaag agaaaactgt tgatacatg aacacaacat ttctgtttgt   16560
gccttttgtg gagcaatttc cccgtgtgtc agaggtcaga ccatttcgaa cgtgccaaat   16620
aaaccaaaga gtcatgagca gcttcttgcg ctccatctct tgcgaattca taacatcgtg   16680
acaccgctga tcattttaat gaaaaatgat gagactgcga gctttttga tctggaaaag   16740 cattgtcatt cagataatgc agagacaata tgatacctg ctcctagtgc ttgatgttgc   16800
tctgtacaga aaacttcttc atggaatgga atttaatttt taatagatt cttcttatca   16860 tgactttctt acgtgttagt atggggatga tactagttgc ttatagtact ccctccggtc   16920
atttttactc tgcgtattag atttgtatca agtcaaactt ccaaagtttt taccaaattt   16980
atattaaaaa tatcaacata tataatatca aatatatgta ctgtgaagct aagtttcata   17040
acgaatctaa cagtattgat ttggcattgt agatgttgat aatttttttt ataagtgtag   17100
tcaaagtaga gatactttga ctttagacaa aatgtatatg cagaataaaa agaaccgaag   17160
agagcacata ctttctagga attcagacca aacatacca aacattgtat gtaaagagat   17220
gcatgcaaca attacacaca aacatgtgga gctctgcacg catgtggcgc taatatacta   17280
ctactagtac tccctccgtc cgggtgcata gggcgcctaa gagaattcta aaattccaaa   17340
aatgttagac gtaattcaat taaatgctcc tcgtttattt aaatcgtctc gttttttctcc   17400 gttcgcttca ccaggtcgca ctccttctct taatctccca ccggtccacc tccaagtaat   17460
ctcgtgtgtg aaagcaaata gcatgcatgg ccatacgtga gagaagtaaa gagccaatgc   17520
atgcaccgta gcccggagct gattagacga gcaaattgtg cgggtgggct gtgcgacgtg   17580
ggacttttcc tttgcatgag ttagcccaaa cggccagcac taatgatagg attaatttcc   17640
aaattcagtt tcgattttga ggaaaacctg cgcacgcttt catccaatct caacccacct   17700
aaatcgcaga gcttttcttt agacgcccta tgcacctgga cggagggagt acctcctttc   17760
cggtttatag ggctcaattc aaaaatctca tcaaccaaga tagatggtga gtggtggaac   17820
aatttttgta gtttgcatag gcacacaatt aatgcactcg ttttcctcac aattttatgt   17880
ttaccaatgc attaattgca atgcatgcat acataaagta aatgcattga tcaattttct   17940
cttaatcttt gcatgcaatg atttaatgca ccttgaaatc tgaacatgtg atggggaaca   18000
atcaaattga gcattataaa acggaaaatc taaattttg ggataagccc tataaaccgg   18060
aaaggaggga gtagctgcat tgcatgtagt tgcagcggac tcaagaaacc actactactg   18120
tatgtgttgc agtagtaaag aagcttgatt ggtcccaact accactacta ctacaattac   18180
acacaaaccg acatgtgttg tactccctcc attttcttat acaaggccat tatgaaaaat   18240
```

```
atattttgca tctatataag gccactaaca gtaattgagg caaaaattaa tgaagttttc   18300
ttgtattagc aactttttta atatttgaga gtttttaaga tgacattgta ccttcgtggt   18360
gattaataca aggaacatct caatctaacc cttagactag ccataatggg tagtaacata   18420
gagta                                                                18425

<210> SEQ ID NO 21
<211> LENGTH: 21
<212> TYPE: DNA
<213> ORGANISM: Artificial Sequence
<220> FEATURE:
<223> OTHER INFORMATION: tc256739 Forward Primer

<400> SEQUENCE: 21
cccacctcaa gtctccctcc a                                              21

<210> SEQ ID NO 22
<211> LENGTH: 21
<212> TYPE: DNA
<213> ORGANISM: Artificial Sequence
<220> FEATURE:
<223> OTHER INFORMATION: tc256739 Reverse Primer

<400> SEQUENCE: 22
acctcggaga tgaggaactc g                                              21

<210> SEQ ID NO 23
<211> LENGTH: 20
<212> TYPE: DNA
<213> ORGANISM: Artificial Sequence
<220> FEATURE:
<223> OTHER INFORMATION: tc300731 Forward Primer

<400> SEQUENCE: 23
gctgcaacag cagaaaagag                                                20

<210> SEQ ID NO 24
<211> LENGTH: 20
<212> TYPE: DNA
<213> ORGANISM: Artificial Sequence
<220> FEATURE:
<223> OTHER INFORMATION: tc300731 Reverse Primer

<400> SEQUENCE: 24
gctgatcgag aattcccttg                                                20

<210> SEQ ID NO 25
<211> LENGTH: 23
<212> TYPE: DNA
<213> ORGANISM: Artificial Sequence
<220> FEATURE:
<223> OTHER INFORMATION: RB1R Primer

<400> SEQUENCE: 25
ctgaatggcg aatgctagag cag                                            23

<210> SEQ ID NO 26
<211> LENGTH: 20
<212> TYPE: DNA
<213> ORGANISM: Artificial Sequence
<220> FEATURE:
<223> OTHER INFORMATION: UBIF Primer
```

<400> SEQUENCE: 26
ctgcagtgca gcgtgacccg                                                         20

<210> SEQ ID NO 27
<211> LENGTH: 23
<212> TYPE: DNA
<213> ORGANISM: Artificial Sequence
<220> FEATURE:
<223> OTHER INFORMATION: RB2R Primer

<400> SEQUENCE: 27
cgtttcccgc cttcagttta aac                                                     23

<210> SEQ ID NO 28
<211> LENGTH: 1158
<212> TYPE: DNA
<213> ORGANISM: Secale cereale

<400> SEQUENCE: 28

```
atgctccgcc tccggagttg cctcgtcgcc cacctcctat cctctcccac cccctcccca    60
ctcccctctc tccaccgcct cctctccgcc gccgccgcgc ccgccgtctc cccagctcc    120
ggcttccaag tggaggacta cctcgtctcc acctgcggcc tcacccgagc gcaggccctc   180
aagaccgccc ccaagctctc ccacctcaag tccccgccca accccgacgc cgtccgctcc   240
ttcctcgccg gcctcggcct ctccggcgcc gacgtcgcgg ccctcgtcgc cagggacccg   300
ctcttcctct gcgccggcgt ggagggaaac ctgggcccccg ccgtcgccgg gctcaccgac   360
ctcggcctct cgcgctccga ggtcgcgcgc ctcgtctcgc tctccccgga ccgattccgc   420
cgcaagagcg tcgtcccaa ggtgcggtac tacctgcctc tcttcggctc ccccgcggac   480
ctcctctcgg gggtcaagac cggcctgttc cttctctccg tcgacctcga ccgggtcgtc   540
aagcccaacg tcgccgtcct gcgcaagtgc gggctagatg tttgtgatat tgccaagctg   600
ctcatccaaa tgccgaggat cgtcaccgcc agcccggggc gcaccctcgc gatggtcgcg   660
tgcgccgagc gcttgggtgt gccccgtggc tccgggatgt ttaggcaggc gctgcaggcc   720
gtcgcatccc tcagcgagga caagattgcc gccaaagtgg agcagttgaa gaagacactg   780
aggtggtcgg atgccgatgt cggcattgct gtctgcaagt ggccggctgt gctgaggtgg   840
tcaagggaca tgctgcagcg caagtccgag ttcctcttct ctgaggtggg cttggaaccg   900
gcgtacattg ctcaccgtcc ggcaatgctc ggtcttagct tggagcgccg cctcaagccc   960
cggtactatg ttatgaggtt tcttaaggaa aatggattgc tcagtcatgc cagagactac   1020
tattgtatgg tcttggtcag cgagaaggta tttgtggagc ggttcatacg cccccacaag   1080
caagctgcac cacacattgc tgaagactat gcagccgctt gcatagggga ggtgcctgct   1140
agattcagat ttacatga                                                  1158
```

<210> SEQ ID NO 29
<211> LENGTH: 385
<212> TYPE: PRT
<213> ORGANISM: Secale cereale

<400> SEQUENCE: 29

Met Leu Arg Leu Arg Ser Cys Leu Val Ala His Leu Leu Ser Ser Pro
1               5                   10                  15

Thr Pro Ser Pro Leu Pro Ser Leu His Arg Leu Leu Ser Ala Ala Ala
            20                  25                  30

```
Ala Pro Ala Val Ser Pro Ser Gly Phe Gln Val Glu Asp Tyr Leu
        35                  40                  45
Val Ser Thr Cys Gly Leu Thr Arg Ala Gln Ala Leu Lys Thr Ala Pro
 50                  55                  60
Lys Leu Ser His Leu Lys Ser Pro Ala Asn Pro Asp Ala Val Arg Ser
 65                  70                  75                  80
Phe Leu Ala Gly Leu Gly Leu Ser Gly Ala Asp Val Ala Ala Leu Val
                 85                  90                  95
Ala Arg Asp Pro Leu Phe Leu Cys Ala Gly Val Glu Gly Asn Leu Gly
            100                 105                 110
Pro Ala Val Ala Gly Leu Thr Asp Leu Gly Leu Ser Arg Ser Glu Val
            115                 120                 125
Ala Arg Leu Val Ser Leu Ser Pro Asp Arg Phe Arg Arg Lys Ser Val
        130                 135                 140
Val Pro Lys Val Arg Tyr Tyr Leu Pro Leu Phe Gly Ser Pro Ala Asp
145                 150                 155                 160
Leu Leu Ser Gly Val Lys Thr Gly Leu Phe Leu Leu Ser Val Asp Leu
                165                 170                 175
Asp Arg Val Val Lys Pro Asn Val Ala Val Leu Arg Lys Cys Gly Leu
            180                 185                 190
Asp Val Cys Asp Ile Ala Lys Leu Leu Ile Gln Met Pro Arg Ile Val
        195                 200                 205
Thr Ala Ser Pro Gly Arg Thr Leu Ala Met Val Ala Cys Ala Glu Arg
210                 215                 220
Leu Gly Val Pro Arg Gly Ser Gly Met Phe Arg Gln Ala Leu Gln Ala
225                 230                 235                 240
Val Ala Ser Leu Ser Glu Asp Lys Ile Ala Ala Lys Val Glu Gln Leu
                245                 250                 255
Lys Lys Thr Leu Arg Trp Ser Asp Ala Asp Val Gly Ile Ala Val Cys
            260                 265                 270
Lys Trp Pro Ala Val Leu Arg Trp Ser Arg Asp Met Leu Gln Arg Lys
        275                 280                 285
Ser Glu Phe Leu Phe Ser Glu Val Gly Leu Glu Pro Ala Tyr Ile Ala
290                 295                 300
His Arg Pro Ala Met Leu Gly Leu Ser Leu Glu Arg Arg Leu Lys Pro
305                 310                 315                 320
Arg Tyr Tyr Val Met Arg Phe Leu Lys Glu Asn Gly Leu Leu Ser His
                325                 330                 335
Ala Arg Asp Tyr Tyr Cys Met Val Leu Ser Glu Lys Val Phe Val
            340                 345                 350
Glu Arg Phe Ile Arg Pro His Lys Gln Ala Ala Pro His Ile Ala Glu
        355                 360                 365
Asp Tyr Ala Ala Ala Cys Ile Gly Glu Val Pro Ala Arg Phe Arg Phe
    370                 375                 380
Thr
385

<210> SEQ ID NO 30
<211> LENGTH: 1146
<212> TYPE: DNA
<213> ORGANISM: Secale cereale
```

<400> SEQUENCE: 30

```
atgctcctcc tcctccggca gcgcgtcctc tccgccgcgc catctccatc cacctcccct    60
ctccaccgcc tcctctccgc ggccgcgccc gccgtttccc ggaaccctag cttcgccgtg   120
gaggagtacc tcgtctccac ctgcggcctc acccgtgccc aggcactcaa ggcctccgcc   180
aagctctccc acctcaagtc ccccgccaag cccgacgccg tcctcgcctt cctcgccgga   240
ctcggcctct ccggcgccga catcgctgcc ctcgtcgcca aggacgcgcg gttcctctgc   300
gccggcgtgg agagaaccct gtcccccatc gtcgctgggc tcaccggcct tggcctgtca   360
aatgctgaga ctgcgcgcct cgtctcgctt gcccccgaca aattccgcca gagatccatc   420
gtctccaagc tagagtacta cctgccgctc gtcggctcca tcgacaactt ggtccggtcg   480
ctcaaacacg gcgccggcat cctcggctcc gacctcgaga gggtggtcaa gcccaatgtt   540
agtctcctag cagagtgcgg gctaggtgct tgtgatattg ccaagctgtt cgtccaaata   600
ccgaggatgc tgtgtgctaa ccagagcgt gtcctggaga tggttgcgtg tgccgaaagt   660
ataggtgtgt cccgtggctc tggaatgttc tggcaagcgc tgcacaccgt cgcatacgtc   720
agcgtggaca atatcgctgc cagagtggac tacttgaaga agacgtttag gtggtcagat   780
attgaggttg cattgctgt gtccaagggt ccatttctgc ttaggaggtc aaaggatatg   840
ctgaaacaca ggtcggagtt ccttatcact gagctagggt tgcagccggc ctacattgct   900
catcggccgg ctatgctcac ttacagcctg gagggccggc tcaggccccg ctactatgtt   960
gtgagatttc tcaaggaaaa tggattgcta gagcacgggc ggagctacta tacaacactg  1020
attagtactg agaaggtttt catggaaaag ttcatacgcc ctcacaagga agccgcacca  1080
cacctcgctg aagactacgc ggctgcttgc aaaggacaag tgccggctag attcagattt  1140
acatga                                                            1146
```

<210> SEQ ID NO 31
<211> LENGTH: 381
<212> TYPE: PRT
<213> ORGANISM: Secale cereale

<400> SEQUENCE: 31

```
Met Leu Leu Leu Leu Arg Gln Arg Val Leu Ser Ala Ala Pro Ser Pro
1               5                   10                  15

Ser Thr Ser Pro Leu His Arg Leu Leu Ser Ala Ala Pro Ala Val
            20                  25                  30

Ser Arg Asn Pro Ser Phe Ala Val Glu Glu Tyr Leu Val Ser Thr Cys
        35                  40                  45

Gly Leu Thr Arg Ala Gln Ala Leu Lys Ala Ser Ala Lys Leu Ser His
    50                  55                  60

Leu Lys Ser Pro Ala Lys Pro Asp Ala Val Leu Ala Phe Leu Ala Gly
65                  70                  75                  80

Leu Gly Leu Ser Gly Ala Asp Ile Ala Ala Leu Val Ala Lys Asp Ala
                85                  90                  95

Arg Phe Leu Cys Ala Gly Val Glu Arg Thr Leu Ser Pro Ile Val Ala
            100                 105                 110

Gly Leu Thr Gly Leu Gly Leu Ser Asn Ala Glu Thr Ala Arg Leu Val
        115                 120                 125

Ser Leu Ala Pro Asp Lys Phe Arg Gln Arg Ser Ile Val Ser Lys Leu
    130                 135                 140
```

Glu Tyr Tyr Leu Pro Leu Val Gly Ser Ile Asp Asn Leu Val Arg Ser
145                 150                 155                 160

Leu Lys His Gly Ala Gly Ile Leu Gly Ser Asp Leu Glu Arg Val Val
            165                 170                 175

Lys Pro Asn Val Ser Leu Leu Ala Glu Cys Gly Leu Gly Ala Cys Asp
        180                 185                 190

Ile Ala Lys Leu Phe Val Gln Ile Pro Arg Met Leu Cys Ala Lys Pro
    195                 200                 205

Glu Arg Val Leu Glu Met Val Ala Cys Ala Glu Ser Ile Gly Val Ser
210                 215                 220

Arg Gly Ser Gly Met Phe Trp Gln Ala Leu His Thr Val Ala Tyr Val
225                 230                 235                 240

Ser Val Asp Asn Ile Ala Ala Arg Val Asp Tyr Leu Lys Lys Thr Phe
                245                 250                 255

Arg Trp Ser Asp Ile Glu Val Gly Ile Ala Val Ser Lys Gly Pro Phe
            260                 265                 270

Leu Leu Arg Arg Ser Lys Asp Met Leu Lys His Arg Ser Glu Phe Leu
        275                 280                 285

Ile Thr Glu Leu Gly Leu Gln Pro Ala Tyr Ile Ala His Arg Pro Ala
    290                 295                 300

Met Leu Thr Tyr Ser Leu Glu Gly Arg Leu Arg Pro Arg Tyr Val
305                 310                 315                 320

Val Arg Phe Leu Lys Glu Asn Gly Leu Leu Glu His Gly Arg Ser Tyr
                325                 330                 335

Tyr Thr Thr Leu Ile Ser Thr Glu Lys Val Phe Met Glu Lys Phe Ile
            340                 345                 350

Arg Pro His Lys Glu Ala Ala Pro His Leu Ala Glu Asp Tyr Ala Ala
        355                 360                 365

Ala Cys Lys Gly Gln Val Pro Ala Arg Phe Arg Phe Thr
370                 375                 380

<210> SEQ ID NO 32
<211> LENGTH: 1158
<212> TYPE: DNA
<213> ORGANISM: Secale cereale

<400> SEQUENCE: 32

| | | |
|---|---|---|
| atgctccgcc tccggagttg cctcgtcacc caccttctat cctctcccac cacctcccca | 60 |
| ctcccctctc tccaccgcct cctctccgcc gccgccgcgc ccgccgtctc cccagctcc | 120 |
| ggcttcgacg tcgacgacta tctcgtctcc acctgcgggc tgacccgagc gcaggccctc | 180 |
| aaggccaccc ccaagctctc ccacctcaag tccccgcca accccgacgc cgtccgctcc | 240 |
| ttcctcgccg gcctcggcct ctccggcgcc gacgtcgcgg ccctcgtcgc cagggacccg | 300 |
| ctcttcctct gcgccggcgt ggacggaaac ctgggcccg ccgtcgccgg gctcaccgac | 360 |
| ctcggcctct cgcgggccga ggtcgcgcgc tcgtctcgc tctccccgga ccgattccgc | 420 |
| cgcaagagcg tcgtccccaa ggtgcggtac tacctgcctc tcttcggctc cccgcggac | 480 |
| ctcctctcgg gggtcaagac cggcctattc cttctctccg tcgacctcga ccgggtcgtc | 540 |
| aagcccaatg tcgccgtcct cgcaagtgc gggctaggtg tttgtgatat tgccaagctg | 600 |
| ctcatccaaa tgccgaggat cgtcaccgcc agccccgagc gcaccctcgc gatggtcgcg | 660 |
| tgcgccgagc gcttgggtgt gccccgtggc tccgggatgt ttaggcaggc gctgcaggcc | 720 |
| gtcgcatgcc tcagcgagga caagattgcc gccaaagtgg agcagttgaa gaagacactg | 780 |

-continued

```
aggtggtcgg atgccgatgt cggcattgct gtccgcaagt ggccgactgt gctgaggtgg    840
tcaagggaca tgctgcagcg caagtccgag ttcctcttct ctgaggtggg cttggaaccg    900
gcgtacgttg ctcaccgtcc ggcaatgctc ggtcttagct tggagcgccg gctcaagccc    960
aggtactatg ttatgaggtt tcttaaggaa aatggattgc tcagtcatgc cagagactac   1020
tattgtatgg tcttggtcag cgagaaggta tttgtggagc ggttcatacg cccccacaag   1080
caagctgtgc cacgcattgc tgaagactat gcagccgctt gcataggga ggtgcctgct    1140 agattcagat ttacatga                                                  1158
```

<210> SEQ ID NO 33
<211> LENGTH: 385
<212> TYPE: PRT
<213> ORGANISM: Secale cereale

<400> SEQUENCE: 33

```
Met Leu Arg Leu Arg Ser Cys Leu Val Thr His Leu Ser Ser Pro
 1               5                  10                  15

Thr Thr Ser Pro Leu Pro Ser Leu His Arg Leu Leu Ser Ala Ala
             20                  25                  30

Ala Pro Ala Val Ser Pro Ser Gly Phe Asp Val Asp Tyr Leu
         35                  40                  45

Val Ser Thr Cys Gly Leu Thr Arg Ala Gln Ala Leu Lys Ala Thr Pro
 50                  55                  60

Lys Leu Ser His Leu Lys Ser Pro Ala Asn Pro Asp Ala Val Arg Ser
 65                  70                  75                  80

Phe Leu Ala Gly Leu Gly Leu Ser Gly Ala Asp Val Ala Ala Leu Val
                 85                  90                  95

Ala Arg Asp Pro Leu Phe Leu Cys Ala Gly Val Asp Gly Asn Leu Gly
            100                 105                 110

Pro Ala Val Ala Gly Leu Thr Asp Leu Gly Leu Ser Arg Ala Glu Val
        115                 120                 125

Ala Arg Leu Val Ser Leu Ser Pro Asp Arg Phe Arg Arg Lys Ser Val
    130                 135                 140

Val Pro Lys Val Arg Tyr Tyr Leu Pro Leu Phe Gly Ser Pro Ala Asp
145                 150                 155                 160

Leu Leu Ser Gly Val Lys Thr Gly Leu Phe Leu Leu Ser Val Asp Leu
                165                 170                 175

Asp Arg Val Val Lys Pro Asn Val Ala Val Leu Arg Lys Cys Gly Leu
            180                 185                 190

Gly Val Cys Asp Ile Ala Lys Leu Leu Ile Gln Met Pro Arg Ile Val
        195                 200                 205

Thr Ala Ser Pro Glu Arg Thr Leu Ala Met Val Ala Cys Ala Glu Arg
    210                 215                 220

Leu Gly Val Pro Arg Gly Ser Gly Met Phe Arg Gln Ala Leu Gln Ala
225                 230                 235                 240

Val Ala Cys Leu Ser Glu Asp Lys Ile Ala Ala Lys Val Glu Gln Leu
                245                 250                 255

Lys Lys Thr Leu Arg Trp Ser Asp Ala Asp Val Gly Ile Ala Val Arg
            260                 265                 270

Lys Trp Pro Thr Val Leu Arg Trp Ser Arg Asp Met Leu Gln Arg Lys
        275                 280                 285

Ser Glu Phe Leu Phe Ser Glu Val Gly Leu Glu Pro Ala Tyr Val Ala
    290                 295                 300
```

```
His Arg Pro Ala Met Leu Gly Leu Ser Leu Glu Arg Arg Leu Lys Pro
305                 310                 315                 320

Arg Tyr Tyr Val Met Arg Phe Leu Lys Glu Asn Gly Leu Leu Ser His
            325                 330                 335

Ala Arg Asp Tyr Tyr Cys Met Val Leu Val Ser Glu Lys Val Phe Val
            340                 345                 350

Glu Arg Phe Ile Arg Pro His Lys Gln Ala Val Pro Arg Ile Ala Glu
        355                 360                 365

Asp Tyr Ala Ala Ala Cys Ile Gly Glu Val Pro Ala Arg Phe Arg Phe
        370                 375                 380

Thr
385
```